United States Patent
Chaudhary et al.

(10) Patent No.: US 9,931,332 B2
(45) Date of Patent: Apr. 3, 2018

(54) COMPOSITIONS AND METHODS FOR TREATING PRIMARY EFFUSION LYMPHOMA

(71) Applicants: Preet M. Chaudhary, Toluca Lake, CA (US); Ramakrishnan Gopalakrishnan, Los Angeles, CA (US)

(72) Inventors: Preet M. Chaudhary, Toluca Lake, CA (US); Ramakrishnan Gopalakrishnan, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/814,149

(22) Filed: Jul. 30, 2015

(65) Prior Publication Data

US 2016/0136146 A1 May 19, 2016

Related U.S. Application Data

(60) Provisional application No. 62/031,053, filed on Jul. 30, 2014.

(51) Int. Cl.
| | |
|---|---|
| A61K 31/454 | (2006.01) |
| A61K 31/519 | (2006.01) |
| A61K 31/517 | (2006.01) |
| A61K 31/00 | (2006.01) |

(52) U.S. Cl.
CPC ............ *A61K 31/454* (2013.01); *A61K 31/00* (2013.01); *A61K 31/517* (2013.01); *A61K 31/519* (2013.01)

(58) Field of Classification Search
None
See application file for complete search history.

(56) References Cited

FOREIGN PATENT DOCUMENTS

WO    WO 2010/111631    *    9/2010    ........... C12N 5/0783

OTHER PUBLICATIONS

Fux et al (AIDS 25:878-880, 2011).*
Chen et al (The Oncologist 15:569-576, 2007).*
Tolani et al (Oncogene 29:2928-2937, published online Jun. 24, 2013).*

* cited by examiner

*Primary Examiner* — Craig D Ricci
(74) *Attorney, Agent, or Firm* — DLA Piper LLP (US)

(57) ABSTRACT

Methods for treating primary effusion lymphoma (PEL) are provided. The methods include administering to a patient in need thereof an effective amount of an immunomodulatory compound. Suitable immunomodulatory compounds include compounds having the formula:

Formula IV wherein X in Formula IV may be independently selected from the group that includes hydrogen, a halide, an aliphatic group and an amine group.

5 Claims, 43 Drawing Sheets
(14 of 43 Drawing Sheet(s) Filed in Color)

Figures 3A-C
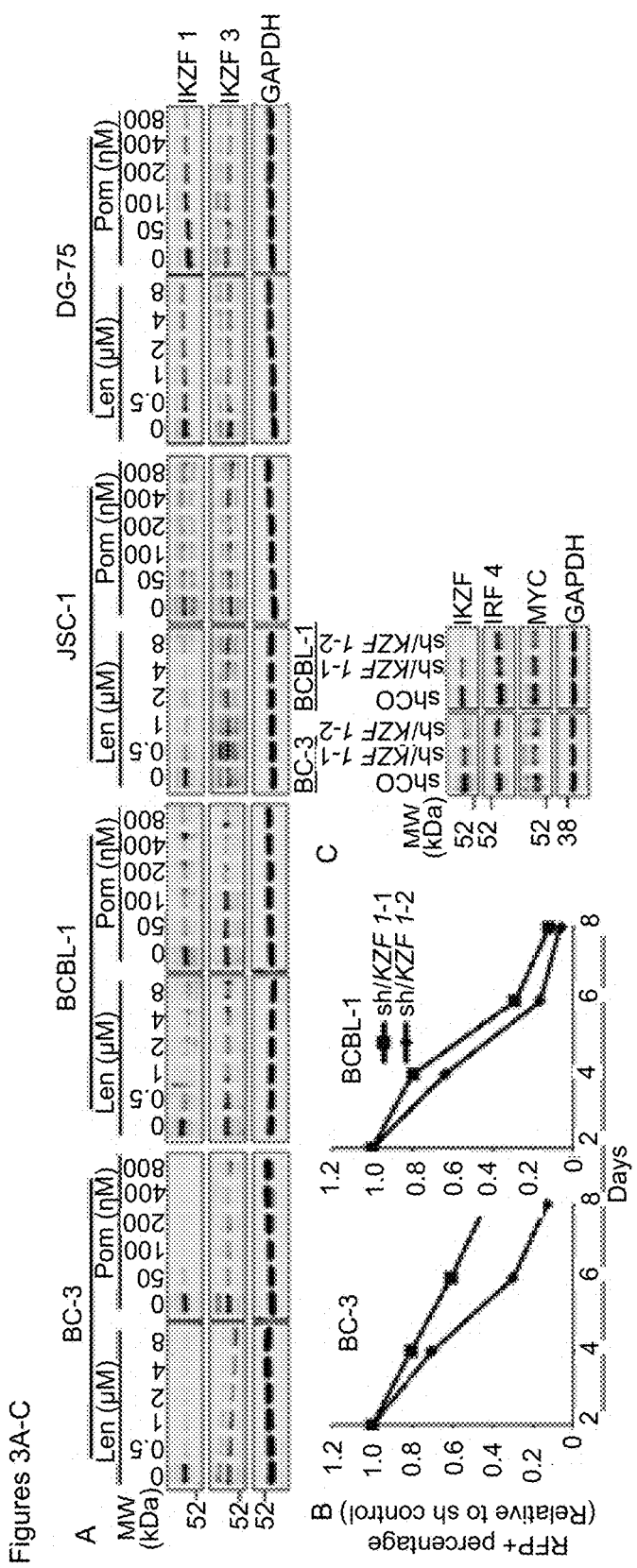

Figures 4B-D
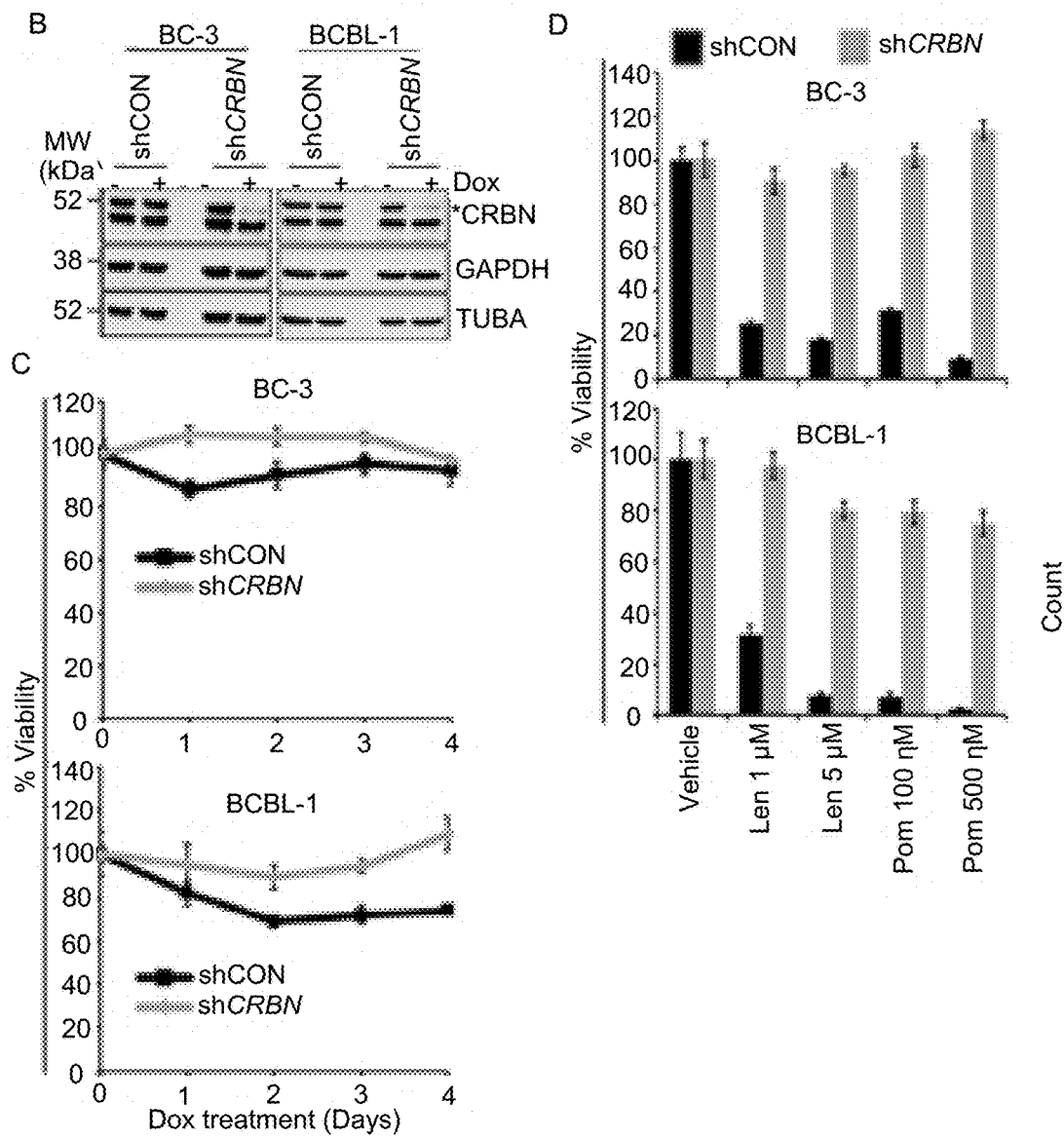

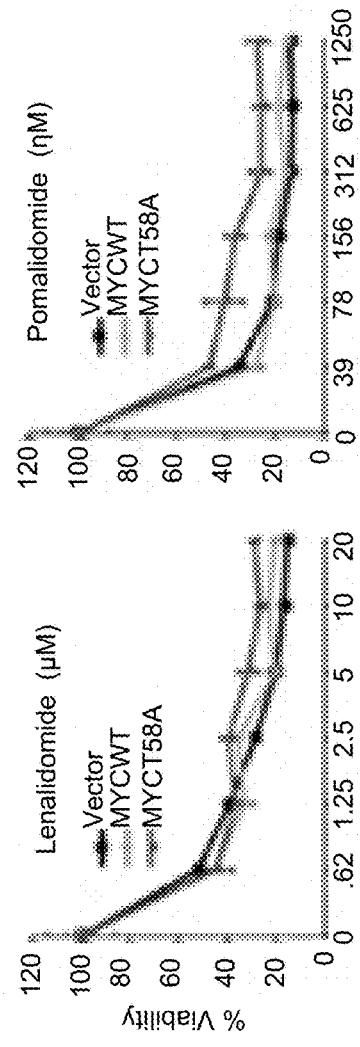
Figure 5B
Figure 5C
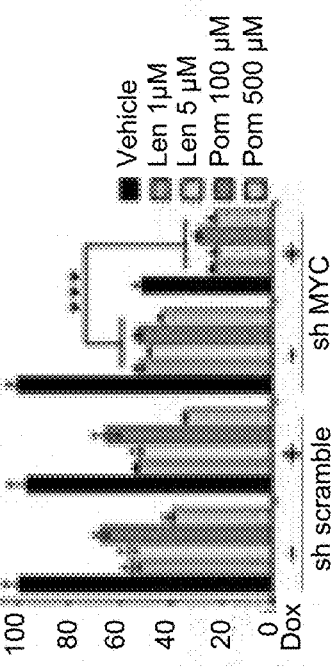
Figure 5D
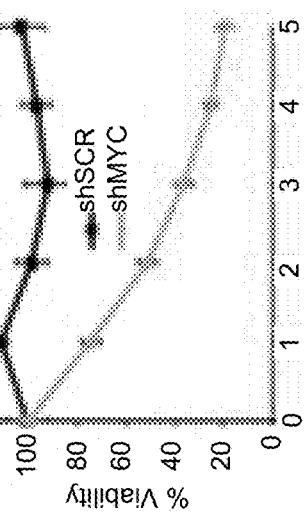
Figure 5E
Figure 5F
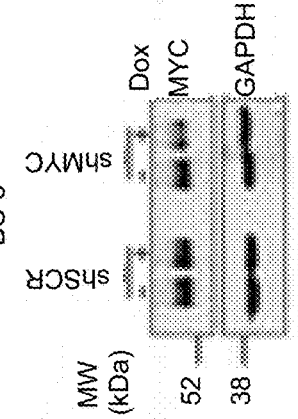

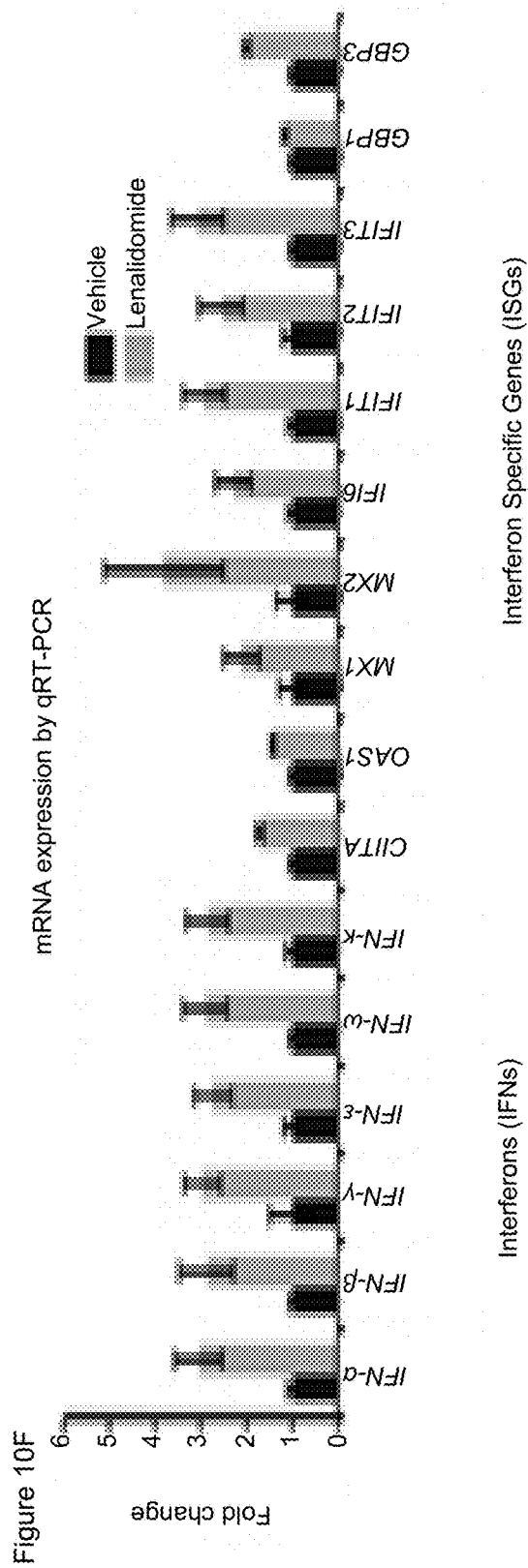

| | Len (ηM) | JQ-1 (ηM) | Fa | CI |
|---|---|---|---|---|
| 1 | 125 | 25 | 0.34 | 1.448 |
| 2 | 125 | 50 | 0.65 | 0.18 |
| 3 | 125 | 100 | 0.76 | 0.081 |
| 4 | 250 | 25 | 0.68 | 0.258 |
| 5 | 250 | 50 | 0.71 | 0.211 |
| 6 | 250 | 100 | 0.8 | 0.099 |
| 7 | 500 | 25 | 0.75 | 0.287 |
| 8 | 500 | 50 | 0.8 | 0.181 |
| 9 | 500 | 100 | 0.84 | 0.119 |
| 10 | 1000 | 25 | 0.8 | 0.355 |
| 11 | 1000 | 50 | 0.81 | 0.322 |
| 12 | 1000 | 100 | 0.92 | 0.054 |

BCBL-1

| | Len (ηM) | JQ-1 (ηM) | Fa | CI |
|---|---|---|---|---|
| 1 | 125 | 25 | 0.63 | 0.28 |
| 2 | 125 | 50 | 0.56 | 0.459 |
| 3 | 125 | 100 | 0.71 | 0.307 |
| 4 | 250 | 25 | 0.7 | 0.362 |
| 5 | 250 | 50 | 0.7 | 0.403 |
| 6 | 250 | 100 | 0.84 | 0.206 |
| 7 | 500 | 25 | 0.8 | 0.393 |
| 8 | 500 | 50 | 0.8 | 0.415 |
| 9 | 500 | 100 | 0.94 | 0.111 |
| 10 | 1000 | 25 | 0.89 | 0.37 |
| 11 | 1000 | 50 | 0.89 | 0.38 |
| 12 | 1000 | 100 | 0.96 | 0.13 |

| | Len (ηM) | IBET151 (ηM) | Fa | CI |
|---|---|---|---|---|
| 1 | 125 | 100 | 0.4 | 0.57 |
| 2 | 125 | 200 | 0.65 | 0.456 |
| 3 | 125 | 400 | 0.85 | 0.364 |
| 4 | 250 | 100 | 0.48 | 0.44 |
| 5 | 250 | 200 | 0.71 | 0.364 |
| 6 | 250 | 400 | 0.88 | 0.295 |
| 7 | 500 | 100 | 0.65 | 0.2390 |
| 8 | 500 | 200 | 0.76 | 0.296 |
| 9 | 500 | 400 | 0.92 | 0.204 |
| 10 | 1000 | 100 | 0.67 | 0.23 |
| 11 | 1000 | 200 | 0.83 | 0.207 |
| 12 | 1000 | 400 | 0.94 | 0.158 |

| | Len (ηM) | IBET151 (ηM) | Fa | CI |
|---|---|---|---|---|
| 1 | 125 | 100 | 0.74 | 0.458 |
| 2 | 125 | 200 | 0.82 | 0.599 |
| 3 | 125 | 400 | 0.97 | 0.398 |
| 4 | 250 | 100 | 0.82 | 0.444 |
| 5 | 250 | 200 | 0.9 | 0.459 |
| 6 | 250 | 400 | 0.96 | 0.489 |
| 7 | 500 | 100 | 0.91 | 0.372 |
| 8 | 500 | 200 | 0.95 | 0.359 |
| 9 | 500 | 400 | 0.97 | 0.458 |
| 10 | 1000 | 100 | 0.95 | 0.367 |
| 11 | 1000 | 200 | 0.97 | 0.348 |
| 12 | 1000 | 400 | 0.98 | 0.421 |

| | Len (ηM) | PFI-1 (ηM) | Fa | CI |
|---|---|---|---|---|
| 1 | 125 | 250 | 0.53 | 0.497 |
| 2 | 125 | 500 | 0.67 | 0.396 |
| 3 | 125 | 1000 | 0.83 | 0.274 |
| 4 | 250 | 250 | 0.63 | 0.376 |
| 5 | 250 | 500 | 0.72 | 0.341 |
| 6 | 250 | 1000 | 0.88 | 0.181 |
| 7 | 500 | 250 | 0.74 | 0.254 |
| 8 | 500 | 500 | 0.81 | 0.217 |
| 9 | 500 | 1000 | 0.94 | 0.061 |
| 10 | 1000 | 250 | 0.77 | 0.303 |
| 11 | 1000 | 500 | 0.87 | 0.151 |
| 12 | 1000 | 1000 | 0.96 | 0.053 |

| | Len (ηM) | PFI-1 (ηM) | Fa | CI |
|---|---|---|---|---|
| 1 | 125 | 250 | 0.54 | 0.571 |
| 2 | 125 | 500 | 0.76 | 0.435 |
| 3 | 125 | 1000 | 0.92 | 0.304 |
| 4 | 250 | 250 | 0.76 | 0.405 |
| 5 | 250 | 500 | 0.86 | 0.349 |
| 6 | 250 | 1000 | 0.95 | 0.247 |
| 7 | 500 | 250 | 0.88 | 0.354 |
| 8 | 500 | 500 | 0.93 | 0.285 |
| 9 | 500 | 1000 | 0.96 | 0.264 |
| 10 | 1000 | 250 | 0.93 | 0.398 |
| 11 | 1000 | 500 | 0.96 | 0.295 |
| 12 | 1000 | 1000 | 0.97 | 0.3 |

| Range of CI | Description |
|---|---|
| <0.1 | Very strong synergism |
| 0.1-0.3 | Strong synergism |
| 0.3-0.7 | Synergism |
| 0.7-0.85 | Moderate synergism |
| 0.85-0.90 | Slight synergism |
| 0.9-1.10 | Nearly additive |
| 1.1-1.2 | Slight antagonism |
| 1.2-1.45 | Moderate antagonism |
| 1.45-3.3 | Antagonism |
| 3.3-10 | Strong antagonism |
| >10 | Very strong antagonism |

COMPOSITIONS AND METHODS FOR TREATING PRIMARY EFFUSION LYMPHOMA

CROSS-REFERENCE TO RELATED APPLICATIONS

This application claims priority to U.S. Provisional Application Ser. No. 62/031,053, filed on Jul. 30, 2014, the entire contents of which are incorporated herein by reference in their entirety.

STATEMENT REGARDING FEDERALLY SPONSORED RESEARCH OR DEVELOPMENT

This invention was made with government support under National Institutes of Health grants CA139119, DE019811, SC CTSI UL1TR000130 and P30CA014089. The government has certain rights in the invention.

BACKGROUND OF THE INVENTION

Primary effusion lymphoma (PEL) is an aggressive type of non-Hodgkin lymphoma localized predominantly in body cavities and occasionally in extracavitary regions (Patel and Xiao, 2013). Kaposi's sarcoma associated herpesvirus (KSHV) is the causative agent for PEL (Cesarman et al., 1995) and this disease primarily occurs in patients with human immunodeficiency virus (HIV) infection and severe immunodeficiency (Patel and Xiao, 2013). However, it can also occur in HIV negative individuals who are immunocompromised as a result of solid-organ transplantation (Riva et al., 2012) and very rarely in elderly population. The prognosis of PEL is very poor with a median survival of 4 and 6 months in HIV positive and negative patients, respectively (Kobayashi et al., 2007). Although administration of cytotoxic chemotherapeutic agents represents the current standard of care (Riva et al., 2012). Impaired clinical condition and severe immunodeficiency enhanced the chemotherapy toxicity and increased the risk of treatment-related mortality (Boulanger et al., 2005). At present there is no standard treatment available for PEL and it remains an incurable malignancy. Thus there is an urgent need to develop new treatment regimens for PEL.

Interferon regulatory factor 4 (IRF4), a transcription factor expressed in cells of the immune system, is an essential regulator at multiple steps in B-Cell differentiation and is associated with many lymphoid malignancies (Shaffer et al., 2009). It has been shown that 100% of PEL cases express IRF-4 and its expression was a selective feature of PEL among lymphomas involving the serous body cavities as secondary lymphomatous effusions generally failed to express this protein (Carbone et al., 2000). Lenalidomide and pomalidomide which are derived from the parent compound thalidomide (all of them FDA approved) are collectively referred to as immunomodulatory drugs (IMiDs). Both lenalidomide and pomalidomide demonstrated more potent anti-myeloma, anti-inflammatory and immunomodulatory activities than thalidomide (Zhu et al., 2013). The anti-myeloma activity of IMiDs is mediated via both direct and indirect mechanisms. As their name implies these drugs modulate the immune activity by enhancing the CD4+ and CD8+ T cell co-stimulation and they are also potent inducers of T cell proliferation and enhance the production of interleukin-2 (IL-2) and interferon-γ (IFN-γ) (Zhu et al., 2013). It has been recently found that the direct cellular targets of IMiDs are Cereblon (CRBN) (Ito et al., 2010), Ikaros family zinc finger-1 (IKZF1/IKAROS), Ikaros family zinc finger-3 (IKZF3/AIOLOS) (Kronke et al., 2014; Lu et al., 2014) and Interferon regulatory factor-4 (IRF-4) (Yang et al., 2012). Since, IRF-4 is expressed in all PEL cases we hypothesized that targeting IRF-4 in PEL by IMiDs would be effective against this disease. We found that IMiDs lenalidomide and pomalidomide at physiologically achievable concentrations are efficacious and selective against PEL in a panel of cell lines tested. Further, we discovered that shRNA mediated knockdown of MYC enhanced the anti-proliferative potential of IMiDs in PEL and low dose combinations of IMiDs with bromodomain-containing protein 4 (BRD4) inhibitors (which directly inhibit MYC transcription) displayed synergistic anti-proliferative potential against PEL.

SUMMARY OF THE INVENTION

One aspect of the present invention is directed to the use of immunomodulatory compounds, including several approved immunomodulatory drugs (IMiDs) and their derivatives in the treatment of primary effusion lymphoma (PEL). The treatment includes administering to a patient in need thereof an effective amount of an immunomodulatory compound. Immunomodulatory compounds suitable for use in connection with the present include:

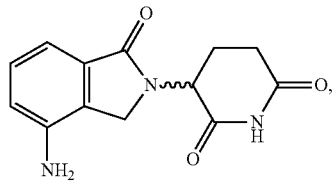

Formula I

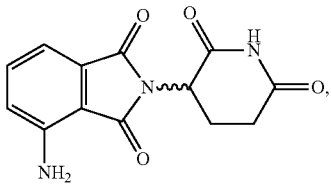

Formula II

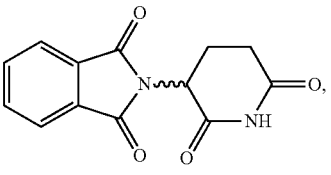

Formula III

Formula IV and

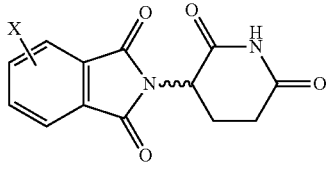

Formula V wherein X in both Formula IV and Formula V may be independently selected from the group consisting of hydrogen, a halide, an aliphatic group and an amine group. Wavy lines represent the two possible stereoisomers, and the compounds, compositions and treatments of the present invention my include either a mixture of the two possible stereoisomers, or either one separately.

Another aspect of the present invention is the discovery that immunomodulatory compounds and BRD4 inhibitors have synergistic activity in the treatment of PEL. As such, another aspect of the present invention is a combination treatment for PEL comprising administering to a patient in need thereof an effective amount of an immunomodulatory compound and a BRD4 inhibitor. These compounds may be administered together as a single pharmaceutical composition. Alternatively, they may be administered separately in a manner suitable for realizing the synergistic effects of the combination treatment.

Suitable immunomodulatory compounds include the compounds defined by Formulas I-V. Suitable BRD4 inhibitors for use in connection with this aspect of the present invention include BRD4 inhibitors having the following formulas:

Formula VI

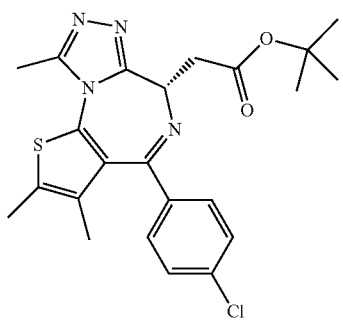

(also known as compound JQ-1)

Formula VII

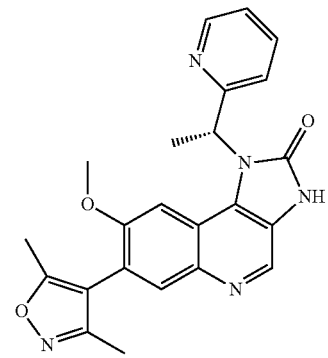

I (also known as compound IBET151)

Formula VIII

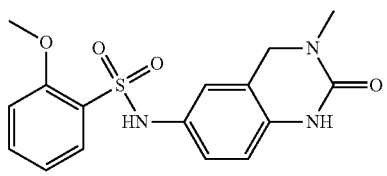

(also known as compound PFI-1)

Other suitable BRD4 inhibitors are described in R. Sanchez et al., The bromodomain: From epigenome reader to druggable target, Biochim Biophys Acta. 2014 August; 1839(8) and Filappakopoulos et al., "Targeting Bromodomains: epigenetic readers of lysine acetylation, Nature Reviews, Vol. 13, pp. 337-356 (May 2014), both of which are incorporated herein by reference in their entirety.

Other aspects and advantages of the invention will be apparent from the following description and the appended claims.

BRIEF DESCRIPTION OF THE DRAWINGS

The file of this patent contains at least one drawing executed in color. Copies of this patent with color drawings will be provided by the Office upon request and payment of the necessary fee.

FIG. 1A, Expression of IRF4 in a panel of 33 hematological cancer cell lines. Cell lysates were prepared from logarithmically growing cell lines and blotted for IRF4. FIG. 1B, BC-3 cells stably expressing tetracycline-inducible H1 promoter (H1/TO)-driven shRNA targeting IRF4, clone F11 (shIRF4-F11) and shRNA targeting scrambled sequence (shSCR) were treated with doxycycline (Dox, 500 ng/ml) for 3 days and immunoblotted for the expression of IRF4, MYC, PARP and TUBA (Tubulin, loading control) FIG. 1C, BC-3 cells stably expressing shSCR and shIRF4-F11 were treated with Dox for indicated time points and cell viability was measured by MTS assay as described in materials and methods. The values shown are mean±SE (n=3). FIG. 1D, Cell cycle analysis of BC-3 cells stably expressing shSCR and shIRF4-F11 treated with and without Dox for 48 hours (h). Cells were stained with propidium iodide (PI) and analyzed by flow cytometry. FIG. 1E, BC-3 cells stably expressing shSCR and sh IRF4-F11 were treated with Dox for 72 h. Cells were then stained with Hoescht 33342 and photographed. FIG. 1F, BC-3 cells stably expressing shSCR and shIRF4-F11 were treated with Dox for 48 h, stained with annexinV-FITC/PI, and analyzed for apoptosis by flow cytometry. FIG. 1G, Panel of cell lines were treated with increasing concentrations of lenalidomide in µmol/L (µM) and pomalidomide in nmol/L (nM) for 5 days, and cell viability was measured using an MTS assay. An oval shaped marking shows the cell lines which are sensitive to treatment and these cell lines were marked by a black arrow in the legend. A thick black perpendicular line in the X-axis marks the physiologically achievable concentrations of the respective drugs in human. The values shown are mean±SE (n=3). PEL:Primary Effusion Lymphoma; CML:Chronic Myeloid Leukemia; T-ALL:T-cell Acute Lymphoblastic Leukemia; AML: Acute Myeloid Leukemia; ABC-DLBCL:Activated B-Cell Diffuse Large B-Cell Lymphoma; GCB-DLBCL: Germinal Center B-cell Diffuse Large B-Cell Lymphoma; MCL:Mantle Cell Lymphoma; WM:Waldenstrom's Macroglobunemia; MW:Molecular Weight; kDa:Kilodalton; Dox:Doxycycline; L:Lenalidomide; P:Pomalidomide; L&P: Lenalidomide and Pomalidomide.

FIG. 2A, Immunoblot analysis showing the effect of lenalidomide and pomalidomide at the indicated doses for 48 h on the expression of IRF4, MYC and TUBA in BC-3, BCBL-1, JSC-1 and DG-75 cells. FIG. 2B, Cell cycle analysis of BC-3, BCBL-1, JSC-1 and DG-75 cells treated with indicated doses of lenalidomide and pomalidomide for 48 h. Cells were stained with propidium iodide (PI) and analyzed by flow cytometry. FIG. 2C, Heat map representation of 992 genes that are up- or downregulated ($p_{FDR}<0.05$) in BC-3 and BCBL-1 cells following 24 h treatment with Lenalidomide (5 µM). FIG. 2D, Gene set enrichment analysis showing enrichment of gene sets which are involved in interferon signaling among genes affected by lenalidomide treatment in PEL. NES, normalized enrichment score; q, false discovery rate. FIG. 2E, PEL cells are sensitive to interferons (IFNs) α, β and γ. BC-3, BCBL-1, JSC-1, BC-1, VG-1, BJAB and DG-75 cells were treated with indicated concentrations of recombinant IFNs for 5 days, and cell viability was measured using an MTS assay.

FIGS. 3A-3E. IMiDs rapidly downregulate the protein levels of Ikaros (IKZF1) and knocking down IKZF1 using specific shRNAs is toxic to PEL cells via down-regulating the expression of IRF4 and MYC. FIG. 3A, Immunoblot analysis showing the effect of lenalidomide and pomalidomide at the indicated doses for 48 h on the expression of IKZF1 (Ikaros), IKZF3 (Aiolos) and GAPDH (loading control) in BC-3, BCBL-1, JSC-1 and DG-75 cells. FIG. 3B, Change in % red fluorescent protein (RFP) positivity over time in BC-3 and BCBL-1 cells infected with viruses encoding RFP and the indicated shRNAs. The day 2% RFP for each virus was normalized to 1, and subsequent values are expressed relative to cells infected with a virus encoding RFP and a control shRNA. FIG. 3C, Immunoblot analysis of BC-3 and BCBL-1 cells transiently infected with lentiviruses expressing the indicated shRNAs for 72 hours. FIG. 3D, qRT-PCR analysis showing the levels of mRNA expression in BC-3, BCBL-1 and JSC-1 cells treated with lenalidomide (5 µM) for 24 hours. Real time PCR reactions were carried out in triplicate and the data are presented as fold change in target gene expression (mean±SE, n=2). FIG. 3E, Immunoblot analysis showing the expression IKZF1, IRF4, MYC, TUBA and HSP90 (loading controls) in BC-3 and BCBL-1 cells treated with indicated concentrations of IMiDs for 12, 24, 48, and 72 h.

FIGS. 4A-4H. Cereblon is dispensable for the survival of PEL cells but is essential for the antiproliferative activity of IMiDs in PEL cells. FIG. 4A, Immunoblot analysis showing the effect of lenalidomide (Len) and pomalidomide (Pom) at the indicated doses for 48 h on the expression of cereblon (CRBN) and GAPDH in BC-3, BCBL-1, BC-1 and JSC-1 cells. The band corresponding to cereblon is marked with an asterisk. FIG. 4B, BC-3 and BCBL-1 cells stably expressing tetracycline-inducible shRNA targeting CRBN (shCRBN) and shRNA targeting scrambled sequence (shCON) were treated with doxycycline (Dox, 500 ng/ml) for 4 days and immunoblotted for the expression of CRBN, GAPDH and TUBA. FIG. 4C, BC-3 and BCBL-1 cells stably expressing shCON and shCRBN were treated with doxycycline (Dox, 500 ng/ml) for indicated time points and cell viability was measured by MTS assay. The values shown are mean±SE (n=3). FIG. 4D, BC-3 and BCBL-1 cells stably expressing shCON and shCRBN were pre-treated with Dox for 3 days followed by treatment with vehicle and IMiDs at indicated concentrations for 6 days in the presence of Dox and cell viability was measured by MTS assay. The values shown are mean±SE (n=3). FIG. 4E and FIG. 4F, Cell cycle and apoptosis analysis of BC-3 and BCBL-1 cells stably expressing shCON and shCRBN pre-treated with Dox for 3 days followed by treatment with vehicle and IMiDs at indicated concentrations for 48 h (Cell cycle) and 72 h (Apoptosis) in the presence of Dox. FIG. 4G, BC-3 and BCBL-1 cells stably expressing shCON and shCRBN were pre-treated with Dox for 3 days followed by treatment with vehicle or IMiDs along with Dox in the presence of 100 µg/ml of cycloheximide (CHX) for 0, 1, 2, and 3 h respectively. Whole cell lysates were immunoblotted for IKZF1, CRBN and GAPDH. FIG. 4H, Effect of NEDD8 activating enzyme inhibitor MLN4924 on the activity of IMiDs. BC-3 and BCBL-1 cells were pre-treated with 250 ηM of MLN4924 for 1 hour followed by treatment with vehicle or indicated concentrations of IMiDs for 15 hours. Whole cell lysates were immunoblotted for IKZF1 and GAPDH.

FIGS. 5A-5H. Knocking down MYC enhances the antiproliferative effect of IMiDs in PEL. FIG. 5A, Expression levels of CRBN, IKZF1 and MYC in a panel of 33 hematological cancer cell lines. Cell lysates were prepared from logarithmically growing cell lines and immunoblotted for indicated proteins. FIG. 5B, BC-3 cells stably transduced with empty retroviral vector, wild type (WT) MYC and MYC T58A mutant were immunoblotted for MYC and GAPDH. FIG. 5C, BC-3 cells stably expressing an empty retroviral vector, wild type (WT) MYC and MYC T58A mutant respectively were treated with increasing concentrations of IMiDs for 4 days and cell viability was measured by MTS assay. The values shown are mean±SE (n=3). FIG. 5D, BC-3 cells stably expressing tetracycline-inducible H1 promoter (H1/TO)-driven shRNA targeting MYC (shMYC) and shRNA targeting scrambled sequence (shSCR) were treated with doxycycline (Dox, 500 ng/ml) for 4 days and immunoblotted for the expression of MYC and GAPDH. FIG. 5E, BC-3 cells stably expressing shSCR and shMYC were treated with Dox for indicated time points and cell viability was measured by MTS assay. The values shown are mean±SE (n=3). FIG. 5F, BC-3 cells stably expressing shSCR and shMYC were treated in the presence/absence of Dox with indicated concentrations of IMiDs or vehicle for 72 h and cell viability was measured by MTS assay. Asterisks (***) indicate significance at the level of $p \leq 0.001$. The values shown are mean±SE (n=3). FIG. 5G and FIG. 5H, Cell cycle and apoptosis analysis of BC-3 cells stably expressing shSCR and shMYC that were treated in the presence/absence of Dox with indicated concentrations of IMiDs or vehicle for 72 h (Cell cycle) and 48 h (Apoptosis).

FIG. 6A, BC-3 and BCBL-1 cells were treated with low doses lenalidomide (Len) in combination with low doses of three structurally different BRD4 inhibitors JQ-1, IBET151 and PFI-1 followed by the calculation of combination index (CI) values using the calcusyn software which is based on the method of Chou and Talalay (Chou and Talalay, 1983). Each BRD4 inhibitor was tested in combination with lenalidomide at 12 different combinations. CI values of <1 denotes synergism and CI values >1 denotes antagonism. Data presented is representative of 2 individual experiments performed in triplicate. FIG. 6B, BC-3 and BCBL-1 cells were treated with vehicle, lenalidomide 1 µM (L), pomalidomide 100 nM (P100), JQ-1 50 nM (J50), JQ-1 100 nM (J100) and the combinations for 48 h. Whole cell lysates were immunoblotted for MYC, IRF4, PARP and GAPDH. FIG. 6C, qRT-PCR analysis showing the levels of mRNA expression in BC-3 and BCBL-1 cells treated with vehicle or indicated concentrations of lenalidomide and JQ-1 or the combination for 48 h. Real time PCR reactions were carried out in triplicate and the data are presented as fold change in target gene expression (mean±SE). FIG. 6D and FIG. 6E, Cell cycle and apoptosis analysis of BC-3 and BCBL-1 cells treated with vehicle or indicated concentrations of Len, pomalidomide (Pom) and JQ-1 or the combination for 48 h (Cell cycle) and 72 h (Apoptosis).

FIG. 7A, BC-3 cells stably expressing tetracycline-inducible H1 promoter (H1/TO)-driven shRNA targeting BRD4 (shBRD4) and shRNA targeting scrambled sequence (shSCR) were treated with doxycycline (Dox, 500 ng/ml) for 4 days and immunoblotted for the expression of BRD4 and GAPDH. The band corresponding to BRD4 is marked with an asterisk. FIG. 7B, BC-3 cells stably expressing shSCR and shBRD4 were treated with Dox for 4 days and cell viability was measured by MTS assay. The values shown are mean±SE (n=3). FIG. 7C, BC-3 cells stably expressing shSCR and shBRD4 were treated in the presence/absence Dox with indicated concentrations of IMiDs or vehicle for 96 h and cell viability was measured by MTS assay. The values shown are mean±SE (n=3). FIG. 7D, Apoptosis analysis of BC-3 cells stably shSCR and shBRD4 that were treated in the presence/absence of Dox with indicated concentrations of IMiDs or vehicle for 72 h. FIG. 7E, Survival curves (Kaplan-Meier) of mice injected with BC-3 cells followed by indicated treatments. The survival curve was generated in GraphPad Prism 5 software and statistical values for the curves are calculated by log rank (Mantel-Cox) test. Len:Lenalidomide; Pom:Pomalidomide; Asterisks (**) indicate significance at the level of p≤0.01.

FIG. 8A, BC-3 cells stably expressing tetracycline-inducible H1 promoter (H1/TO)-driven shRNA targeting IRF4 (shIRF4) and shRNA targeting scrambled sequence (shSCR) were treated with doxycycline (Dox, 500 ng/ml) for 4 days and immunoblotted for the expression of IRF4, GAPDH and HSP90 (GAPDH and HSP90 are loading controls). FIG. 8B, BC-3 cells stably expressing shSCR and shIRF4 were treated with Dox for 3 days and cell viability was measured by MTS assay. The values shown are mean±SE (n=3). FIG. 8C, BC-3 cells stably expressing shSCR and single cell clones of shIRF4 denoted F11, G10, E2, F3, B4, C8, B11 and C7 were treated with Dox for 3 days and immunoblotted for the expression of IRF4, MYC, PARP, GAPDH and HSP90. FIG. 8D, BC-3 cells stably expressing shSCR and single cell clones of shIRF4 denoted F11, G10, E2, F3, B4, C8, B11 and C7 were treated with Dox for 3 days and cell viability was measured by MTS assay. The values shown are mean±SE (n=3). MW:Molecular Weight; kDa:Kilodalton.

FIGS. 10A-10F. FIG. 10A, Cell cycle analysis of BC-1, VG-1, and OCILY-8 cells treated with indicated doses of lenalidomide in μmol/L (Len, μM) and pomalidomide in nmol/L (Pom, nM) for 48 h. IMiDs treatment resulted in G1 arrest in BC-1, and VG-1 cells. There is no significant change in the cell cycle profile of OCILY-8 upon treatment with IMiDs. Cells were stained with propidium iodide (PI) and analyzed by flow cytometry. IMiDs have no effect on constitutive NF-κB pathway present in PEL cells. FIG. 10B, BC-3, BCBL-1 and BC-1 cells stably expressing luciferase gene under the control of NF-κB promoter (BC-3/NF-κB-Luc, BCBL-1/NF-κB-Luc and BC-1/NF-κB-Luc) were treated with increasing concentrations of lenalidomide in μmol/L (Len, μM) and pomalidomide in nmol/L (Pom, nM) or vehicle control (DMSO) for 15 hours and cell lysates were used for the measurement of luciferase activity. The values shown are mean±SE (n=3) FIG. 10C, IMiDs have no effect on interleukin-6 (IL-6) secretion by BC-3 cells. IL-6 level was measured using ELISA in the supernatants of BC-3 cells treated with increasing concentrations of lenalidomide and pomalidomide or vehicle control for 12, 24, and 48 hours. The values shown are mean±SE (n=3). FIG. 10D, Immunoblot analysis showing the effect of IMiDs on the expression levels of IKKα/β, p100/p52, RELB and GAPDH (loading control). FIG. 10E, qRT-PCR analysis showing the levels of indicated mRNA expression in BCBL-1 cells treated with lenalidomide (5 μM) for 24 hours. Real time PCR reactions were carried out in triplicate and the data are presented as fold change in target gene expression. FIG. 10F, Gene set enrichment analysis showing enrichment of gene sets containing target genes of MYC and genes involved in interferon signaling among genes affected by lenalidomide treatment in PEL. NES, normalized enrichment score; q, false discovery rate.

FIG. 11A, Blocking of IFN-α, β and γ did not block the anti-proliferative activity of IMiDs in PEL. BC-3 and BCBL-1 cells were treated with indicated concentrations of IMiDs, IFNs α, and β and their respective blocking antibodies for 5 days. IFN-α blocking antibody (Block Ab) was used at a concentration which blocks 450 units/ml (U/ml) of IFN-α by 50% and IFN-β blocking Ab was used at a concentration which blocks 350 U/ml of IFN-β by 50%. FIG. 11B, BC-3 and BCBL-1 were treated with indicated concentrations of IMiDs, IFN-γ, and IFN-γ blocking antibody for 5 days. IFN-γ blocking antibody (Block Ab) was used at a concentration which blocks 1090 U/ml of IFN-γ by 50%. For both experiments isotype antibody (Iso Ab) corresponding to same species was as used as control. The values shown are mean±SE (n=3).

FIG. 13A, Change in % red fluorescent protein (RFP) positivity over time in BC-1, JSC-1 and DG-75 cells infected with viruses encoding RFP and the indicated shRNAs. The day 2% RFP for each virus was normalized to 1, and subsequent values are expressed relative to cells infected with a virus encoding RFP and a control shRNA. FIG. 13B, BC-1 cells stably expressing tetracycline-inducible H1 promoter (H1/TO)-driven shRNA targeting CRBN (shCRBN) and shRNA targeting scrambled sequence (shCON) were treated with doxycycline (Dox, 500 ng/ml) for 4 days and immunoblotted for the expression of CRBN, GAPDH and TUBA (Tubulin, loading control). The band corresponding to cereblon is marked with an asterisk. FIG. 13C, BC-1 cells stable expressing shCON and shCRBN were treated with doxycycline (Dox, 500 ng/ml) for indicated time points and cell viability was measured by MTS assay. The values shown are mean±SE (n=3). FIG.

13D, BC-1 cells stably expressing shCON and shCRBN were pre-treated with Dox for 3 days followed by treatment with vehicle and IMiDs at indicated concentrations for 5 days in the presence of Dox and cell viability was measured by MTS assay. The values shown are mean±SE (n=3). FIG. 13E, Cell cycle analysis of BC-1 cells stably expressing shCON and shCRBN pre-treated with Dox for 3 days followed by treatment with vehicle and IMiDs at indicated concentrations for 72 hours in the presence of Dox. FIG. 13F, BCBL-1 cells stably transduced with empty retroviral vector, wild type (WT) MYC and MYC T58A mutant were immunoblotted for MYC and TUBA (Tubulin, loading control). FIG. 13G, BCBL-1 cells stably expressing an empty retroviral vector, WT MYC and MYC T58A were treated with increasing concentrations of IMiDs for 4 days and cell viability was measured by MTS assay. The values shown are mean±SE (n=3).

FIG. 14A, BC-3 and BCBL-1 cells were treated with indicated doses of lenalidomide in combination with indicated doses of three structurally different BRD4 inhibitors JQ-1, IBET151 and PFI-1 followed by the calculation of combination index (CI) values using the calcusyn software. Each BRD4 inhibitor was tested in combination with lenalidomide at 12 different combinations. Len (nM): lenalidomide nanomoles/liter; Fa: Fractional effect; CI: Combination Index. FIG. 14B, BCBL-1 cells stably expressing tetracycline-inducible H1 promoter (H1/TO)-driven shRNA targeting BRD4 (shBRD4) and shRNA targeting scrambled sequence (shSCR) were treated with doxycycline (Dox, 500 ng/ml) for 4 days and immunoblotted for the expression of BRD4 and GAPDH. The band corresponding to BRD4 is marked with an asterisk. FIG. 14C, BCBL-1 cells stably expressing shSCR and shBRD4 were treated with Dox for 4 days and cell viability was measured by MTS assay. The values shown are mean±SE (n=3). FIG. 14D, BCBL-1 cells stably expressing shSCR and shBRD4 were treated in the presence/absence of Dox with indicated concentrations of IMiDs or vehicle for 96 hours and cell viability was measured by MTS assay. The values shown are mean±SE (n=3).

FIG. 15A, Body weight gain of mice injected with BC-3 cells followed by indicated treatments (n=7 in each group) over the period of experiment. FIG. 15B, Photograph of mice injected with BC-3 cells followed by treatment with Vehicle, lenalidomide 50 mg/kg b.w. (Len), JQ-1 50 mg/kg b.w. (JQ1) and the lenalidomide+JQ-1 combination (Len+JQ1) on day 28 of treatment. Note the body weight gain of the mice in the vehicle control group which indicates the growth of engrafted BC-3 cells in the peritoneal cavity of the mice. Statistically significant differences are shown by asterisks (*), and (***) at the levels of P≤0.05, and 0.001, respectively.

DETAILED DESCRIPTION OF THE INVENTION

Definitions

Figure 1A:
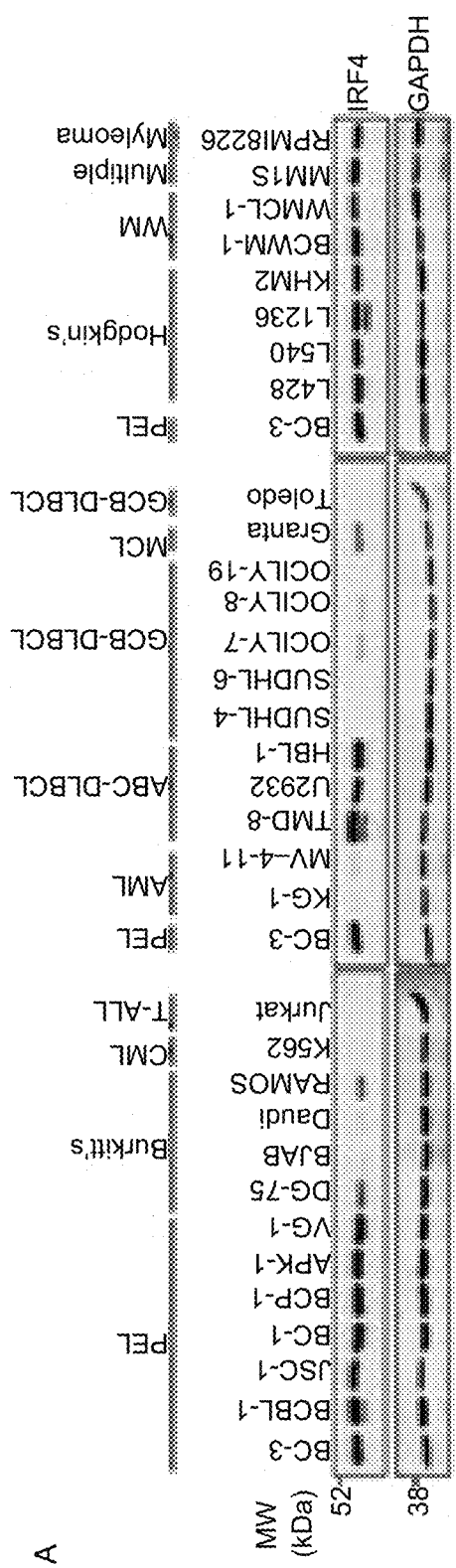
FIGS. 1A-1G. PEL cells express IRF4, knocking down IRF4 is toxic to BC-3 cells, and PEL cells are sensitive to immunomodulatory drugs (IMiDs) lenalidomide and pomalidomide.

As used herein, the term "patient" refers to any animal (e.g., a mammal), including, but not limited to, humans, non-human primates, rodents, and the like, which is to be the recipient of a particular treatment. Preferably the patient is a human.

The term "aliphatic" or "aliphatic group", as used herein, means a straight-chain (i.e., unbranched) or branched, substituted or unsubstituted hydrocarbon chain that is completely saturated or that contains one or more units of unsaturation. Aliphatic groups contain 1-20 aliphatic carbon atoms. Suitable aliphatic groups include, but are not limited to, linear or branched, substituted or unsubstituted alkyl, alkenyl, alkynyl groups.

The term "amine" or "amine group" includes primary, secondary, and tertiary amines having, e.g., the formula N (group)$_3$ wherein each group can independently be H or non-H, such as alkyl, aryl, and the like. Amines include but are not limited to RNH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions.

I. Discussion

IMiDs lenalidomide (Formula I) and pomalidomide (Formula II) are FDA approved compounds for the treatment of multiple myeloma (MM). Both lenalidomide and pomalidomide has been shown to have a predictable and manageable safety profile in MM patients making them a suitable treatment option (Dimopoulos et al., 2013; Richardson et al., 2013). There is no evidence of cumulative toxicity for long-term use, discontinuation rates associated with lenalidomide treatment are low (Dimopoulos et al., 2013).

PEL is a very aggressive malignancy for which no targeted therapy is available at present. IRF4 expression is a unique feature of PEL and knocking down IRF4 is toxic to PEL. Treatment of PEL cells with IMiDs resulted in cell cycle arrest at G1 and decreased the percentage of cells at S phase. We examined the effect of IMiDs on the expression of IRF4 in PEL cells. Our results suggest that IMiDs effectively down regulated the expression of IRF4 and its target MYC which is essential for the survival of PEL (Tolani et al., 2013). Microarray analysis revealed that IMiDs activated IFN pathway in PEL and further treatment of a panel of cell lines with recombinant IFNs show selective cytotoxicity towards PEL but co-treatment of PEL with IFN blocking antibodies did not inhibit the anti-proliferative potential of IMiDs in PEL which suggest that activation of IFN pathway by IMiDs is not responsible for the anti-proliferative potential of IMiDs in PEL.

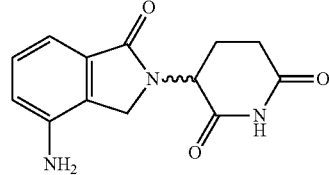

Formula I

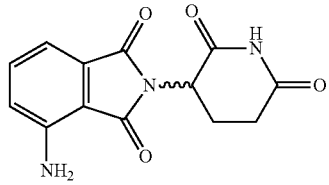

Formula II

Recently, it has been shown that IMiDs selectively degrade the Ikaros family of transcription factors IKZF1 and IKZF3 (Kronke et al., 2014; Lu et al., 2014) in multiple myeloma. But in PEL, IMiDs rapidly degraded only IKZF1 not IKZF3. IKZF1 levels were down-regulated earlier than the down-regulation of IRF4 and MYC. Further IKZF1 specific shRNA is toxic to PEL cells and knocking down IKZF1 down-regulated the expression of IFR4 and MYC. This data not only suggests that IKZF1 is an upstream target of IMiDs, it also suggests that IKZF1 is a potential therapeutic target for the treatment of PEL. IMiDs have no effect on the mRNA expression of IKZF1 but very efficiently down-regulated its protein level suggesting that IMiDs act on IKZF1 post-translationally. Further protein half-life measurements using the protein synthesis inhibitor cycloheximide show that IMiDs efficiently degraded IKZF1. The direct cellular binding target of IMiDs is cereblon (CRBN) (Ito et al., 2010) and binding of IMiDs to CRBN is essential for the immunomodulatory and antiproliferative potential of IMiDs (Lopez-Girona et al., 2012; Zhu et al., 2011). It has been shown that knocking down cereblon is toxic to MM and ABC-DLBCL (Lopez-Girona et al., 2012; Yang et al., 2012; Zhu et al., 2011) in which IMiDs have displayed potent anti-proliferative potential. In contrast, cereblon is dispensable for the survival of PEL but is essential for the antiproliferative potential of IMiDs towards PEL. Our study suggests that MYC is one of the down-stream targets of IMiDs in PEL. Further by interrogating the role of MYC on the activity of IMiDs against PEL, we discovered that down regulation of MYC enhances the anti-PEL effect of IMiDs. Combined treatment with low doses of BRD4 inhibitors (which directly inhibits the transcription of MYC) (Delmore et al., 2011; Mertz et al., 2011; Tolani et al., 2013) with IMiDs displayed an synergistic anti-PEL effect. In summary, we provide strong in vitro and in vivo data showing that IMiDs are effective against PEL and combined treatment of IMiDs with BRD4 inhibitors have synergistic activity against this deadly incurable cancer. When this study was at its final stage a case report was published which shows the successful treatment of an elderly HIV-negative, KSHV-positive PEL patient treated with lenalidomide for 18 months so far without any symptoms or evidence of disease progression (Antar et al., 2014) which supports our preclinical data.

Other suitable immunomodulatory compounds include thalidomide (Formula III) and compounds according to Formulas IV and V.

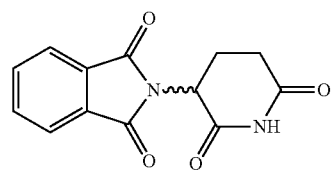

Formula III

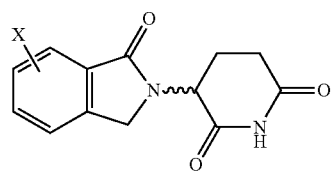

Formula IV

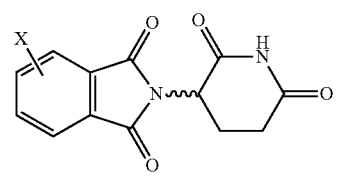

Formula V

X in both Formula IV and Formula V may be independently selected from the group consisting of hydrogen, a halide, an aliphatic group and an amine group.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Pharmaceutically acceptable salts may be obtained using standard procedures well known in the art, for example by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids can also be made.

Formulations and Pharmaceutical Compositions

The compounds related to IMiDs and their derivatives can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The compounds related to IMiDs and their derivatives may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (e.g., glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds related to IMiDs and their derivatives may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known in the art; see for example, Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds related to IMiDs and their derivatives can be determined by comparing their in vitro activity, and in vivo activity in animal models. Methods for the extrapolation of effective dosages in mice, and other animals, to humans are known in the art; see for example, U.S. Pat. No. 4,938,949.

The amount of the compounds related to IMiDs and their derivatives, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to treat PEL may be determined using pharmacological models which are well known to the art, or using the methods described herein below.

II. Experimental Section

A. Material and Methods

Cell Lines and Reagents

BC-3, BCBL-1, JSC-1, BC-1, BCP-1, VG-1 and APK-1 were obtained from Dr. Jae Jung (University of Southern California, CA, USA). DG-75 was obtained from Dr. Alan Epstein (University of Southern California, CA, USA). BJAB, Daudi, RAMOS, K562, and Jurkat were purchased from American type culture collection, Manassas, Va., USA. TMD8, U2932, HBL-1, OCILY-7, OCILY-8 and OCILY-19 cells were obtained from Dr. Art Shaffer (National Institute of Health, MD, USA). SUDHL-4, SUDHL-6, Granta, Toledo, KG-1 and MV-4-11 cells were obtained from Randall Rossi (University of Rochester School of Medicine, NY, USA). L428, L540, L1236 and KMH2 cells were obtained from Dr. Markus Mapara (Columbia University Medical Center, NY, USA) BCWM-1 and WMCL-1 cells were obtained from Dr. Irene Ghobrial (Dana Farber Cancer Institute (DFCI), Harvard Medical School, MA, USA). MM1S and RPMI8226 cells were kind gift from Dr. Alan Lichenstein (Veterans affairs hospital, Los Angeles, Calif., USA). All the above mentioned cells were grown in RPMI medium supplemented with 20% (v/v) fetal bovine serum, 100 units/ml penicillin, 100 µg/ml streptomycin, 2 mM glutamine. HEK-293FT cells (Invitrogen) were grown in Dulbecco's modified Eagle's medium supplemented with 10% (v/v) fetal bovine serum. The cells were maintained at 37° C. and 5% $CO_2$. After the cell lines were received they were expanded and multiple vials were frozen in liquid nitrogen. None of the cell lines used in this study was cultured for longer than 3 months continuously. After 3 months a new frozen vial was thawed and used for experiments. No further authentication of cell lines characteristics was done. Reagents were obtained from the following sources: Lenalidomide (S1029 and 100500) from Selleck chemicals, Houston, Tex., USA and Medkoo biosciences, Chapel Hill, N.C., USA; Pomalidomide (S1567) from Selleck chemicals, Thalidomide (0652) from Tocris Biosciences, Bristol, UK; JQ-1, a kind gift from Dr. James Bradner, DFCI, Harvard University, MA, USA; IBET151 (CT-BET151) from Chemietek, Indianapolis, Ind., USA; MLN4924 (A-1139) from Active Biochem, Maplewood, N.Y., USA; Phenazine methosulfate (P9625); Dimethyl sulfoxide (D2650); PFI-1 (SML0352), Doxycycline (D9891), Hoechst 33342 (B2261), Propidium iodide (P4170), Interferon-α (14276), Interferon-γ (13265), and Cycloheximide (01810) from Sigma-Aldrich, St. Louis, Mo., USA. Interferon-β (300-02132) from Peprotech, Rocky Hill, N.J., USA. Rabbit polyclonal blocking antibodies to interferon α, β, and γ (31101, 31410, and 31500) from PBL biomedicals, Piscataway, N.J., USA. Normal Rabbit IgG (2027) from Santa Cruz Biotechnology (SCBT), Santa Cruz, Calif., USA. Mouse monoclonal blocking antibody for IFNAR1/2 (21385) from PBL biomedicals and isotype control normal mouse IgG (3878) from SCBT.

Retroviral and Lentiviral Constructs

Retroviral constructs containing c-Myc-T58A and Flag epitope-tagged, wild-type c-Myc were obtained from Addgene (Cambridge, Mass., USA). Recombinant retroviruses were generated and used to infect PEL cell lines and positive clones were selected with puromycin. For generation of shRNA encoding lentiviral vectors, shRNA oligonucleotides directed against human IRF4, MYC and BRD4 mRNAs were annealed and cloned into a modified pENT entry vector containing a tetracycline-inducible H1 promoter (H1/TO). The cassette containing the H1/TO promoter along with the shRNA hairpin was concatenated as described earlier (Zhu et al., 2007) so as to result in eight copies of the H1/TO-shRNA cassettes in each vector. Recombination-based subcloning was used to transfer the concatenated H1/TO-shRNA cassettes into a pSLIK destination vector (Shin et al., 2006) Lentiviral shRNAs for control and CRBN (shCRBN-2, ligated to pLKO-tet-on-puro) were obtained from Dr. Willian G Kaelin Jr. (DFCI, Harvard University, MA, USA). Lentiviral shRNAs for control, IKZF1-1, and IKZF1-2 (ligated to pLKO-RFP) were also obtained from Dr. Willain G Kaelin Jr. 293FT cells were used to induce virus production as described previously (Zhu et al., 2007). The packaged virus was then used to infect PEL cells and positive clones were selected with G418 (pslik vector), puromycin (pLKO vector). Doxycycline (500 ng/ml) was used to induce the expression of shRNAs with tetracycline inducible promoter.

Cell Viability

Cells from exponentially growing cultures were plated in untreated flat-bottom 96 well plates at a density of $5 \times 10^3$ cells/well, treated with an increasing concentration of the drugs and subsequently assessed for cell viability using the MTS reagent (3-4,5-dimethylthiazol-2yl)-5-(3-carboxymethoxyphenyl)-2-(4-sulfophenyl)-2H-tetrazolium, inner salt) following the manufacturer's instructions (Promega). Percent cell survival was calculated based on the reading of cells grown in the presence of DMSO control. Experiments were performed in triplicate and have been repeated 2-3 times.

Cell Cycle and Apoptosis Analysis

DNA content analysis was performed as described earlier (Yang et al., 2011). Samples were analyzed by flow cytometer (BD FACSVerse) and the resulting data analyzed by ModFit LT software. Apoptosis was analyzed using BD AnnexinV-FITC apoptosis detection kit I as per manufacturer instructions. Samples were analyzed by flow cytometer (BD FACSVerse) and the resulting data analyzed by FlowJo software.

Preparation of Cell Lysates, Western Blotting and Antibodies

Cells were lysed in lysis buffer containing 20 mM sodium phosphate (pH 7.4), 150 mM NaCl, 0.1% Triton X-100, 0.2 M PMSF, and 10% glycerol supplement with a protease inhibitor mixture tablet (Roche). Whole cell extracts were resolved by SD-polyacrylamide gel electrophoresis, transferred to nitrocellulose membrane, and probed with the indicated primary antibodies. Bound antibodies were detected with IRdye 680 or 800 (Licor biosciences) and blots were scanned with licor odyssey CLx imaging system (Licor biosciences). Primary antibodies used in these experiments were from the following sources: PARP (9542), NF-κB2 (p100/p52; 4882) from Cell Signaling; IRF4 (6059), IKZF1 (13039), HSP90 (69703), IKKα/β (7607), RELB (226) from Santa Cruz Biotechnology; MYC (1472-1, Epitomics); tubulin (T9026), cereblon (HPA045910) from Sigma; GAPDH (1107018, Ambion), IKZF3 (6255, Imgenex) and BRD4 (a gift from Dr. Peter Howley, Harvard Medical School).

Luciferase Assay and IL-6 Elisa

BC-3 NF-κB Luc, BCBL-1-NF-κB Luc and BC-1-NF-κB Luc cells were treated with increasing concentrations of lenalidomide and pomalidomide for 15 h and the cells were lysed to assay the firefly luciferase activity as described earlier (Chaudhary et al., 1999). IL-6 was measured in supernatants using BD OptEIA™ Human IL-6 ELISA set as per manufacturer's instructions.

Small Hairpin RNA (shRNA) Depletion Assay for IKZF1

BC-3, BCBL-1, BC-1, JSC-1 and DG-75 cells were infected with pLKO-RFP lentiviral vectors expressing control shRNA or shRNAs against IKZF1. Two days later the percentage of RFP+ cells was monitored using flow cytometer (BD FACSVerse). The change of RFP+ percentage for each shRNA was first normalized against day 2. Then, the relative percentage of RFP+ cells was normalized against shRNA control for each time point as indicated.

Microarray and Gene Set Enrichment Analysis (GseaPreranked)

BC-3 and BCBL1 were treated with 5 µM lenalidomide for 24 h and then harvested to extract total RNA using the RNeasy Mini Kit (Qiagen). Two technical replicates per cell line per condition (8 samples total) were assayed on the Illumina Human HT12 BeadChip whole genome expression microarray, with coverage of 39809 coding transcripts and 3961 non-coding transcripts. Probe intensities were extracted directly from binary IDAT files using the 'illuminaio' package (Smith et al., 2013). Background correction and normalization was then performed using 'limma' package (Smyth, 2005). An estimate of the fraction of probes with detectable expression (approximately 47% of the probes present on the array) was extracted by comparing the negative control probe intensities with hybridization probe intensities; probes failing this cutoff were filtered from further analysis. An empirical Bayes linear model including treatment and cell-line specific effects was fitted to the filtered data, again using 'limma'. We retained 992 transcripts whose expression changed significantly with treatment ($p_{FDR}$<0.05) across cell lines. Hierarchial clustering with Euclidean distance and centroid linkage was performed in R (http://www.R-project.org). A heat map of differences (corrected for cell-line-specific effects) was plotted. Non-parametric gene set enrichment analysis, pre-ranked by log-fold-change (GSEApreranked) was performed using GSEA 2.1.0 (Broad Institute, Cambridge, Mass.) using the same 992 transcripts previously found to be significantly perturbed by lenalidomide treatment. Notable results from the GSEA analysis are presented in FIG. 2d and FIG. 10E.

Real-Time RT-PCR

PEL cells treated with their respective treatments were harvested to extract total RNA using the RNeasy mini kit (Qiagen) and cDNA was synthesized using reverse transcriptase enzyme Superscript II (Invitrogen). Real-time quantitative reverse transcript-polymerase chain reaction (qRT-PCR) was performed with SYBR Green using gene-specific PCR primers. Samples were run in triplicate, and PCR was performed by an ABI Step One Plus thermocycler (Applied Biosystems). GAPDH was used as housekeeping gene and qRT-PCR data (Ct values) was analyzed using the $2^{-\Delta\Delta CT}$ method as described earlier (Zhao et al., 2007). The qRT-PCR data was presented as fold change in target gene expression±standard error.

PEL Orthotopic Tumor Model

A total of $2\times10^7$ BC-3 cells were injected intraperitoneally into female NOD.SCID mice (NCI Frederick, 6 weeks old). 5 days after tumor cells inoculation the mice were randomly divided in to 4 groups (n=7 each). Vehicle control (10% Hydroxypropyl beta cyclodextrin), lenalidomide 50 mg/kg b.w. (once daily), JQ-1 50 mg/kg b.w. (once daily) and the combination were administered intraperitoneally daily for 28 days. Then the animals were monitored for survival. Body weight gain was measured once in 3 days as a surrogate measure of tumor progression (Qin et al., 2014). The experiments were performed following the guidelines of institutional animal ethics committee.

Statistical Analysis

Two-tailed unpaired Student's t test was used to test for differences between two groups.

Differences with a p value ≤0.05 were considered statistically significant.

B. Examples

Example I

PEL Cell Lines Express IRF4 and Knocking Down IRF4 is Toxic to them

Figure 1C:
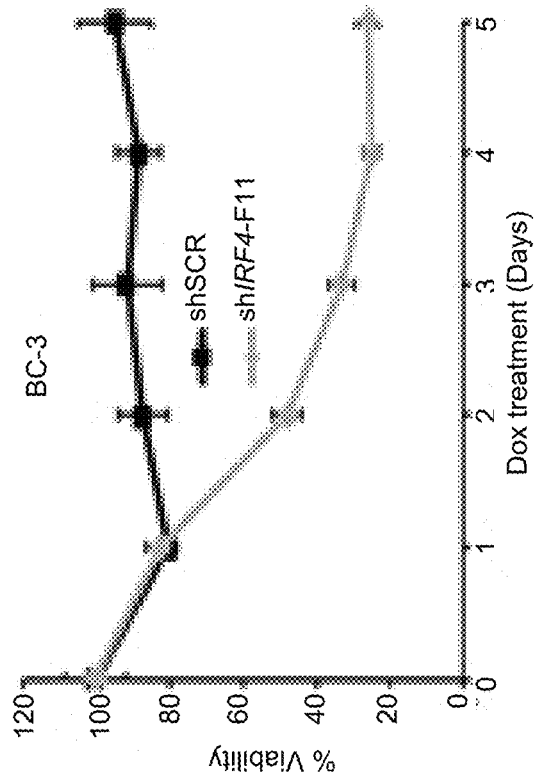
Figure 1B:
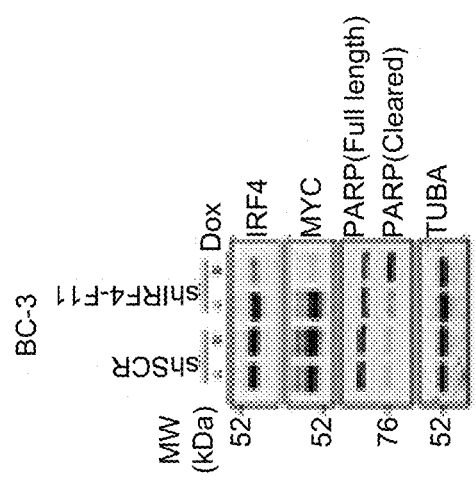
Figure 1D:
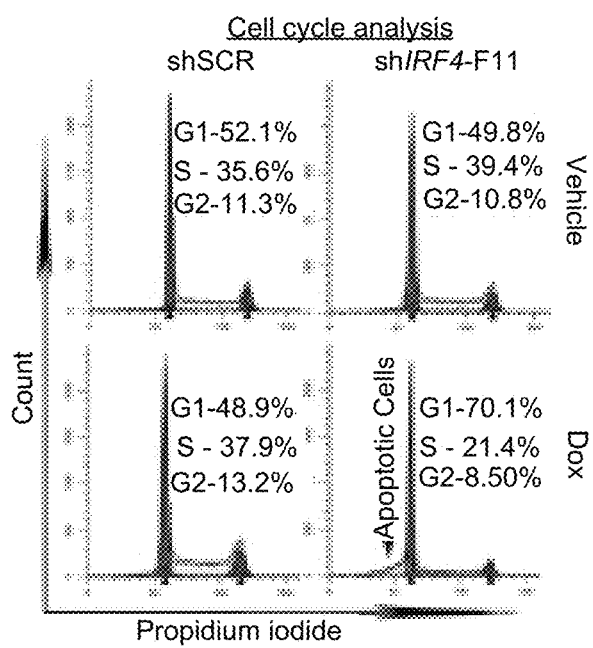
Figure 1E:
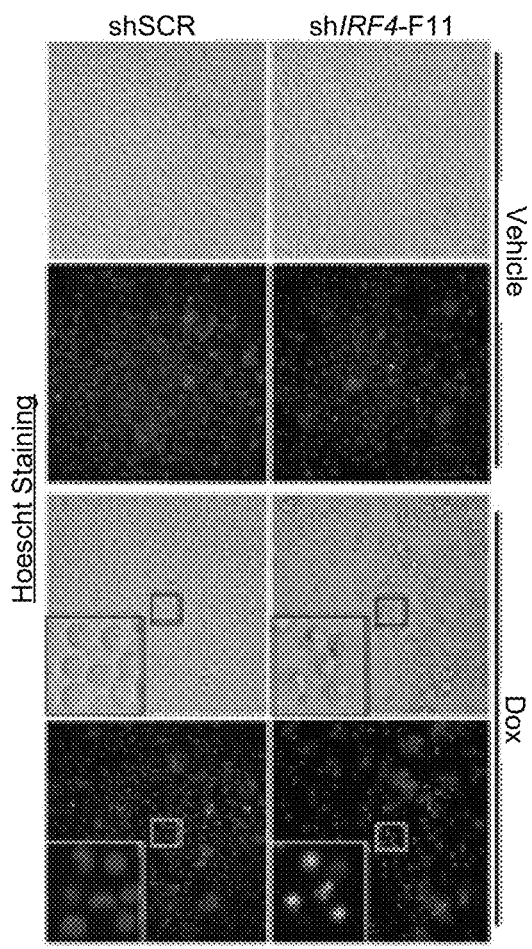
Figure 1F:
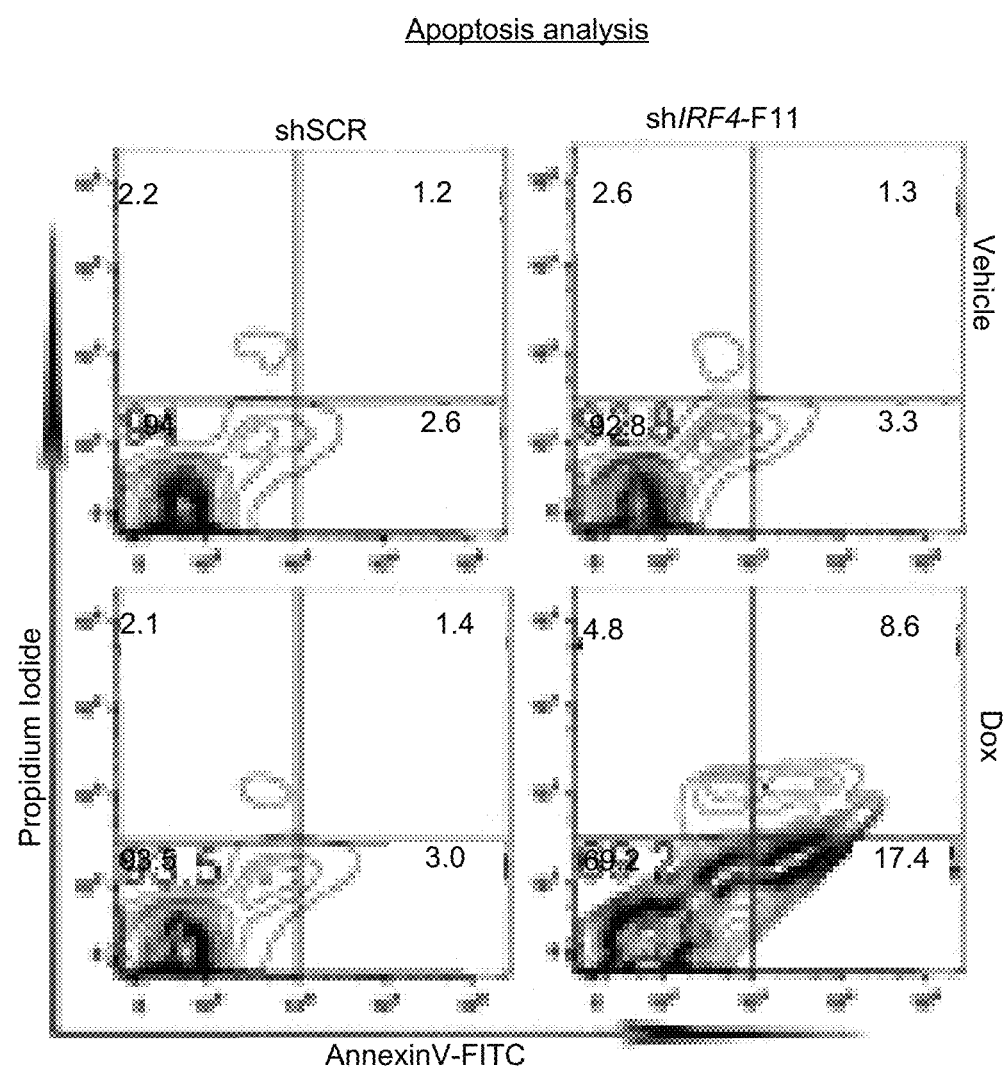
Figure 8B:
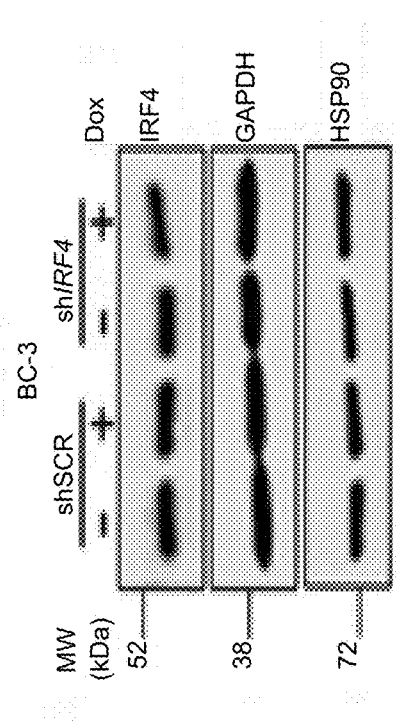
FIGS. 8A-8D. IRF4 is essential for the survival of BC-3 cells.
Figure 8A:
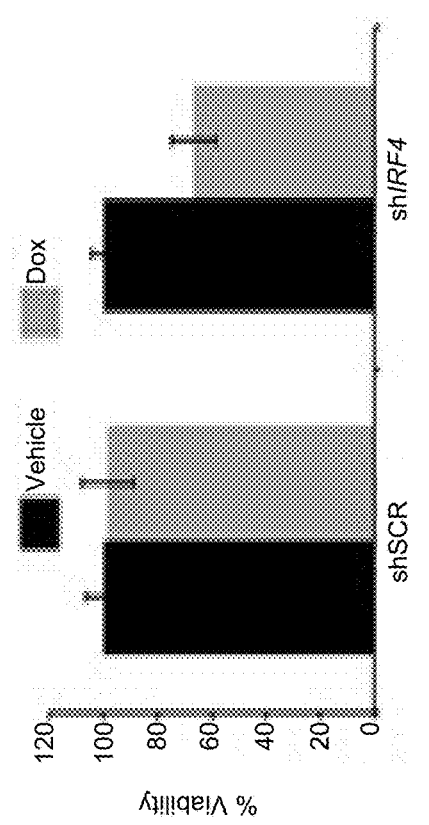
Figure 8C:
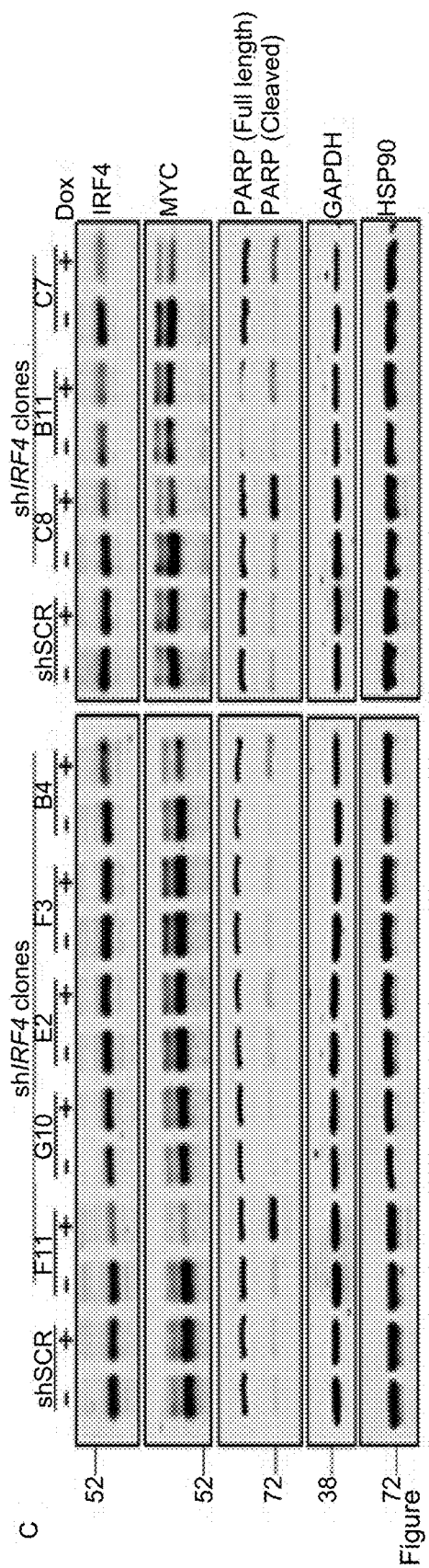
Figure 8D:
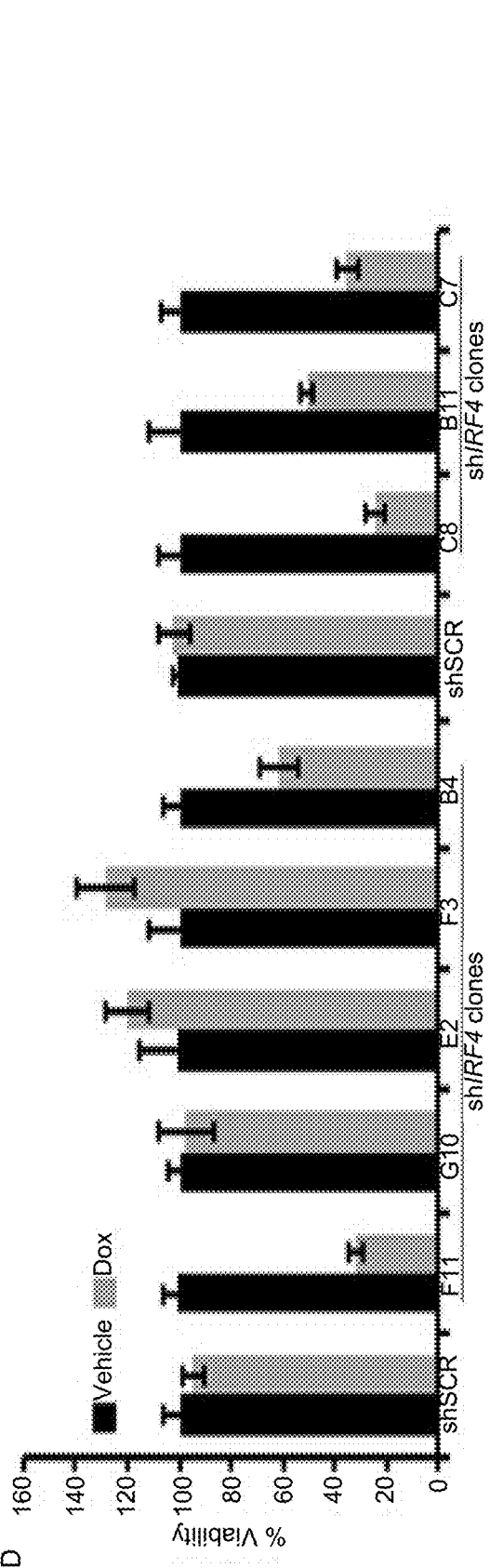

IRF4 expression is associated with many lymphoid malignancies (Shaffer et al., 2009). Examination of IRF4 expression in a panel of 33 cell lines comprising 11 hematological malignancies (FIG. 1A) suggested that 100% of PEL express IRF4. Next, we tested effect of IRF4 knockdown in BC-3 cells by IRF4 specific shRNA. For this purpose we have generated a stable BC-3 cells expressing tetracycline-inducible-H1(TO/H1) promoter driven shRNA targeting IRF4 (shIRF4). Treatment of BC-3 cells stably expressing shIRF4 with doxycycline (Dox) resulted only in a slight down-regulation of IRF4 in this polyclonal population of cells (FIG. 8A) but there was a significant decrease (30%) in cell proliferation upon Dox treatment in these cells (FIG. 8B). Therefore to better understand the role of IRF4 in the survival of BC-3 cells, we generated single cell clones of BC-3 cells stably expressing shIRF4 by limiting dilution. Treatment of these clones with Dox resulted in varied levels of down regulation of IRF4 with significant down regulation observed in clones F11, B4, C8, B11 and C7 (FIG. 1B and FIG. 8C). In contrast, Dox treatment had no significant effect on IRF4 levels in clones G10, E2 and F3 (FIG. 8C). MYC, a target of IRF4 (Shaffer et al., 2008) was down regulated only in clones F11, B4, C8 and C7 upon Dox treatment and cleavage of PARP was also observed only in clones F11, B4, C8, B11 and C7 in which IRF4 is downregulated upon Dox treatment (FIG. 1B and FIG. 8C). In contrast, Dox treatment had no effect on the levels of MYC and PARP cleavage in clones G10, E2 and F3 (FIG. 8C). More importantly, Dox treatment in BC-3 cells stably expressing shIRF4 clones F11, B4, C8, B11 and C7 were accompanied by approximately 63%, 38%, 75%, 56% and 65% reduction in cellular proliferation, respectively. Whereas, no significant effect on cellular proliferation were observed in clones G10, E2, F3, and BC-3 cells stably expressing TO/H1 promoter driven sRNA targeting a scrambled sequence (shSCR, FIG. 8C). Dox treatment of BC-3 cells stably expressing shIRF4, clone F11(shIRF4-F11) resulted in decreased cellular proliferation as early as day 2, whereas no significant effect on cellular proliferation was observed in BC-3 cells stably expressing shSCR over time (FIG. 1C). Treatment of BC-3 cells stably expressing shIRF4-F11 with Dox resulted in G1 arrest as observed by a marked increase in the number of cells in the G1 phase with concurrent decrease in cells in the S phase (FIG. 1D). Dox treatment of BC-3 cells stably expressing shIRF4-F11 resulted in appearance of cells with condensed and fragmented nuclei suggestive of apoptosis (FIG. 1E), which was confirmed by staining with annexinV/propidium iodide (FIG. 1F). In contrast, no significant effects were observed in BC-3 cells stably expressing shSCR upon treatment with Dox in cell cycle and apoptosis analysis (FIG. 1D-F). Collectively, the above results suggest that down-regulation of IRF4 is toxic to BC-3 cells by inhibiting cell cycle progression and by induction of apoptosis.

Example II

IMiDs Show Selective Cytotoxicity Towards PEL

Figure 1G:
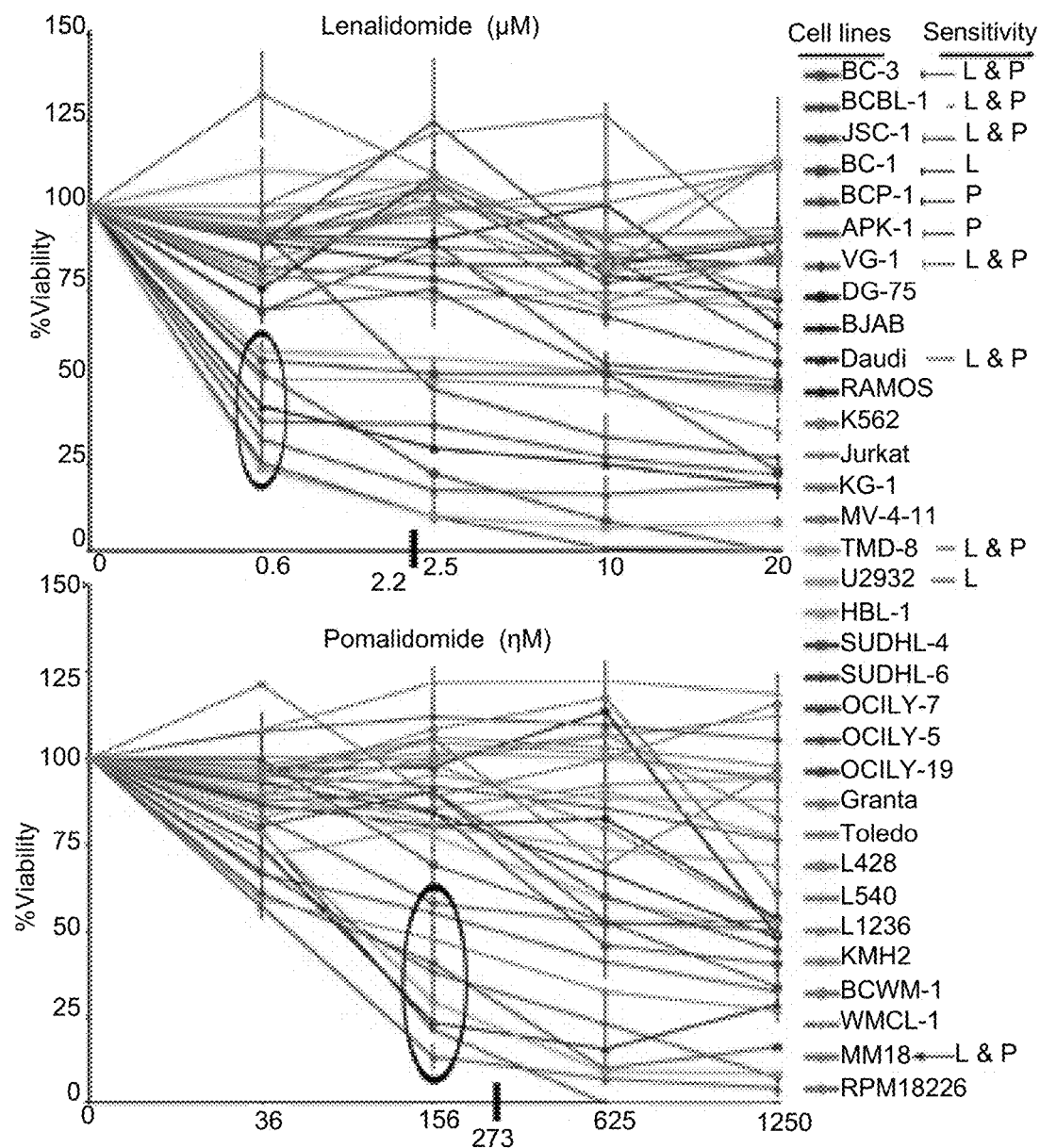
Figure 9:
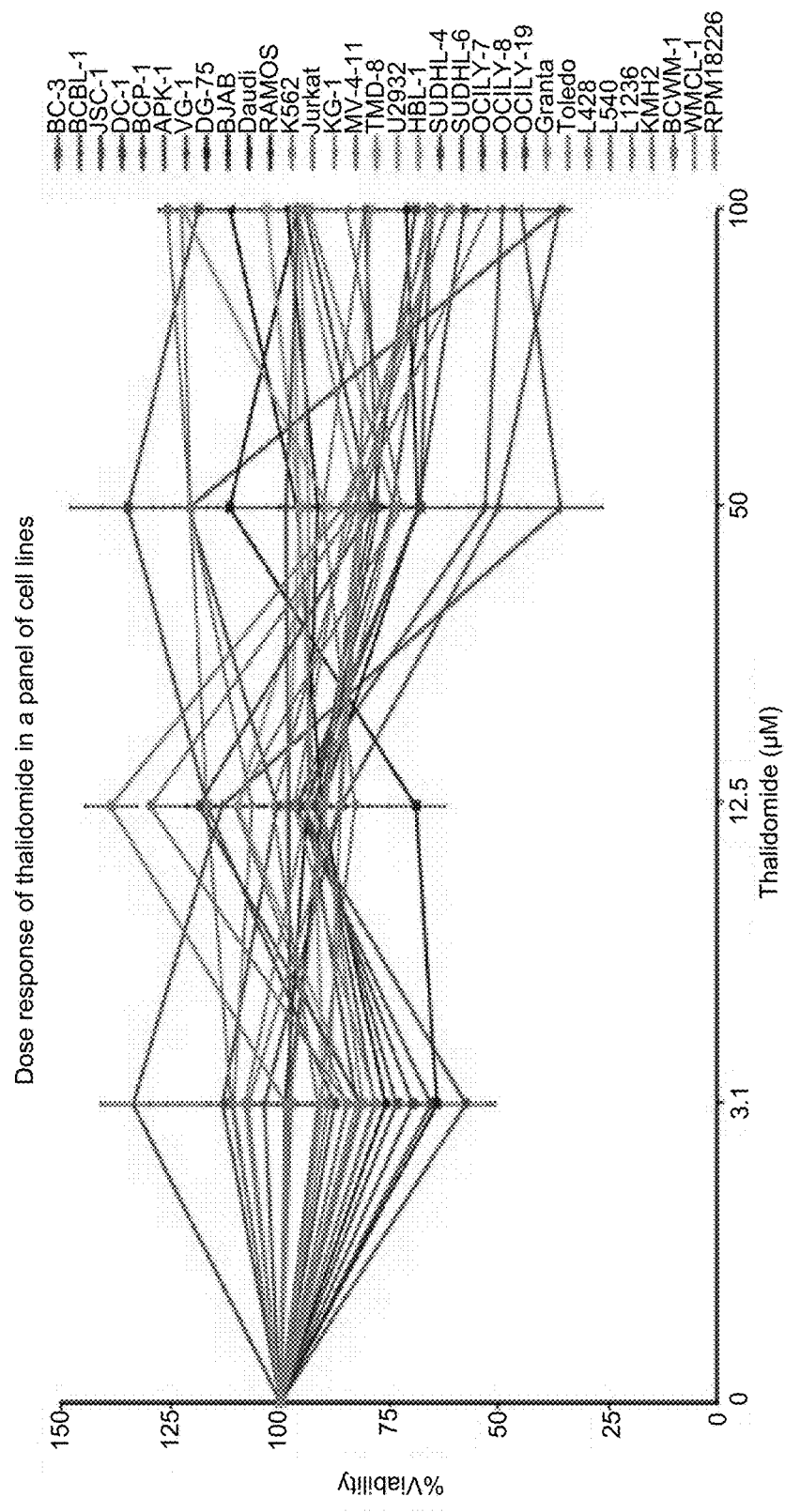
FIG. 9. Effect of thalidomide in a panel of hematological cancer cell lines. Indicated panel of cell lines were treated with increasing concentrations of thalidomide in μmol/L (μM) for 5 days, and cell viability was measured using an MTS assay. The values shown are mean±SE (n=3).

It has been recently shown that IRF4 can be targeted by IMiDs lenalidomide and pomalidomide (Lopez-Girona et al., 2011; Yang et al., 2012). Next, we treated a panel of logarithmically growing cell lines for 5 days with increasing concentrations of thalidomide, lenalidomide and pomalidomide. In this experiment 5/7 and 6/7 PEL cell lines were sensitive to lenalidomide and pomalidomide, respectively within their physiologically achievable doses (Chen et al., 2007; D'Amato et al., 2013) observed in clinical trials (FIG. 1G). MM1S (multiple myeloma), TMD8 (ABC-DLBCL) and Daudi (Burkitt's lymphoma) were also sensitive to IMiDs thus serving as positive controls (FIG. 1G). Thalidomide did not have any major effect on the growth of these cell lines (FIG. 9). This absence of in vitro activity of thalidomide has been previously reported, suggesting a requirement for in vivo metabolism for its proper function (Zhu et al., 2011).

Example III

IMiDs Downregulate the Expression of IRF4, MYC and Induce Cell Cycle Arrest

Figure 2A:
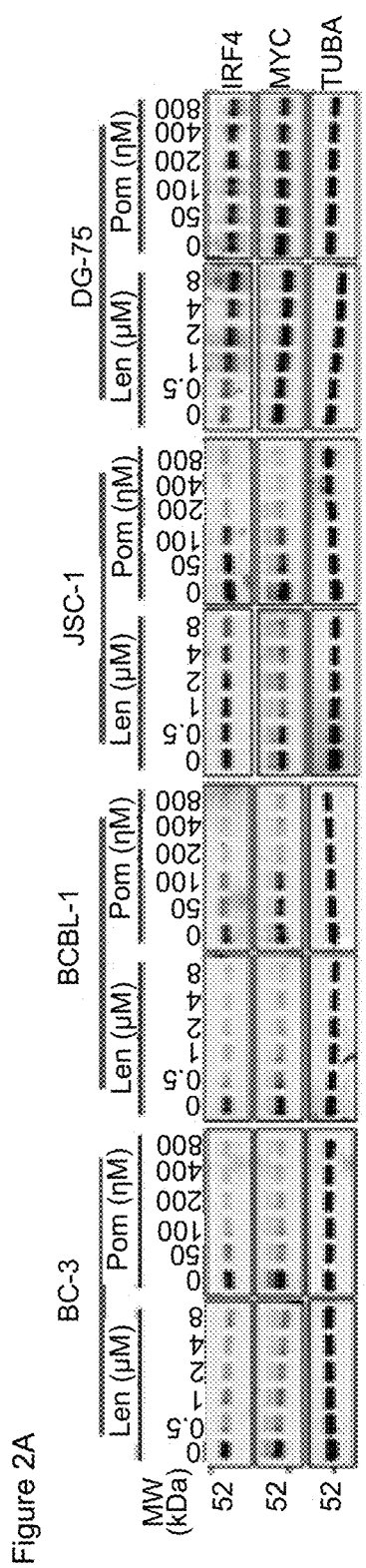
FIGS. 2A-2E. IMiDs lenalidomide (Len) and pomalidomide (Pom) downregulate the expression of IRF4, MYC and induced cell cycle arrest in PEL cells.
Figure 2B:
Figure 10A:
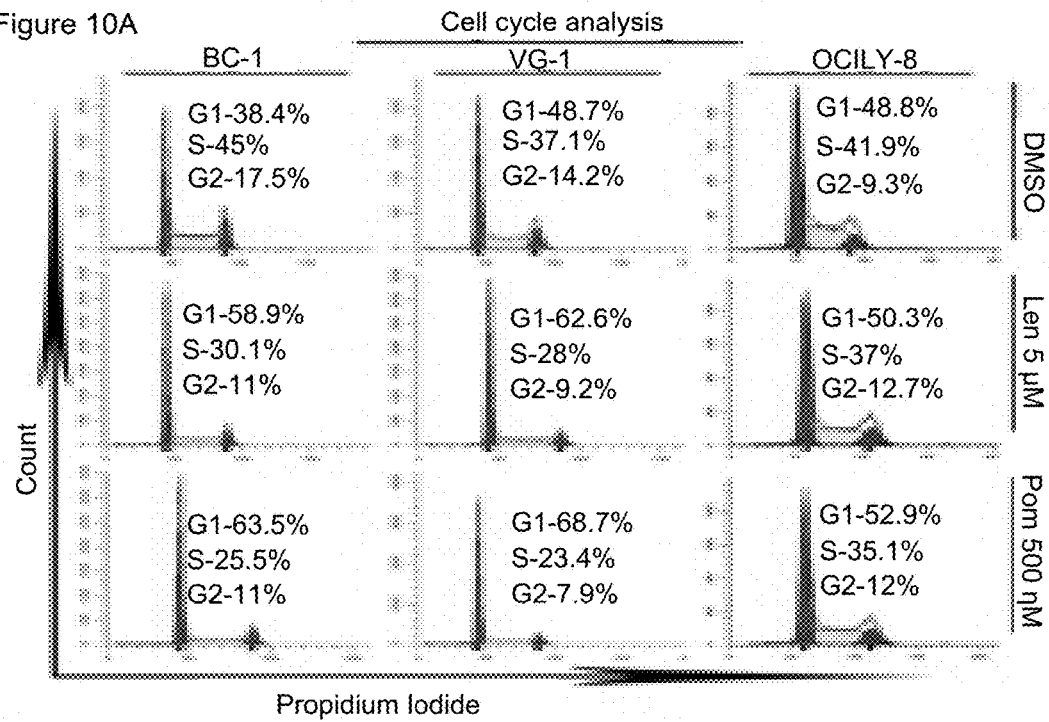

To test whether IMiDs downregulate the expression of IRF4 and its target MYC. PEL cells were treated with increasing concentrations of IMiDs for 48 h followed by western blotting detection of IRF4 and MYC. Treatment of BC-3, BCBL-1 and JSC-1 with IMiDs resulted in decreased expressions of IRF4 and MYC (FIG. 2A). In contrast, IMiDs have no significant effect on the levels of IRF4 and MYC in DG-75 cells (FIG. 2A). Further, treatment of PEL cells with IMiDs resulted in G1 arrest as observed by a marked increase in number of cells in G1 phase with concurrent decrease in cells in the S phase (FIG. 2B and FIG. 10A). Whereas, IMiDs have no major effect on cell-cycle progression in DG-75, and OCILY-8 cells (FIG. 2B and FIG. 10A).

Example IV

IMiDs have No Effect on the Constitutive NF-κB Activity Present in PEL

Figure 10B:
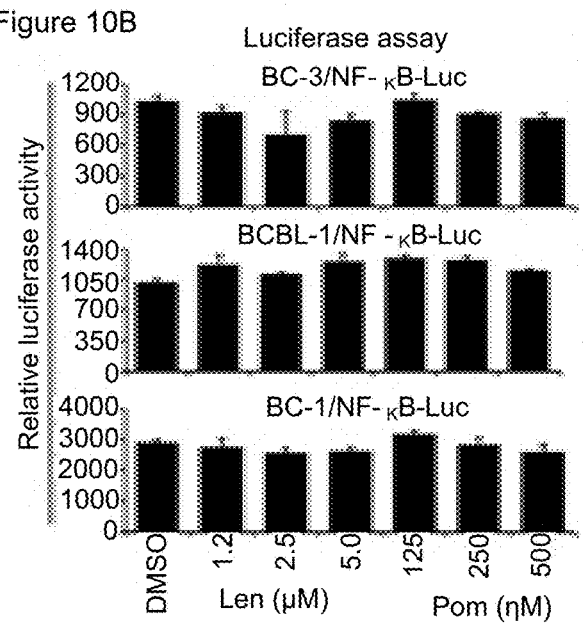
Figure 10C:
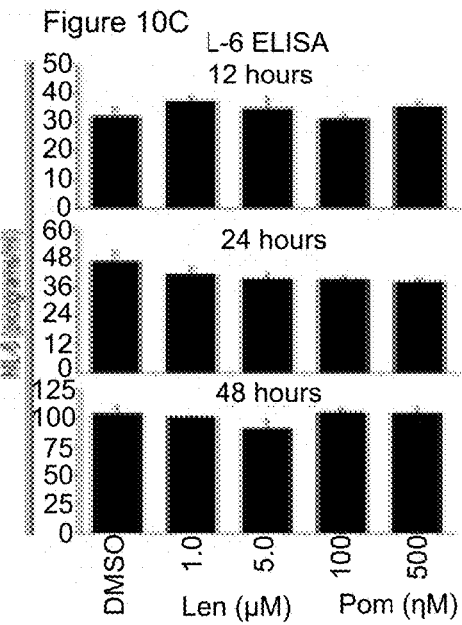
Figure 10D:
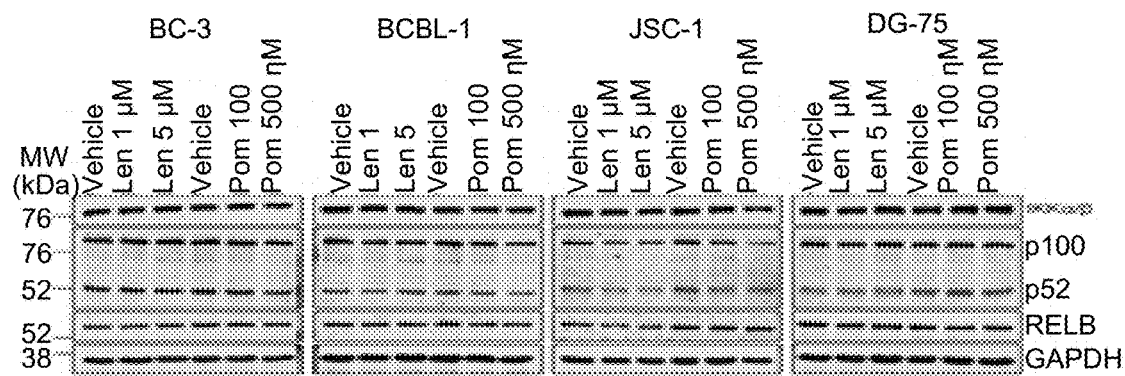

PEL cells have constitutive NF-κB activity due to the presence of KSHV viral proteins (Gopalakrishnan et al., 2013; Guasparri et al., 2004; Keller et al., 2000; Yang et al., 2011) and aberrant NF-κB activity has been shown to up regulate the expression of IRF4 (Shaffer et al., 2009). To test whether IMiDs repress IRF4 expression by inhibiting NF-κB pathway, we took advantage of BC-3, BCBL-1, and BC-1 cells engineered to express a stably integrated copy of an NF-κB-driven luciferase reporter construct (NF-κB-Luc). IMiDs treatment did not have any effect on NF-κB-Luc activity (FIG. 10B) thus suggesting that IRF4 down-regulation by IMiDs does not involve NF-kB. Further to completely rule out the role of NF-κB in lenalidomide activity in PEL, BC-3 cells were treated with lenalidomide for 12, 24 and 48 h and cell free supernatants were used to measure IL-6 (a direct NF-κB target gene)(Libermann and Baltimore, 1990). Lenalidomide treatment did not have any significant effect on IL-6 secretion by BC-3 cells (FIG. 10C) and also increasing doses of lenalidomide did not have any significant effect on the expression of NF-κB proteins IKKα/β, p100/p52 and RELB proteins in BC-3, BCBL-1, JSC-1 and DG-75 cells (FIG. 10D). These results clearly show that IMiDs have no significant effect on the constitutive NF-κB pathway present in PEL cells.

Example V

Figure 2C:
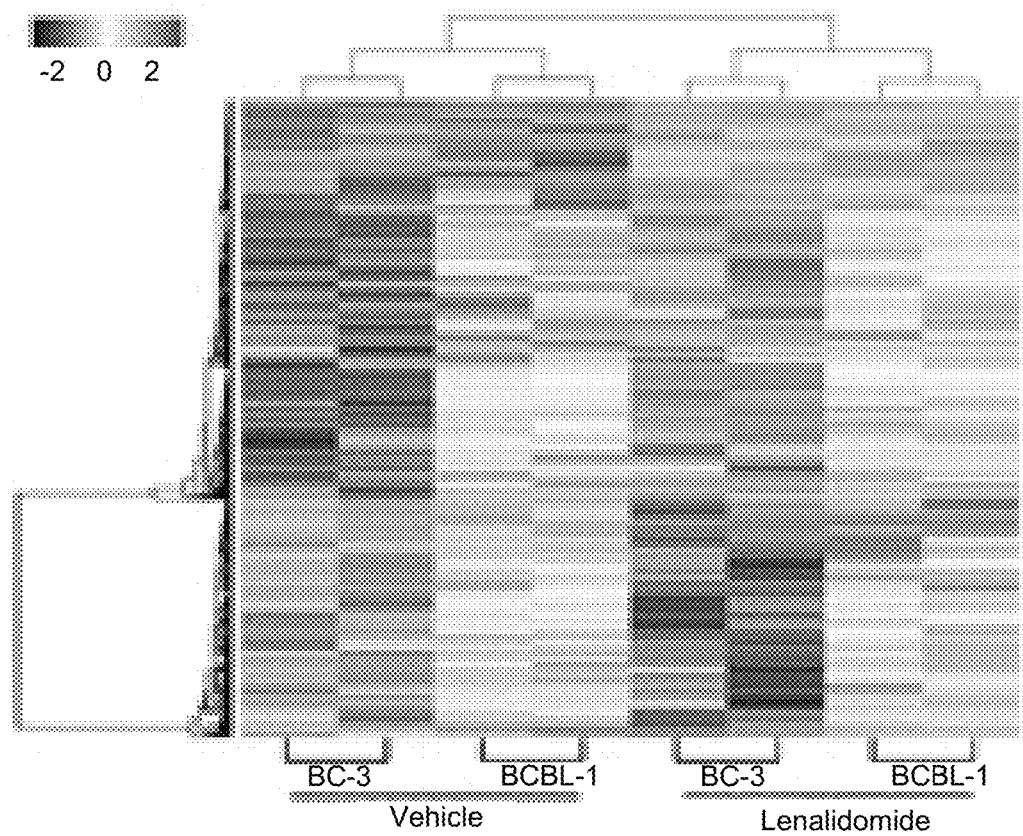
Figure 2D:
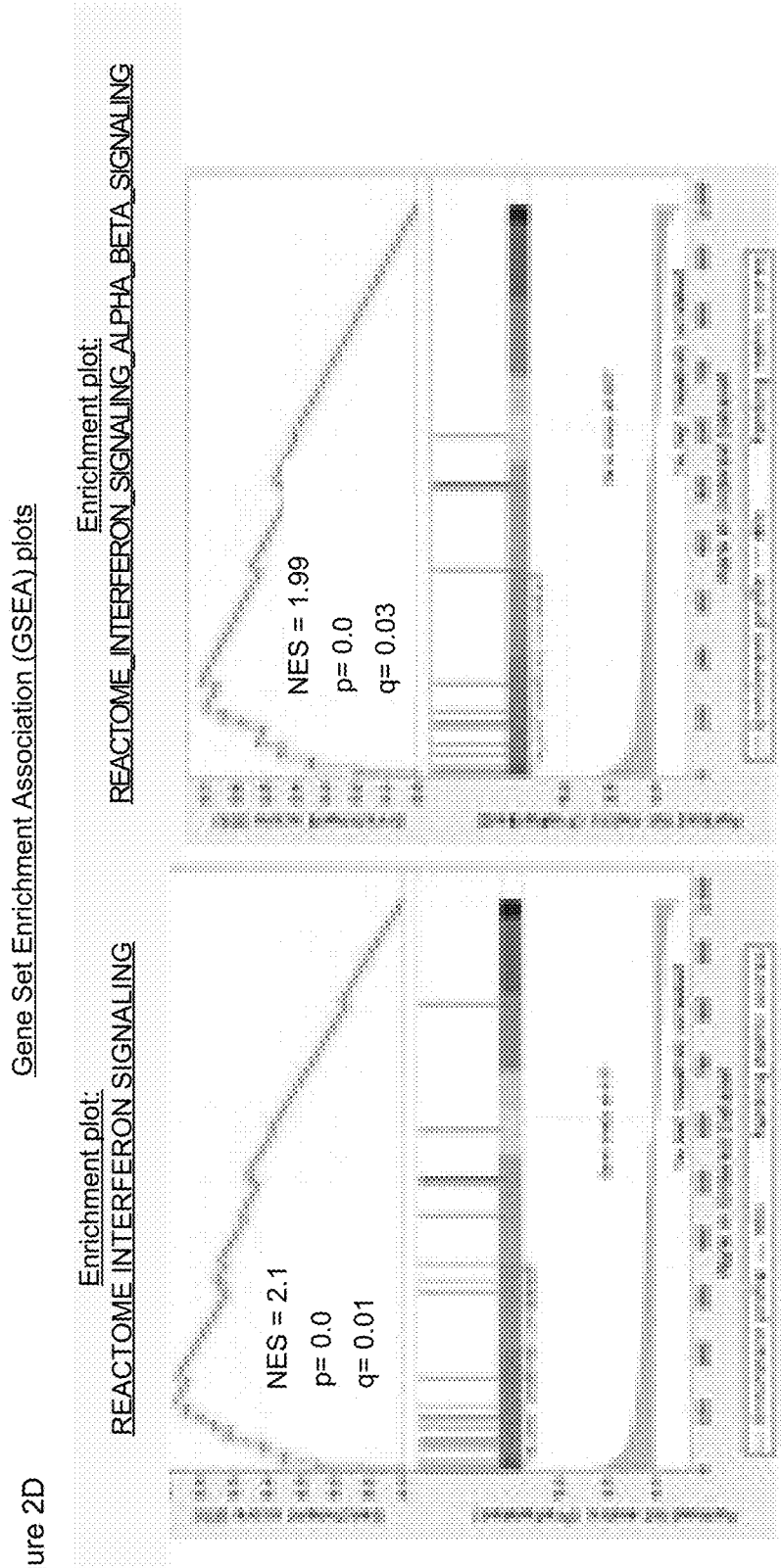
Figure 10E:
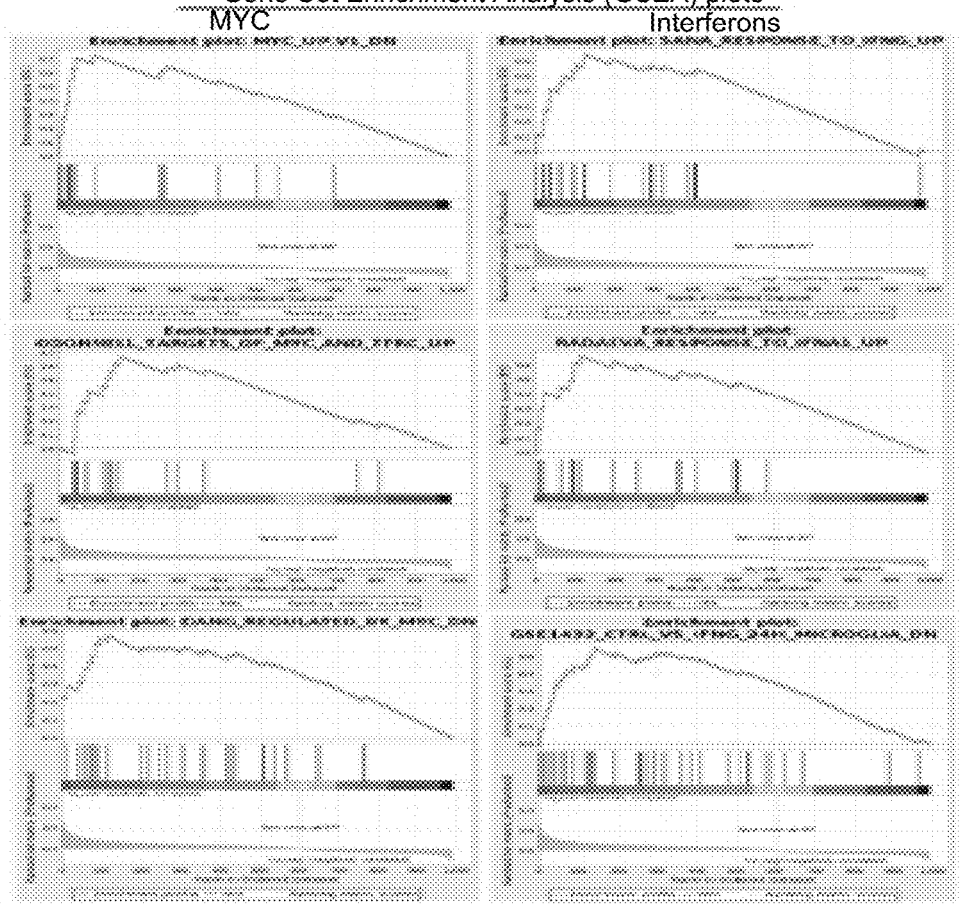

GSEA Analysis Identified Activation of Interferon Signaling in PEL by Lenalidomide To test the effect of lenalidomide on gene transcription, BC-3 and BCBL-1 cells were treated with lenalidomide (5 μM) for 24 h followed by genome-wide microarray analysis using Illumina's platform. Unsupervised hierarchical clustering separated samples according to their treatment group, indicating a common transcriptional response to treatment with lenalidomide (FIG. 2C). Rather than inducing nonspecific changes in gene expression, lenalidomide induced significant changes in a limited number of genes. Thus, there were 992 genes (390 down- and 602 upregulated genes) whose expression were changed significantly ($p_{FDR}$<0.05) in both the cell lines. We used a Gene Set Enrichment Analysis (GSEA) program to identify functional gene sets whose expression changed significantly with lenalidomide treatment in PEL cells (Subramanian et al., 2005). Among the gene signatures identified by this analysis were gene sets containing genes that are known targets of interferons and Myc (FIG. 2D and FIG. 10E).

Example VI

Interferons α, β & γ are Efficacious Against PEL

Figure 2E:
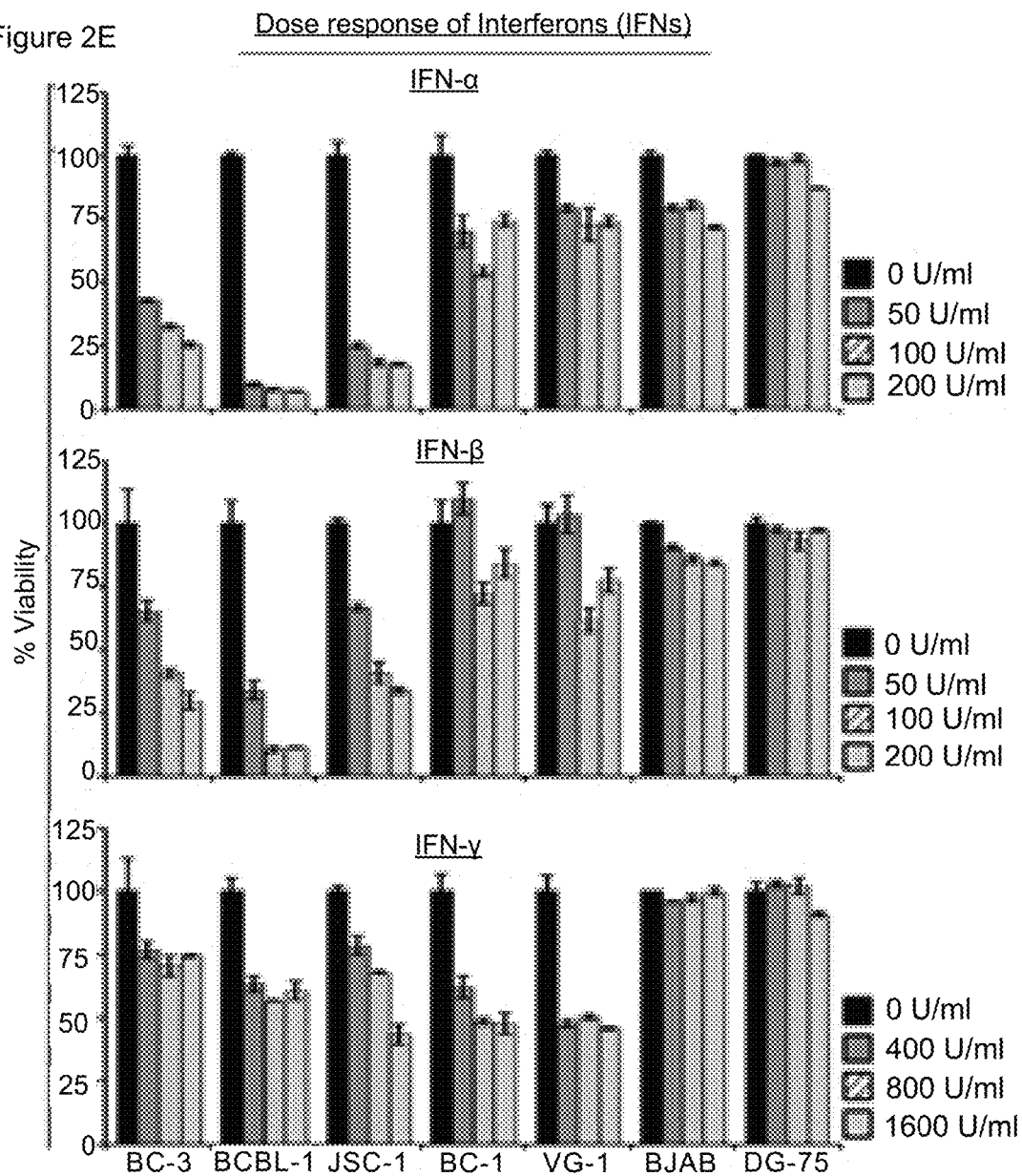

GSEA analysis identified activation of interferon (IFN) signaling in PEL upon treatment with lenalidomide. Indeed, BCBL-1 cells treated with lenalidomide upregulated the transcript levels of IFNs and interferon specific genes (ISGs) significantly (FIG. 10F). If, IMiDs display its antiproliferative activity in PEL by activating the IFN pathway then treatment of PEL with recombinant IFNs (rIFNs) will mimic the effect of IMiDs. To test this hypothesis we treated a panel of cell lines with increasing concentrations of rIFNs α, β and γ. All the 5 PEL cell lines (BC-3, BCBL-1, JSC-1, BC-1 and VG-1) were sensitive to recombinant IFNs α, β and γ (FIG. 2E) with BC-3, BCBL-1 and JSC-1 being highly sensitive for IFNs α and β. In contrast, one of the IMiDs resistant cell line DG-75 had no effect with IFNs at the tested concentrations and the other IMiDs resistant cell line BJAB had a very little effect with IFNs α and β and without any significant effect with IFN-γ (FIG. 2E). These results clearly show that PEL cells which are sensitive to IMiDs also respond to rIFNs treatment whereas, cells which are resistant to IMiDs did not respond well to rIFNs treatment (BJAB and DG-75).

Example VII

Figure 11A:
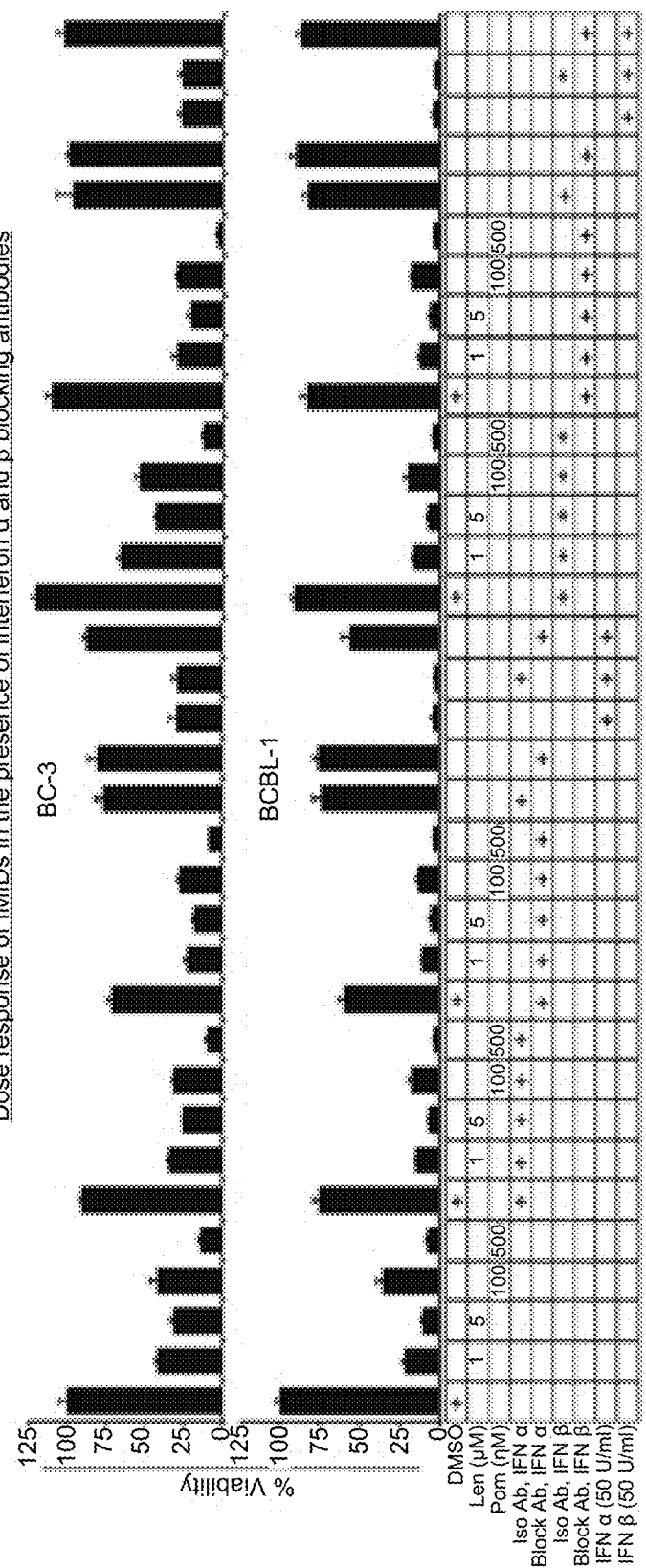
FIGS. 11A-11B.
Figure 11B:
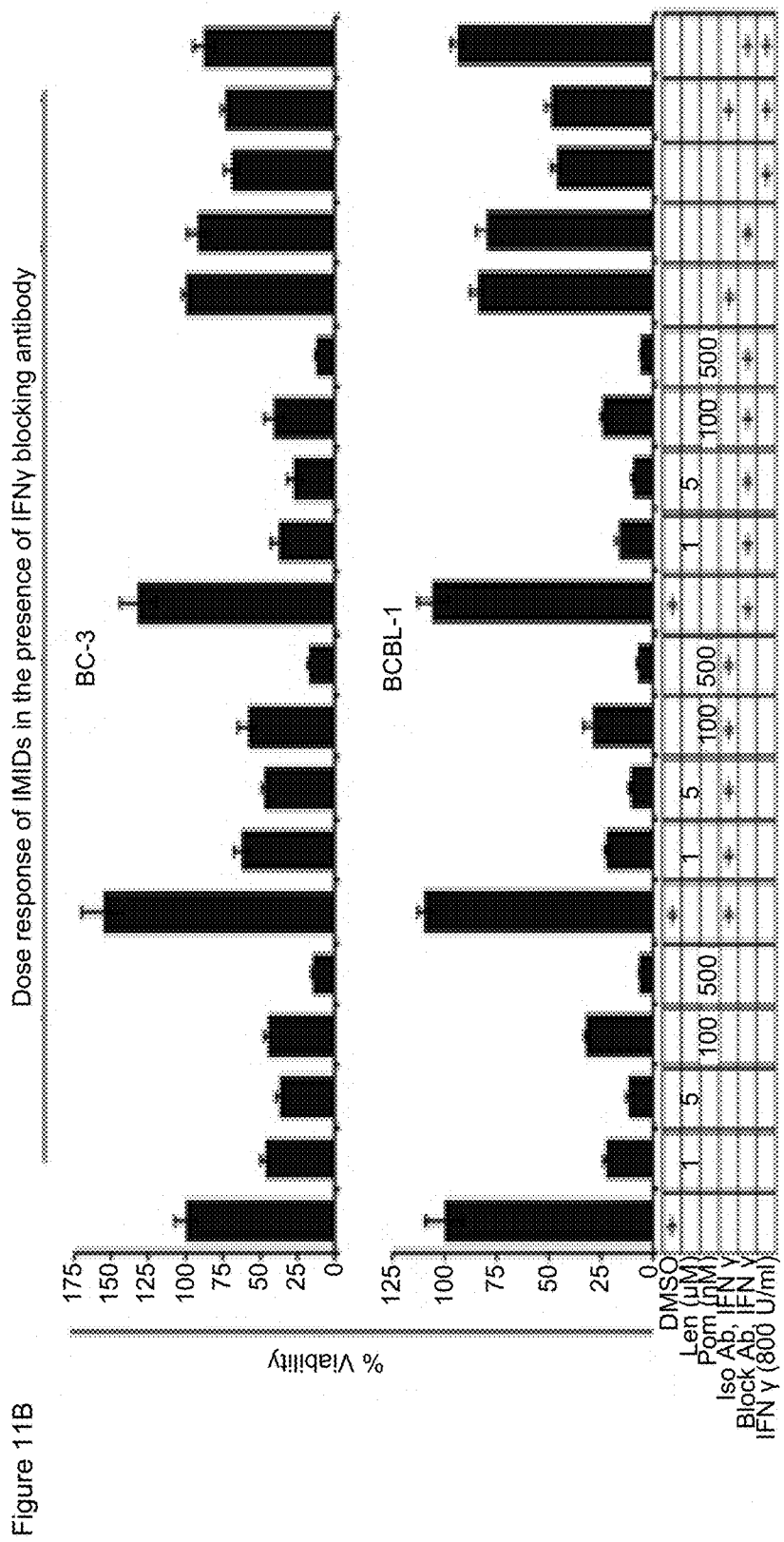
Figure 12:
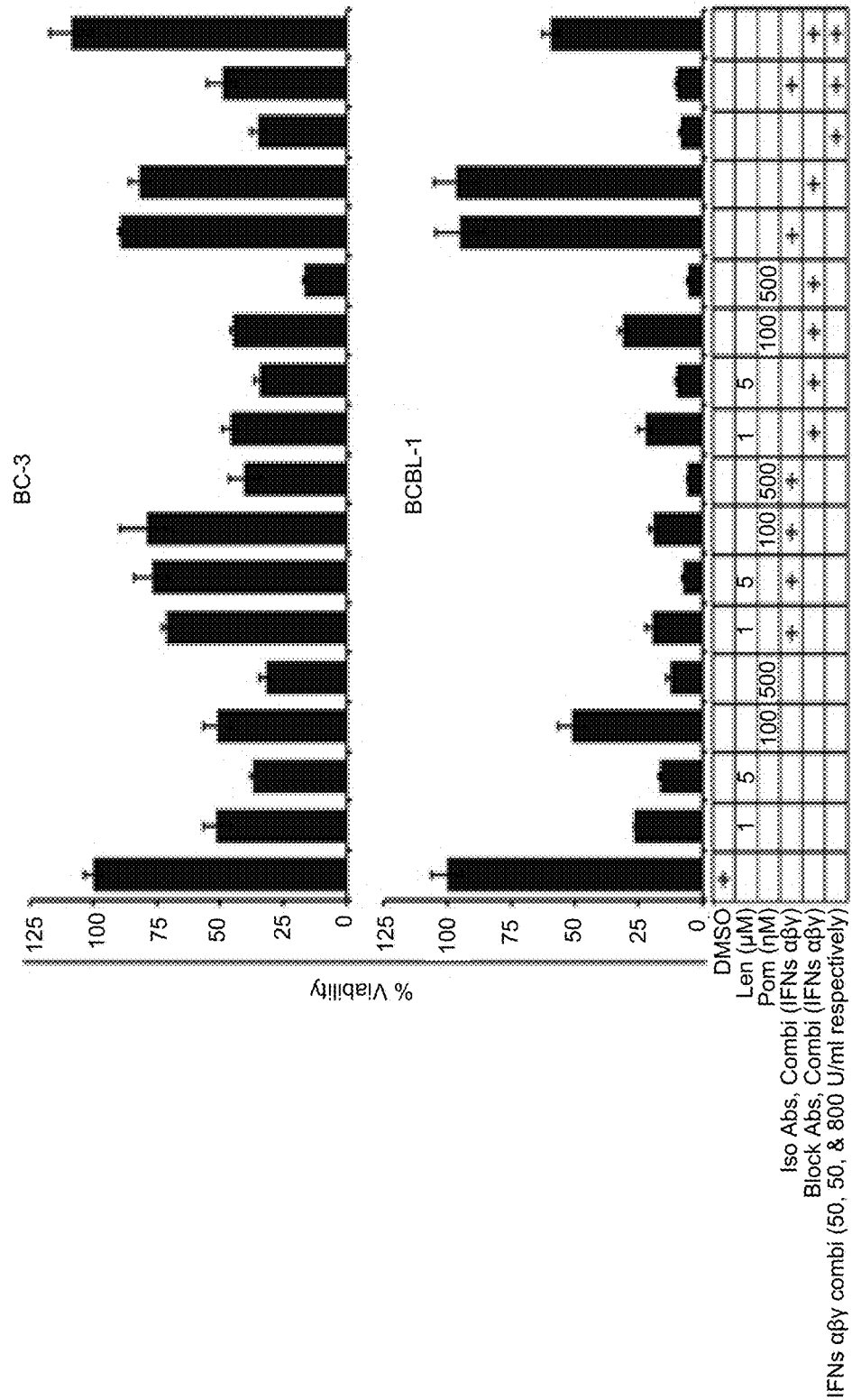
FIG. 12. Blocking of interferons α, β, and γ (IFNs αβγ) together also did not block the anti-proliferative activity of IMiDs in PEL. BC-3 and BCBL-1 were treated with indicated concentrations of IMiDs, IFNs αβγ and IFNs αβγ blocking antibodies combined (Block Ab) for 4 days. IFN-α blocking antibody was used at a concentration which blocks 450 U/ml of IFN-α by 50%, IFN-β blocking antibody was used at a concentration which blocks 350 U/ml of IFN-α by 50% and IFN-γ blocking antibody was used at a concentration which blocks 1090 U/ml of IFN-γ by 50%. Isotype antibodies (Iso Ab) corresponding to same species was as used as control. The values shown are mean±SE (n=3).

Activation of IFN Signaling by IMiDs is not Responsible for its Cytotoxic Effect in PEL To confirm that activation of IFN pathway is responsible for the anti-proliferative activity of IMiDs in PEL, we blocked the interferon pathway using blocking antibodies for IFNs α, β and γ. Interestingly, blocking IFN pathway did not block the anti-proliferative potential of IMiDs towards PEL (FIGS. 11A and 11B). As expected the blocking antibodies blocked the antiproliferative potential of their respective rIFNs very effectively (FIGS. 11A and 11B). It is possible that while blocking individual types of IFN using blocking antibodies then different IFN types may compensate for the loss of activity for one another. To rule out this possibility we combined all the three IFNs α, β and γ blocking antibodies together and then treated with IMiDs. Blocking all the three IFNs together also did not block the anti-proliferative potential of IMiDs towards PEL (FIG. 12). In contrast, as expected they efficiently block the anti-proliferative potential of all the three rIFNs combined together (FIG. 12). Collectively, these results clearly suggest that activation of interferon pathway is not responsible for the anti-proliferative potential of IMiDs in PEL.

Example VIII

Figure 13A:
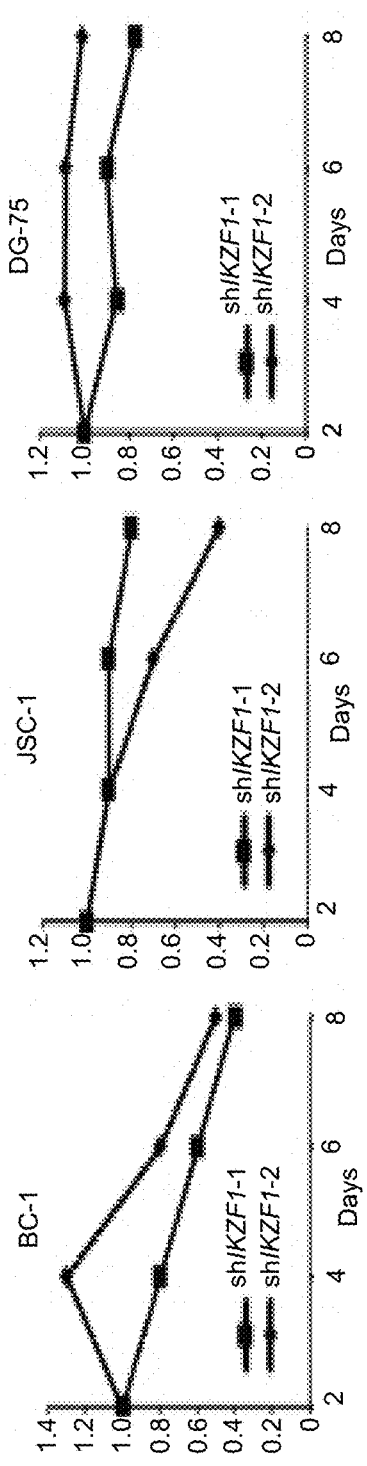
FIGS. 13A-13G.

IMiDs Rapidly Downregulate IKZF1 and Knocking Down IKZF1 Using Specific shRNAs is Toxic to PEL Via Down-regulating the Expression of IRF4 and MYC Ikaros family proteins IKZF1 (Ikaros) and IKZF3 (Aiolos) are transcription factors which play crucial roles in immunity and cell-fate decisions (John and Ward, 2011). Recently, it has been shown that IMiDs selectively degrade these transcription factors in multiple myeloma cells (Kronke et al., 2014; Lu et al., 2014). To test whether IMiDs decrease the expression of IKZF1 and IKZF3 in PEL, BC-3, BCBL-1, JSC-1 and DG-75 cells were treated with increasing concentrations of IMiDs for 48 h followed by western blotting detection of IKZF1 and IKZF3. Interestingly, IMiDs rapidly downregulated the expression of IKZF1 in all the PEL cells even at the lowest concentrations tested (FIG. 3A). Whereas, the level of IKZF3 was down regulated only at higher concentrations in BC-3 and BCBL-1 and stayed the same in JSC-1 (FIG. 3A). Further, targeting of IKZF1 by specific shRNAs is also toxic to PEL cells selectively with little or no effect on DG-75 cells (FIG. 3B and FIG. 13A) and knocking down IKZF1 down regulated the expression of IRF4 and MYC (FIG. 3C) thus suggesting that IKZF1 is an upstream target of IMiDs in PEL.

Example IX

IMiDs Act on IKZF1 Post-Translationally

Figure 3D:
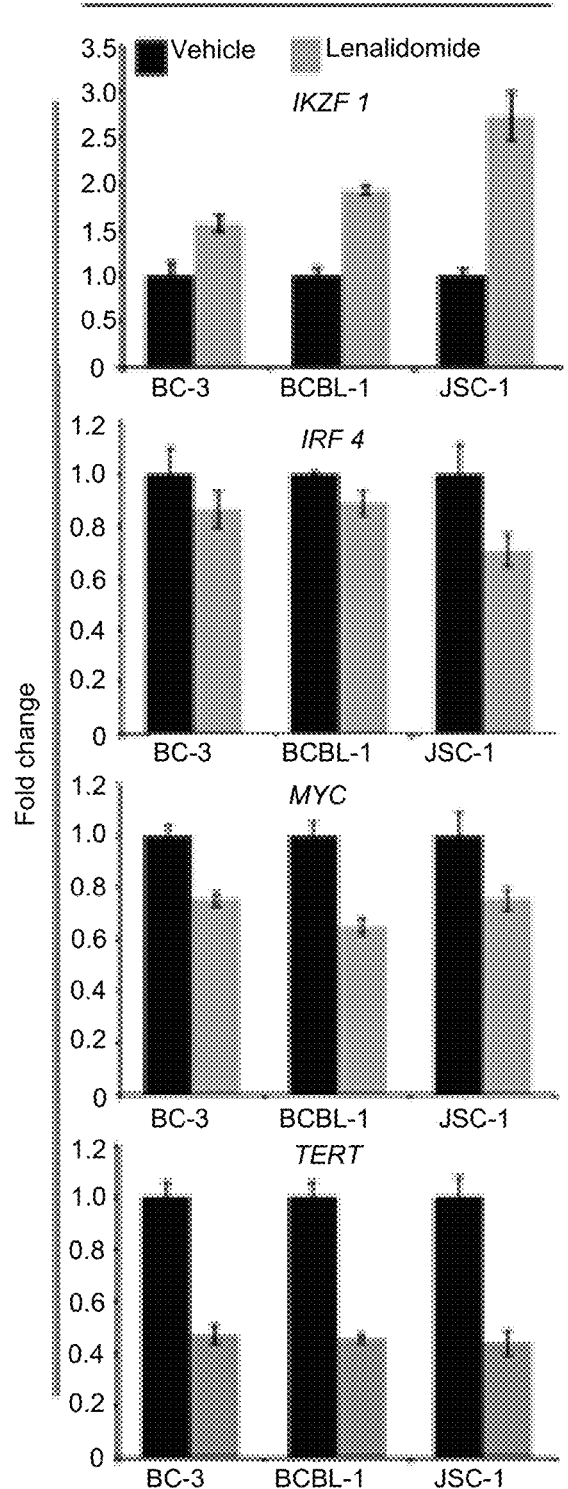
Figure 3E:
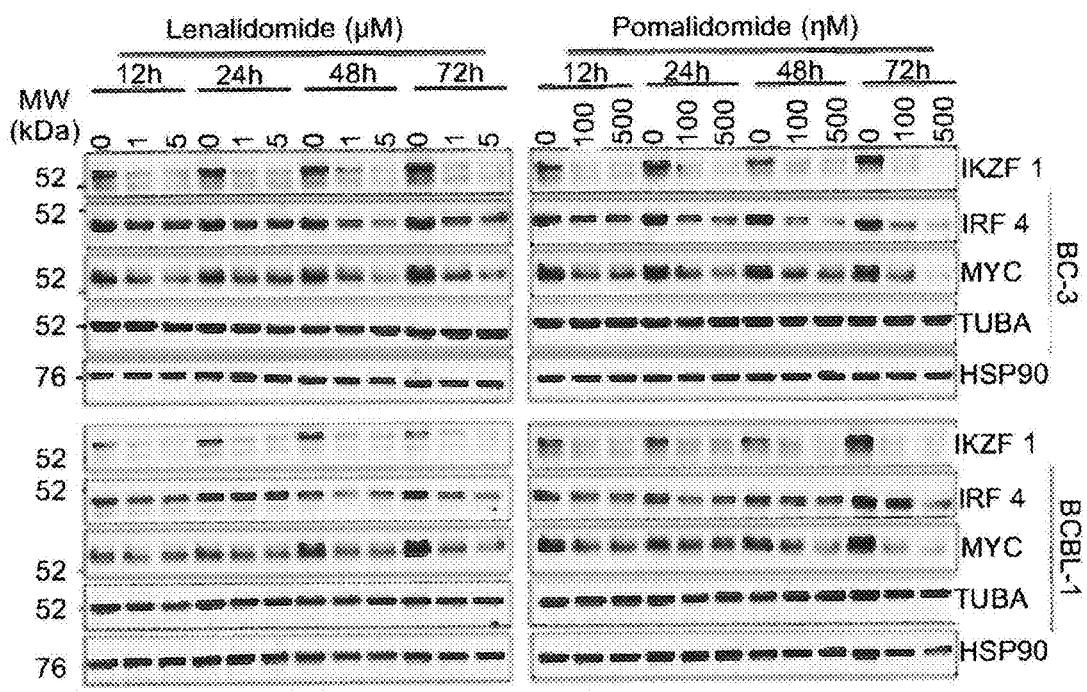
Figure 3F:
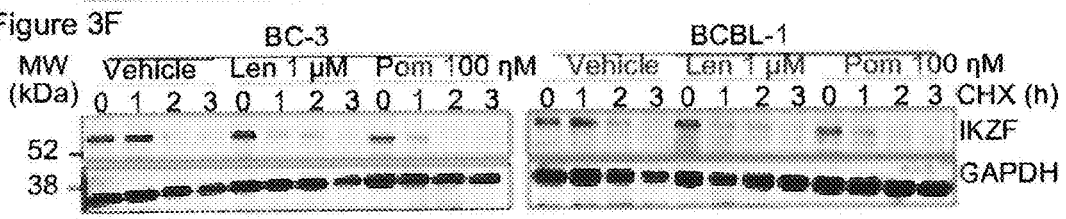
FIG. 3F, Effect of IMiDs on IKZF1 protein stability. BC-3 and BCBL-1 cells were treated with vehicle or IMiDs in the presence of 100 µg/ml of cycloheximide (CHX) for 0, 1, 2, and 3 h. Whole cell lysates were immunoblotted for IKZF1 and GAPDH.

IMiDs rapidly downregulate the protein level of IKZF1. Surprisingly, the mRNA levels of IKZF1 was moderately up-regulated upon treatment with lenalidomide for 24 h in BC-3, BCBL-1 and JSC-1 cells (FIG. 3D). Whereas, the mRNA levels of IRF4, MYC and its target TERT is down-regulated mildly, and moderately, respectively (FIG. 3D). This data suggests that IMiDs act on IKZF1 post-translationally. To further understand the molecular hierarchy on the targets of IMiDs, we treated BC-3 and BCBL-1 cells with increasing concentrations lenalidomide and pomalidomide for 12, 24, 48 and 72 h and the cell lysates were probed for IKZF1, IRF4, MYC, Tubulin and HSP90 (Tubulin and HSP90 are loading controls). IKZF1 was down regulated rapidly as early as 12 h post-treatment even at the lowest concentrations of IMiDs (FIG. 3E) whereas, the levels of IRF4 and MYC were downregulated significantly starting at 24 h (FIG. 3E). This data confirms that IKZF1 is the upstream target of IMiDs in PEL. To check whether IMiDs decreases the half-life of IKZF1, BC-3 and BCBL-1 cells were treated with IMiDs in the presence of protein synthesis inhibitor cycloheximide (CHX) for 0, 1, 2 and 3 h. Treatment of BC-3 and BCBL-1 cells with IMiDs in the presence of CHX rapidly degraded the level of IKZF1 as early as 1 h (FIG. 3F), whereas treatment of BC-3 and BCBL-1 with vehicle control in the presence of CHX degraded IKZF1 by 2 h (FIG. 3F) suggesting that IMiDs act on IKZF1 post-translationally.

Example X

Cereblon is Dispensable for the Survival of PEL Cells

Figure 4A:
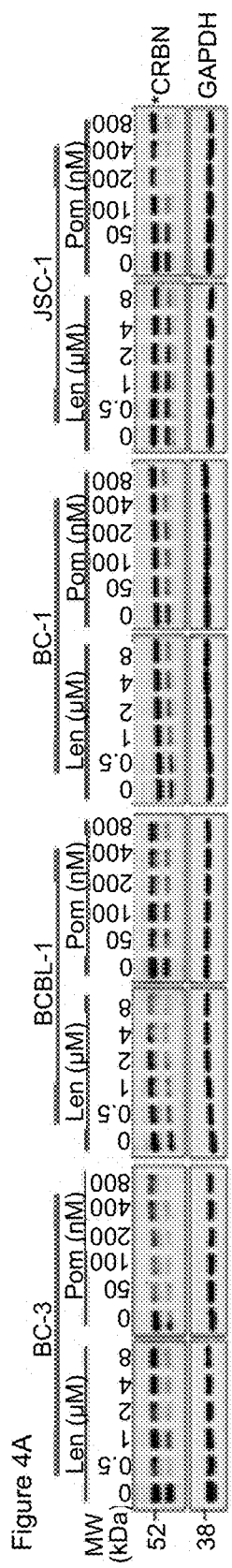
Figure 13C:
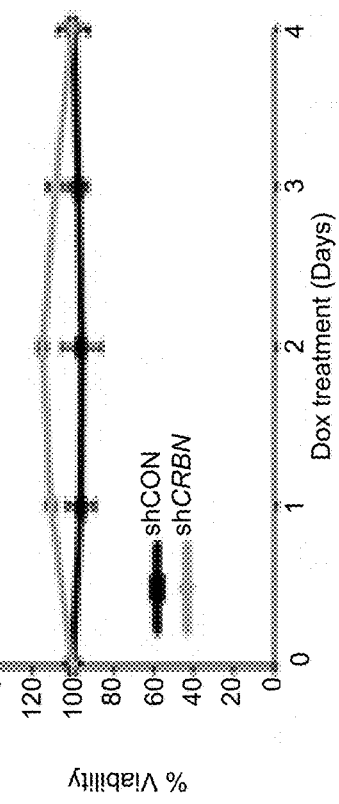
Figure 13B:
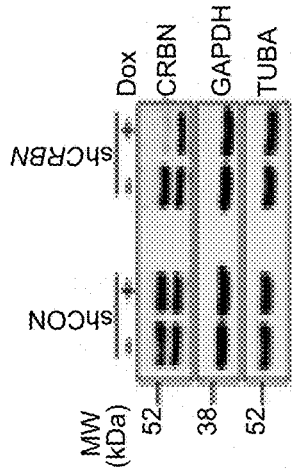

It has been recently shown that IMiDs bind to the cellular protein target cereblon (CRBN)(Ito et al., 2010; Lopez-Girona et al., 2012; Zhu et al., 2011). To test the effect of IMiDs on the expression level of CRBN in PEL, BC-3, BCBL-1, BC-1 and JSC-1 cells were treated with increasing concentrations of IMiDs for 48 h and the protein level of cereblon was detected by western blotting. IMiDs treatment resulted in a slight decrease in the level of cereblon in BC-3 cells with both lenalidomide and pomalidomide (FIG. 4A). In BCBL-1 cells, there was a decrease in CRBN level only at higher doses of lenalidomide with no change in the expression with pomalidomide, whereas there is no significant difference in the expression of cereblon upon treatment with IMiDs in both BC-1 and JSC-1 cells (FIG. 4A). Knocking down cereblon by shRNA significantly decreases the proliferation of multiple myeloma (Zhu et al., 2011) and ABC-DLBCL (Yang et al., 2012). To check the role of cereblon in PEL, we generated stable BC-3, BCBL-1, and BC-1 cells expressing tetracycline-inducible (TO) driven shRNA targeting CRBN (shCRBN) (Lu et al., 2014). Treatment of BC-3, BCBL-1 and BC-1 cells stably expressing shCRBN with Dox for 4 days significantly downregulated the expression of CRBN (FIG. 4B and FIG. 13B). In contrast, treatment of PEL cells with a TO driven non-targeting shRNA (shCON) had no effect on the expression of CRBN upon treatment with Dox (FIG. 4B and FIG. 13B). Interestingly, knocking down CRBN expression did not have any significant effect on the proliferation of BC-3, BCBL-1 and BC-1 cells (FIG. 4C and FIG. 13C). These data clearly suggest that CRBN is dispensable for the survival of PEL.

Example XI

CRBN is Essential for the Anti-Proliferative Effect of IMiDs in PEL

Figure 4E:
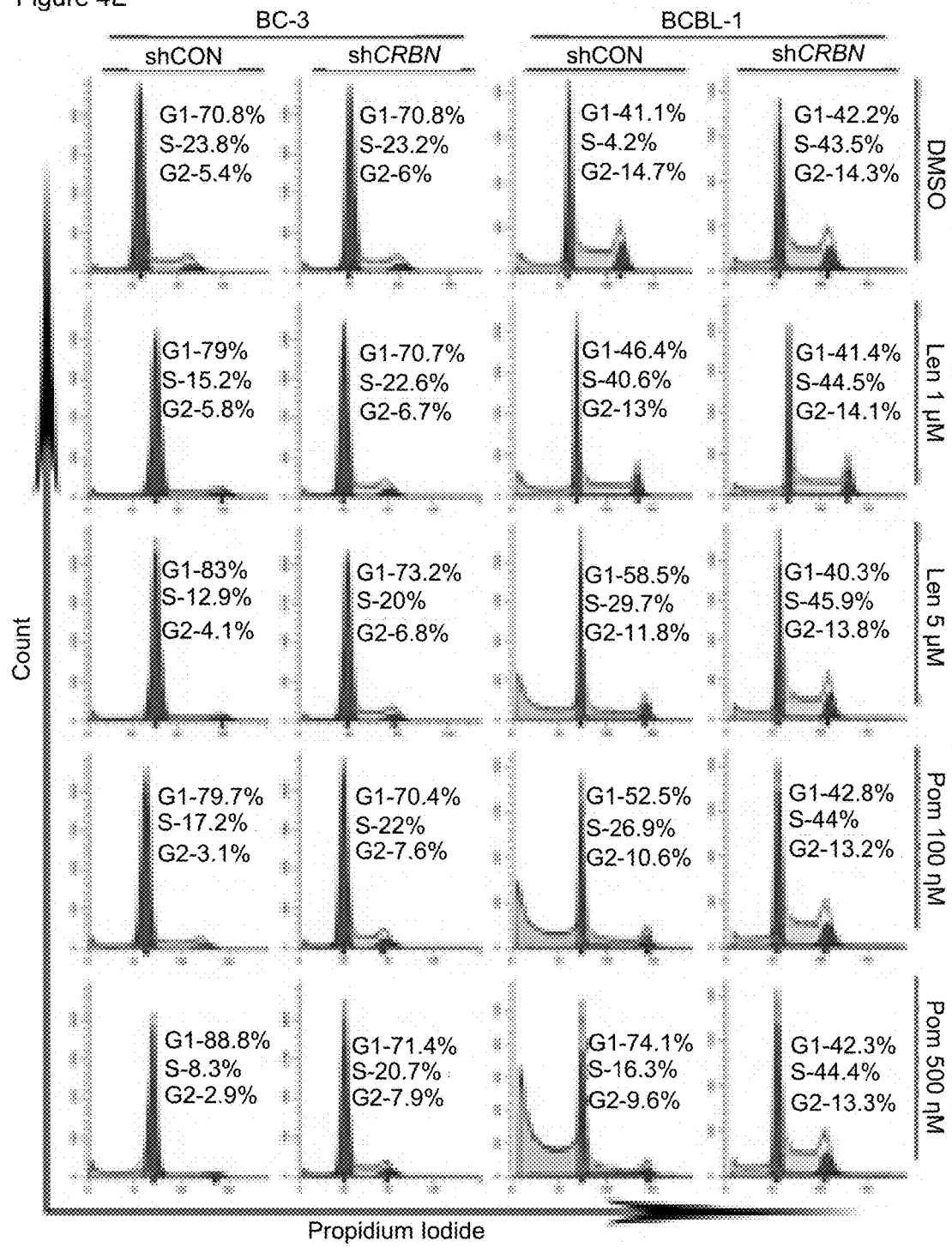
Figure 4F:
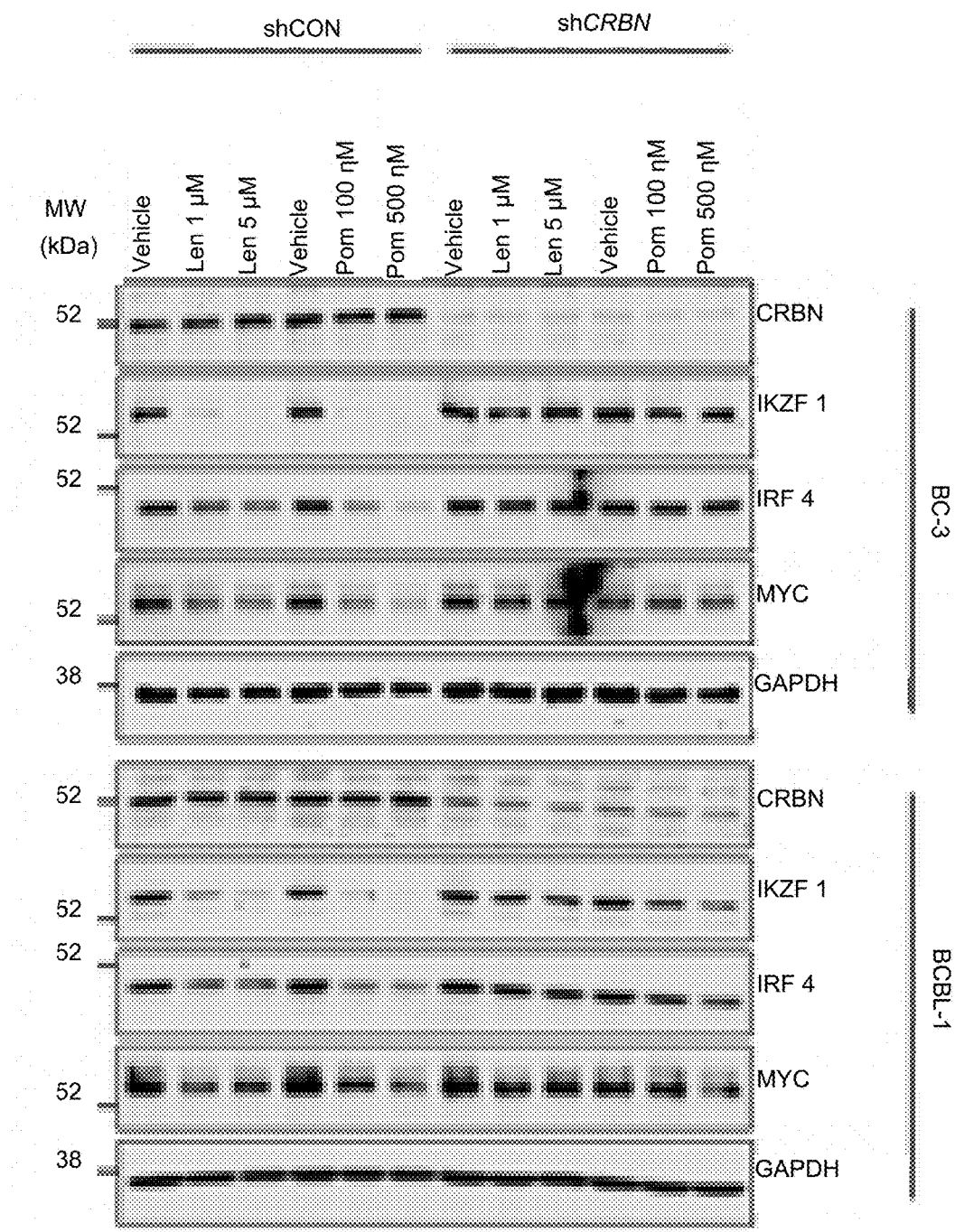
Figure 4G:
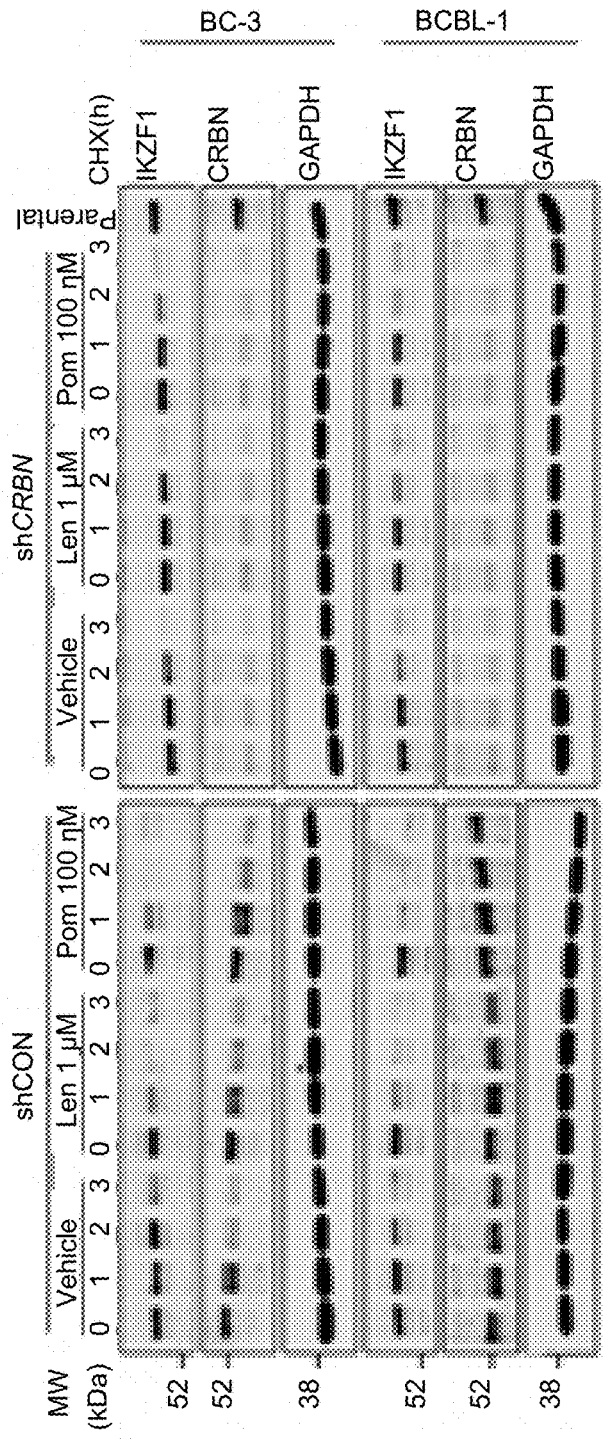
Figure 4H:
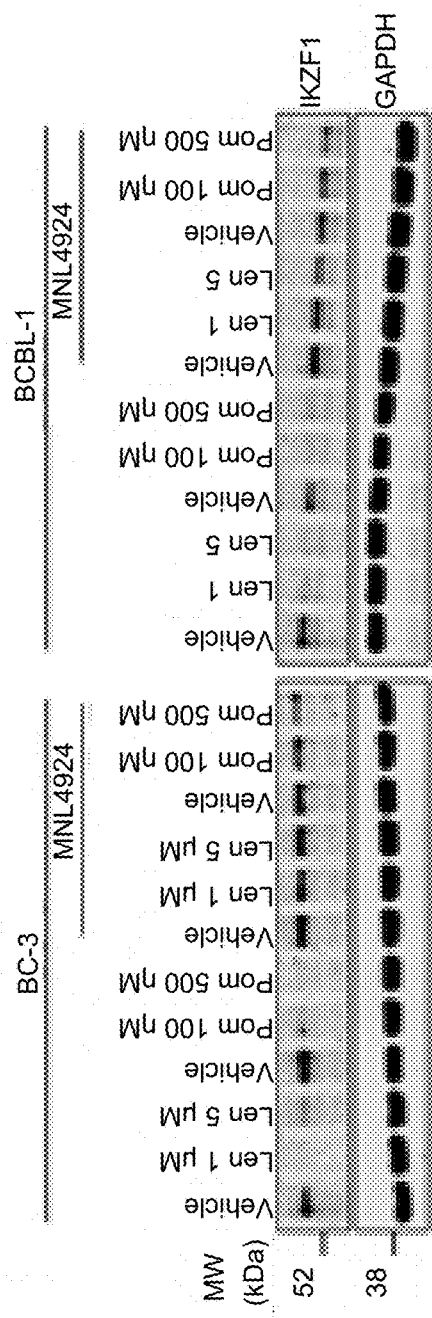
Figure 13D:
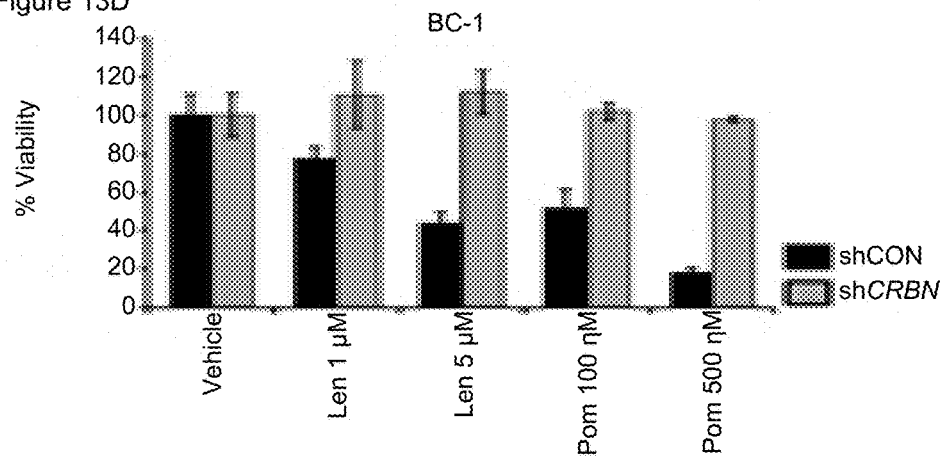
Figure 13E:
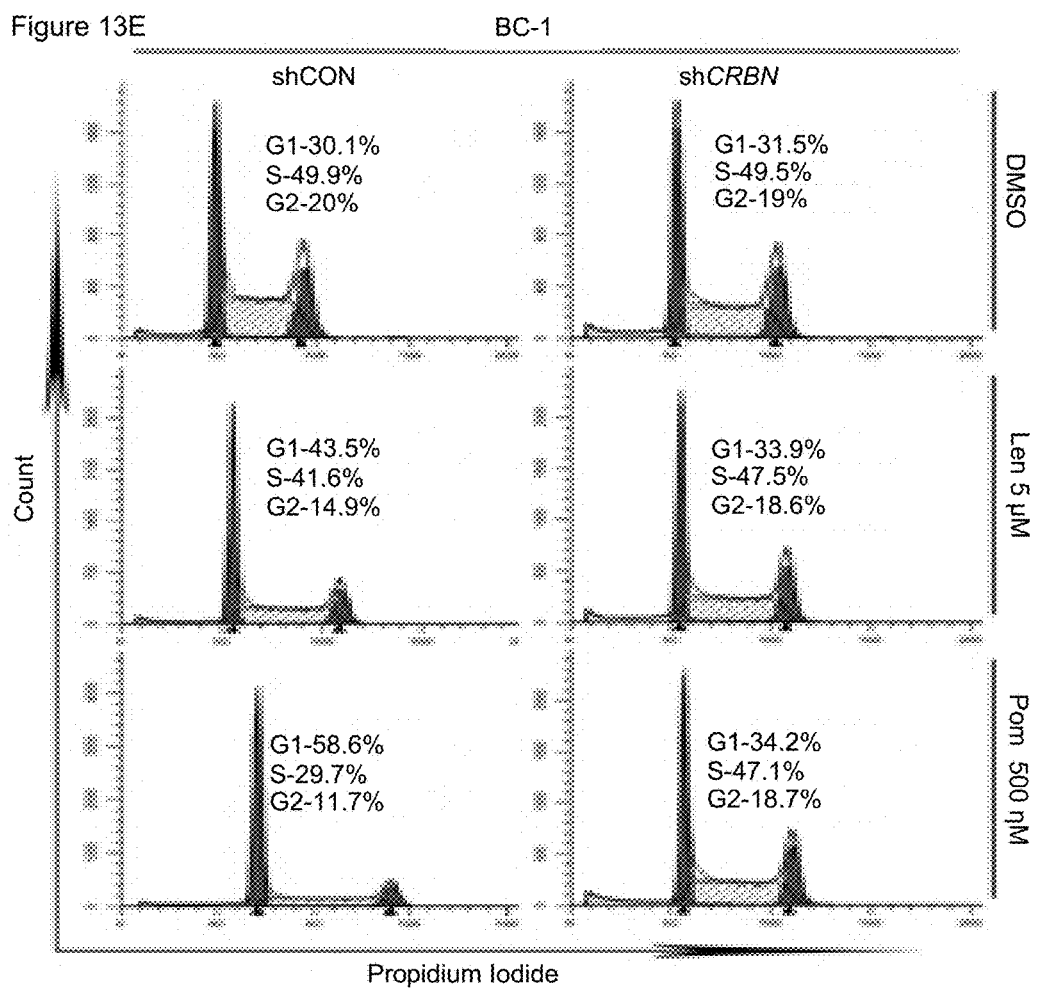

CRBN is not only the direct binding target for IMiDs, it is also essential for the immunomodulatory and antiproliferative activity of IMiDs (Ito et al., 2010; Lopez-Girona et al., 2012; Zhu et al., 2011). To test whether CRBN is essential for the anti-proliferative activity of IMiDs in PEL, BC-3, BCBL-1 and BC-1 cells stably expressing shCON and shCRBN were pre-treated with Dox followed by treatment with increasing doses of IMiDs. The anti-proliferative potential of IMiDs in shCRBN expressing PEL cells were almost completely blocked (FIG. 4D and FIG. 13D), whereas shCON expressing PEL cells show a significant decrease in the proliferation (FIG. 4D and FIG. 13D). Further, shCRBN expressing PEL cells did not block the cell cycle progression upon treatment with IMiDs (FIG. 4E and FIG. 13E). In contrast, shCON expressing PEL cells showed a typical G1 cell cycle arrest along with a decreased number of cells in S phase upon treatment with IMiDs (FIG. 4E and FIG. 13E). In this study, we have previously shown that IMiDs rapidly degrades IKZF1 thereby down-regulating the expression of IRF4 and MYC, which is essential for the survival of PEL (Tolani et al., 2013). To test whether CRBN acts upstream of IKZF1, IRF4 and MYC in IMiDs treated PEL, BC-3 and BCBL-1 stably expressing shCON and shCRBN were pre-treated with Dox followed by treatment with increasing doses of IMiDs in the presence of Dox for 48 h, and the cell lysates were probed for the expression of CRBN, IKZF1, IRF4, MYC and GAPDH. As expected, shCON expressing BC-3 and BCBL-1 treated with IMiDs showed a robust reduction in IKZF1, along with a significant decrease in the expression levels of IRF4 and MYC but without any significant difference in the level of CRBN (FIG. 4F). In contrast, shCRBN expressing BC-3 and BCBL-1 cells treated with IMiDs did not have any change in the expression levels of IKZF1, IRF4 and MYC but CRBN expression was significantly downregulated (FIG. 4F). IMiDs act on IKZF1 post-translationally by direct protein degradation. To check whether CRBN is essential for this purpose, BC-3 and BCBL-1 cells stably expressing shCON and shCRBN were pre-treated with Dox followed by treatment with IMiDs in the presence of CHX and Dox for 0, 1, 2 and 3 h. As expected, IMiDs rapidly degraded IKZF1 in BC-3 and BCBL-1 shCON as early as 1 h but in the vehicle treated shCON cells it took 2-3 h (FIG. 4G) with no change in the degradation level of CRBN between IMiDs and vehicle treatment (FIG. 4G). In contrast, there is no change in the degradation of IKZF1 between vehicle and IMiDs treatment in BC-3 and BCBL-1 expressing shCRBN but with a significant decrease in the expression of CRBN (FIG. 4G). This data clearly suggests that CRBN is essential for the rapid protein level degradation of IKZF1 by IMiDs. CRBN is a component and substrate receptor for Cul4-DDB1-E3 ubiquitin ligases complex (Ito et al., 2010). In principle the function of E3 ubiquitin ligases complex is to direct the poly-ubiquitination of substrate proteins by specifically interacting with ubiquitin-conjugating enzyme (E2) (Petroski and Deshaies, 2005). Culling-RING ubiquitin ligase (CRL) activity depends on NEDDylation (Soucy et al., 2009). MLN4924, a small molecule NEDD8-activating enzyme inhibitor has been shown to disrupt the CRL activity. To test whether CRL activity is essential for the robust protein level degradation of IKZF1 by IMiDs in PEL, BC-3 and BCBL-1 cells were pretreated with MLN4924 for 1 h followed by treatment with IMiDs for 15 h. As expected, treatment with IMiDs rapidly downregulated the expression of IKZF1 in BC-3 and BCBL-1 cells (FIG. 4H), but treatment of BC-3 and BCBL-1 cells in the presence of MLN4924 completely blocked the downregulation of IKZF1 by IMiDs (FIG. 4H). These data clearly suggest that CRBN and its CRL activity are essential for the anti-proliferative potential of IMiDs in PEL.

Example XII

CRBN Expression Cannot Serve as a Marker for the Sensitivity of IMiDs

Figure 5A:
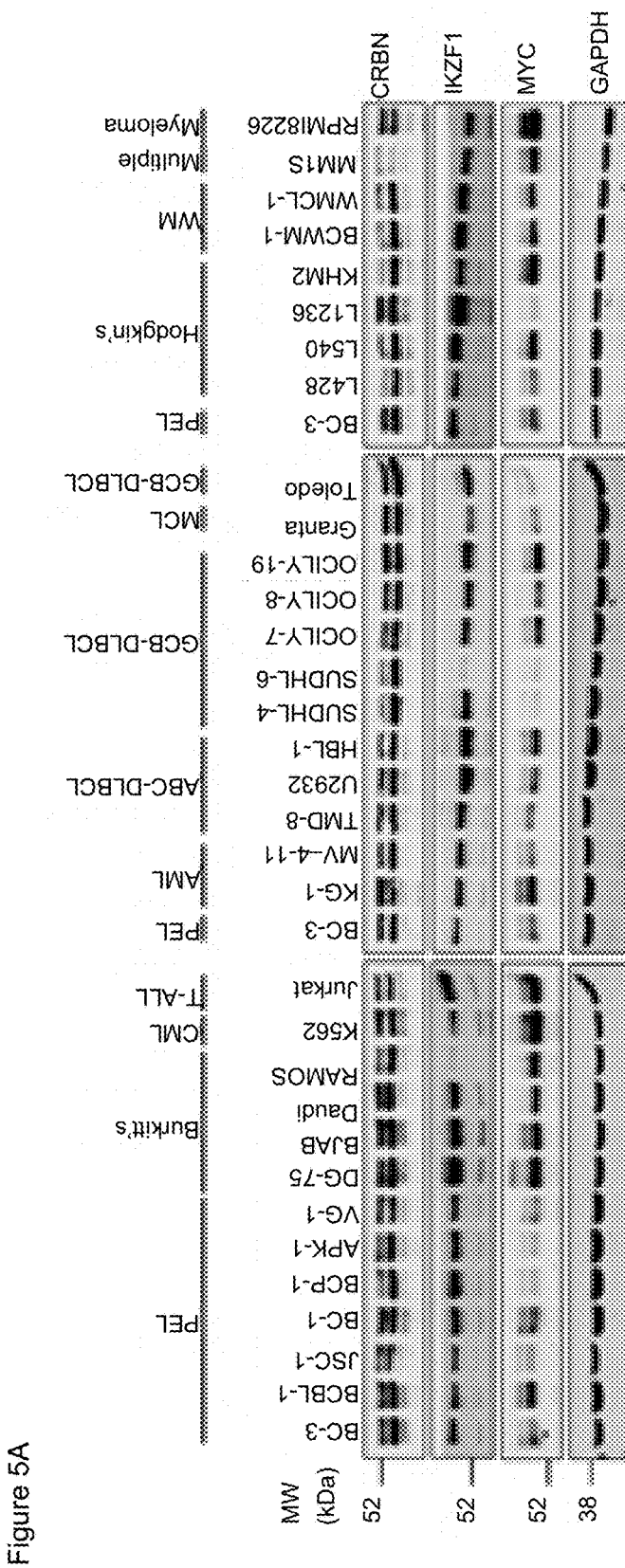

Decrease or loss of expression of CRBN has been associated with resistance to IMiDs therapy in multiple myeloma (Zhu et al., 2011). Whereas high CRBN expression is associated with better survival in patients with newly diagnosed multiple myelomas (Broyl et al., 2013). Because CRBN is essential for its anti-proliferative potential, it is possible that the cells which are resistant to IMiDs may have decreased or lost expression of CRBN. To test this hypothesis, we probed same panel of 33 hematological cancer cell lines in which we initially did the dose response of IMiDs for CRBN. Surprisingly, all the 33 cancer cell lines express CRBN at varying levels (FIG. 5A). And in fact some of the resistant cells (BJAB and DG-75) express slightly higher levels of CRBN than that in the PEL (FIG. 5A). Similarly, no correlation was observed with the expressions of IKZF1 and MYC in this panel of cell lines (FIG. 5A). This result suggests that even though CRBN is essential for the anti-proliferative activity of IMiDs, the expression levels of CRBN, IKZF1 or MYC cannot serve as a marker for sensitivity to IMiDs.

Example XIII

Figure 13F:
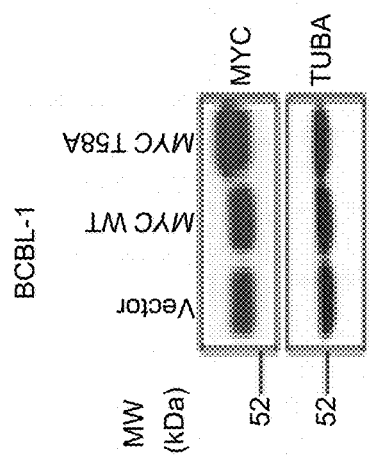
Figure 13G:
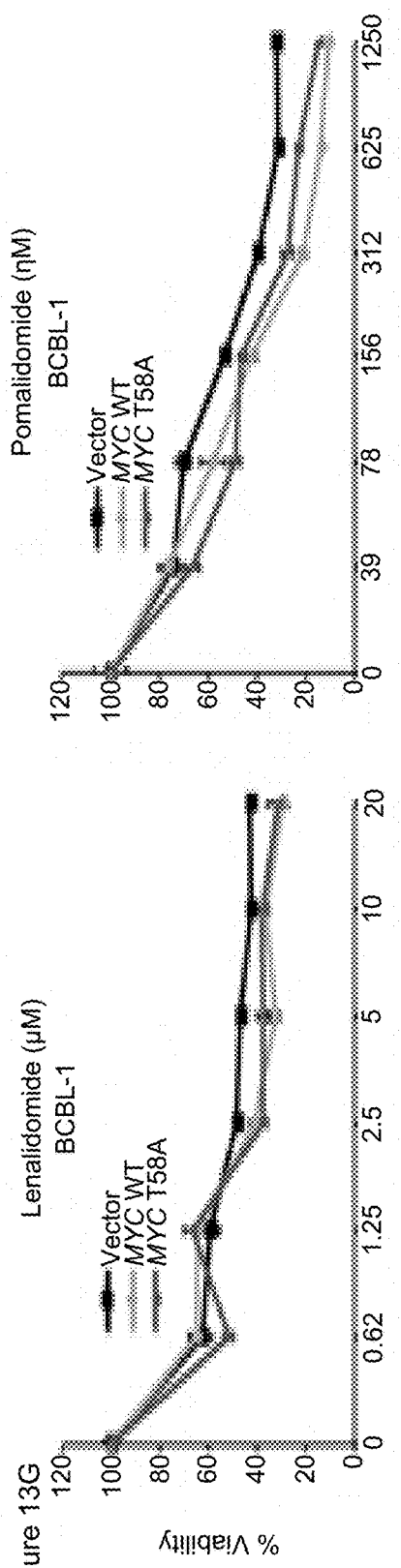

Ectopic Over-Expression of MYC Did not have any Effect on IMiDs Sensitivity to PEL Our studies suggest that MYC is a downstream target of IMiDs in PEL but the role of MYC in the activity of IMiDs is not known. To check the gain of expression of MYC on the activity of IMiDs towards PEL, we generated stable clones of BC-3 and BCBL-1 cells expressing an empty retroviral vector, MYC wild type (WT) and a physiologically relevant MYC-T58A mutant, which is resistant to phosphorylation-induced degradation and is also a hot spot coding region of MYC for mutations in lymphoma (Bahram et al., 2000). Consistent with the increased stability of T58A mutant, MYC protein expression is modestly increased in the MYC-WT expressing PEL cells but strongly increased in the MYC-T58A expressing BC-3 and BCBL-1 cells (FIG. 5B and FIG. 13F). We next tested the effect of MYC over expression on the activity of IMiDs by treating them with increasing concentrations of IMiDs. We did not observe any significant difference in proliferation in both BC-3 and BCBL-1 expressing MYC-WT and MYC-T58A in comparison with cells expressing vector alone (FIG. 5C and FIG. 13G). This data suggests that over expression of MYC may not confer resistance to IMiDs.

Example XIV

Knocking Down MYC by shRNA Enhances the Sensitivity of IMiDs to PEL

Figure 5H:
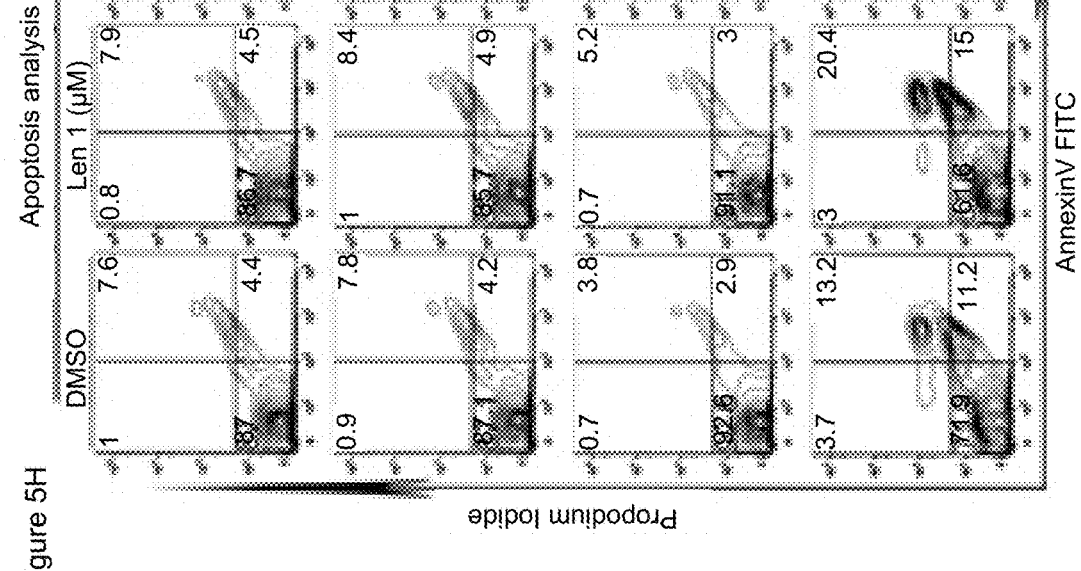
Figure 5G:
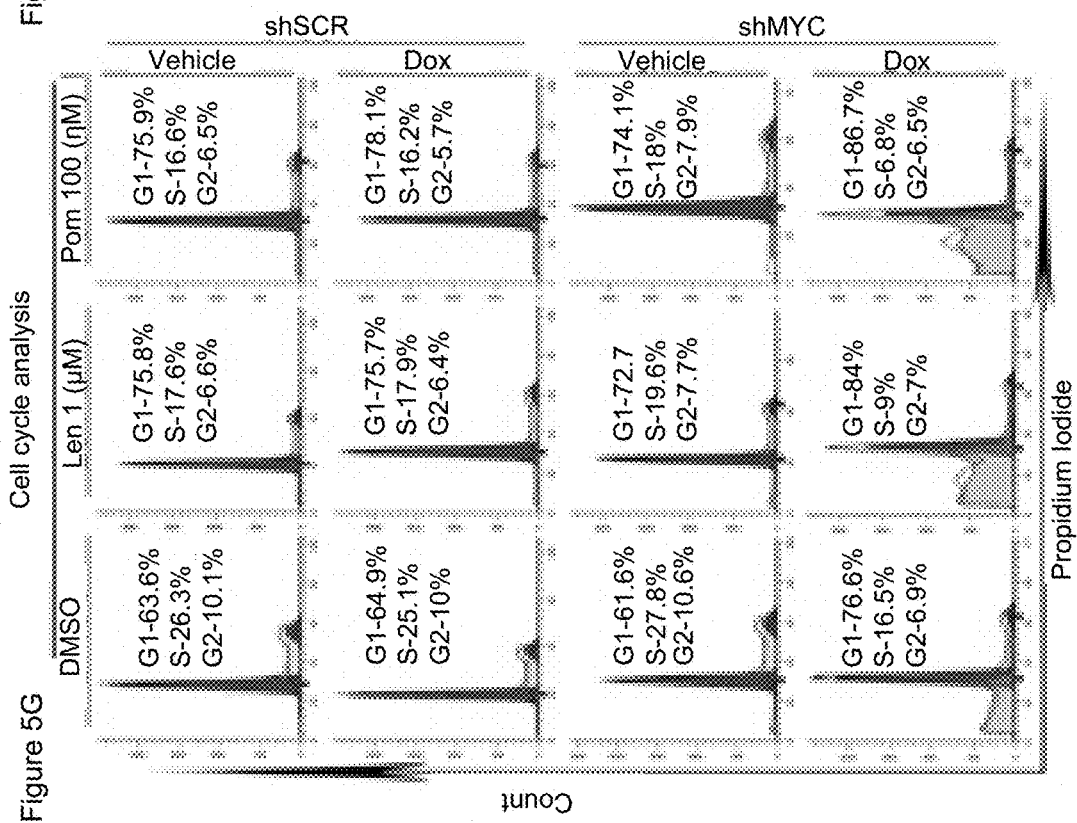

To test the effect of loss of MYC on the anti-proliferative activity of IMiDs towards PEL, we generated stable BC-3 cells expressing tetracycline-inducible H1 promoter (H1/TO)-driven shRNA targeting MYC (shMYC). Treatment of BC-3 cells stably expressing shMYC with Dox resulted in a significant down-regulation of MYC (FIG. 5D). Treatment of BC-3 cells stably expressing shMYC with Dox for different time points significantly decreased the proliferation of cells starting at day 1 (FIG. 5E). In contrast, treatment of BC-3 cells stably expressing H1/TO shRNA targeting scrambled sequence (shSCR) with Dox over a period of 5 days did not have any significant effect on proliferation (FIG. 5E). This data confirms the essential role of MYC in the survival and proliferation of PEL (Tolani et al., 2013). We next tested the effect of MYC knockdown on the activity of IMiDs. For this purpose, BC-3 cells stably expressing shSCR and shMYC were co-treated with Dox and IMiDs. Interestingly, knocking down MYC significantly enhanced the anti-proliferative potential of IMiDs (FIG. 5F), whereas, no significant difference was observed in BC-3 cells stably expressing shSCR treated with IMiDs in the presence/absence of Dox (FIG. 5F). Further, treatment of BC-3 cells stably expressing shMYC with IMiDs and Dox significantly enhanced the number of cells arrested at G1 phase with a concurrent decrease in S phase than either agent alone (FIG. 5G) and the number of apoptotic cells is significantly higher in IMiDs and Dox treated BC-3 cells expressing shMYC cells than Dox alone as observed by larger apoptotic cells peak (FIG. 5G) which is confirmed by annexinV-FITC staining (FIG. 5H). These results point to the existence of potential synergism between IMiDs and inhibition of MYC.

Example XV

BRD4 Inhibitors JQ-1, IBET151 and PFI-1 are Synergistic with IMiDs in PEL

Figure 6A:
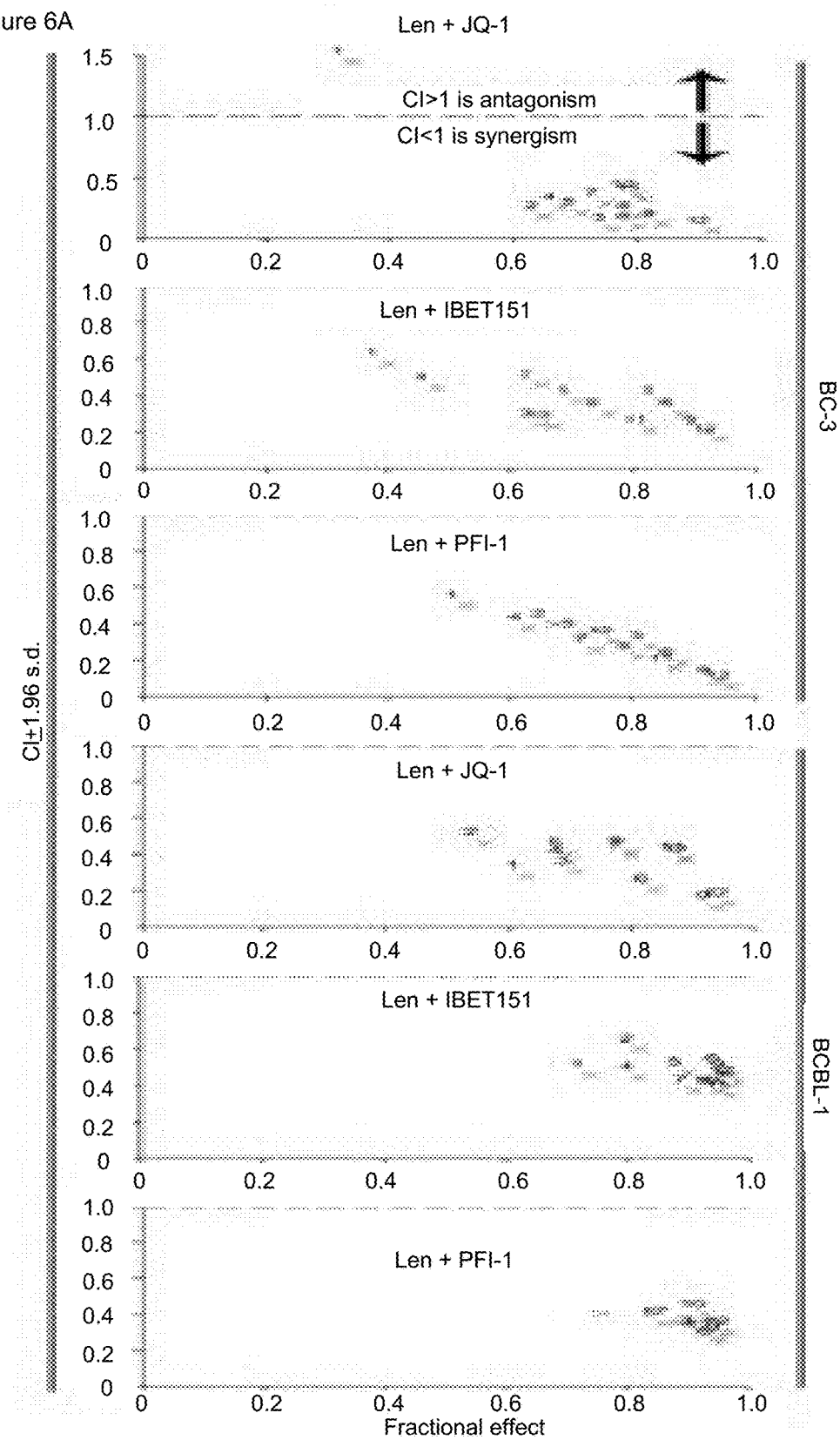
FIGS. 6A-6E. BRD4 inhibitors and IMiDs display synergistic anti-proliferative activity against PEL.
Figure 6B:
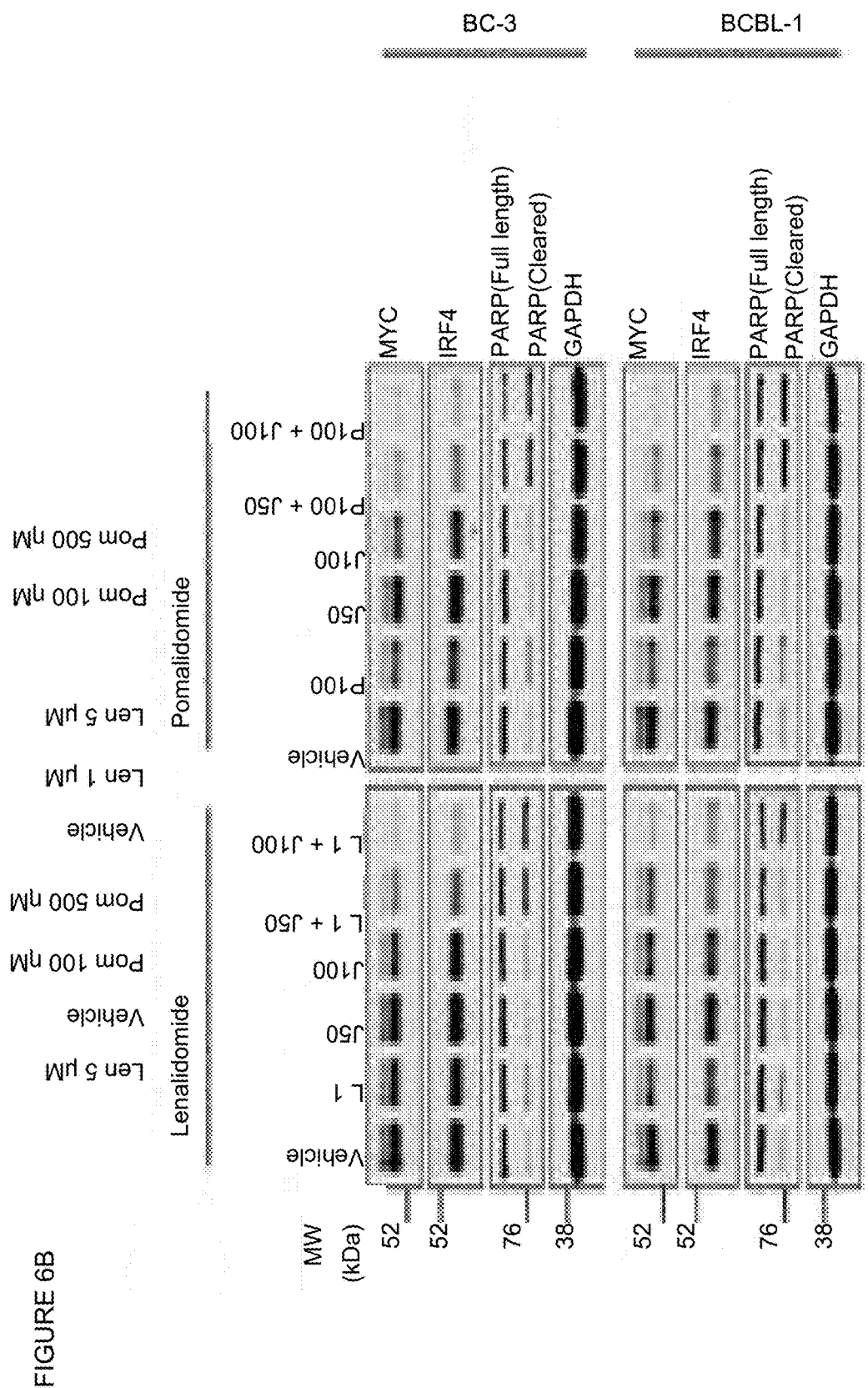
Figure 6C:
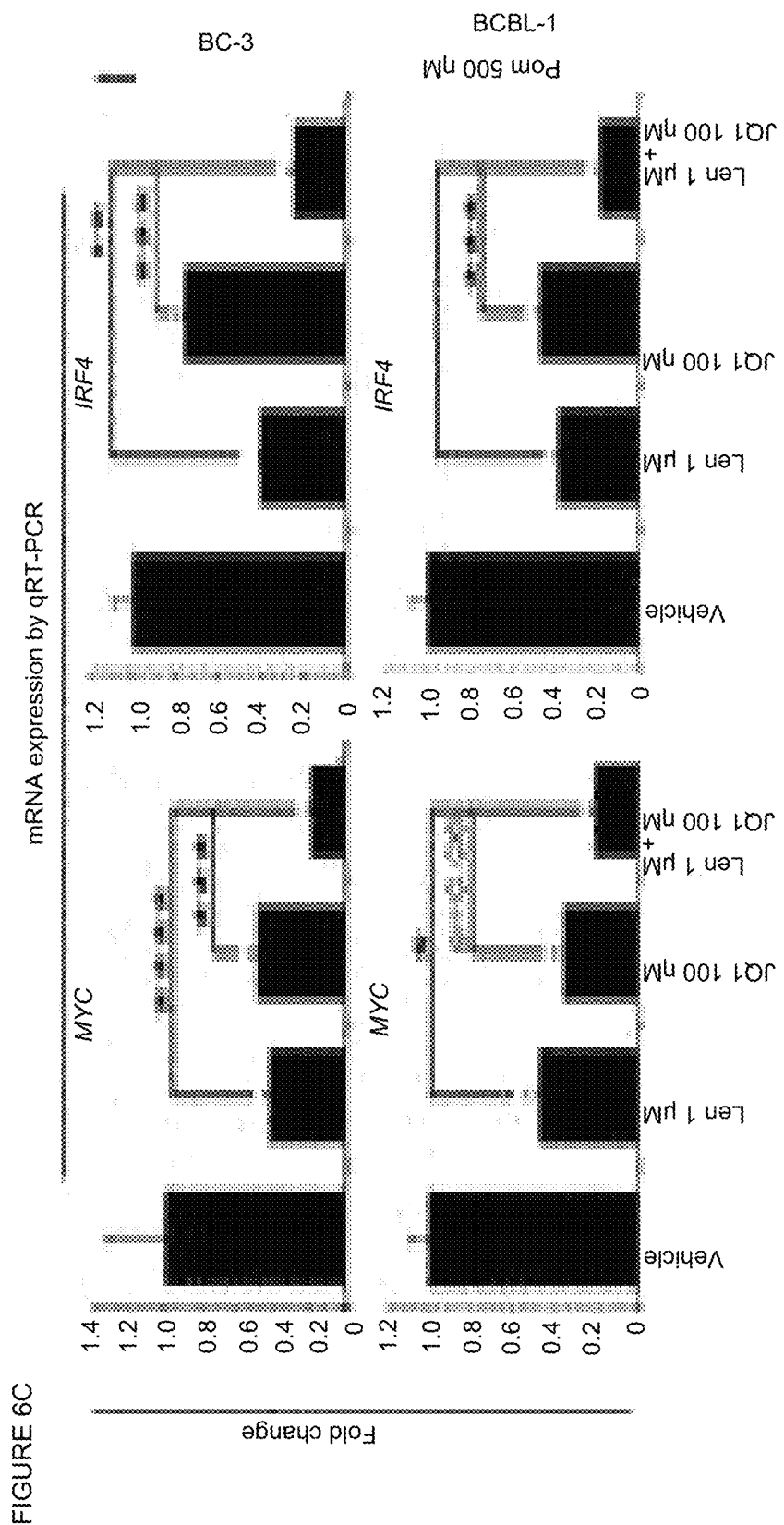
Figure 6D:
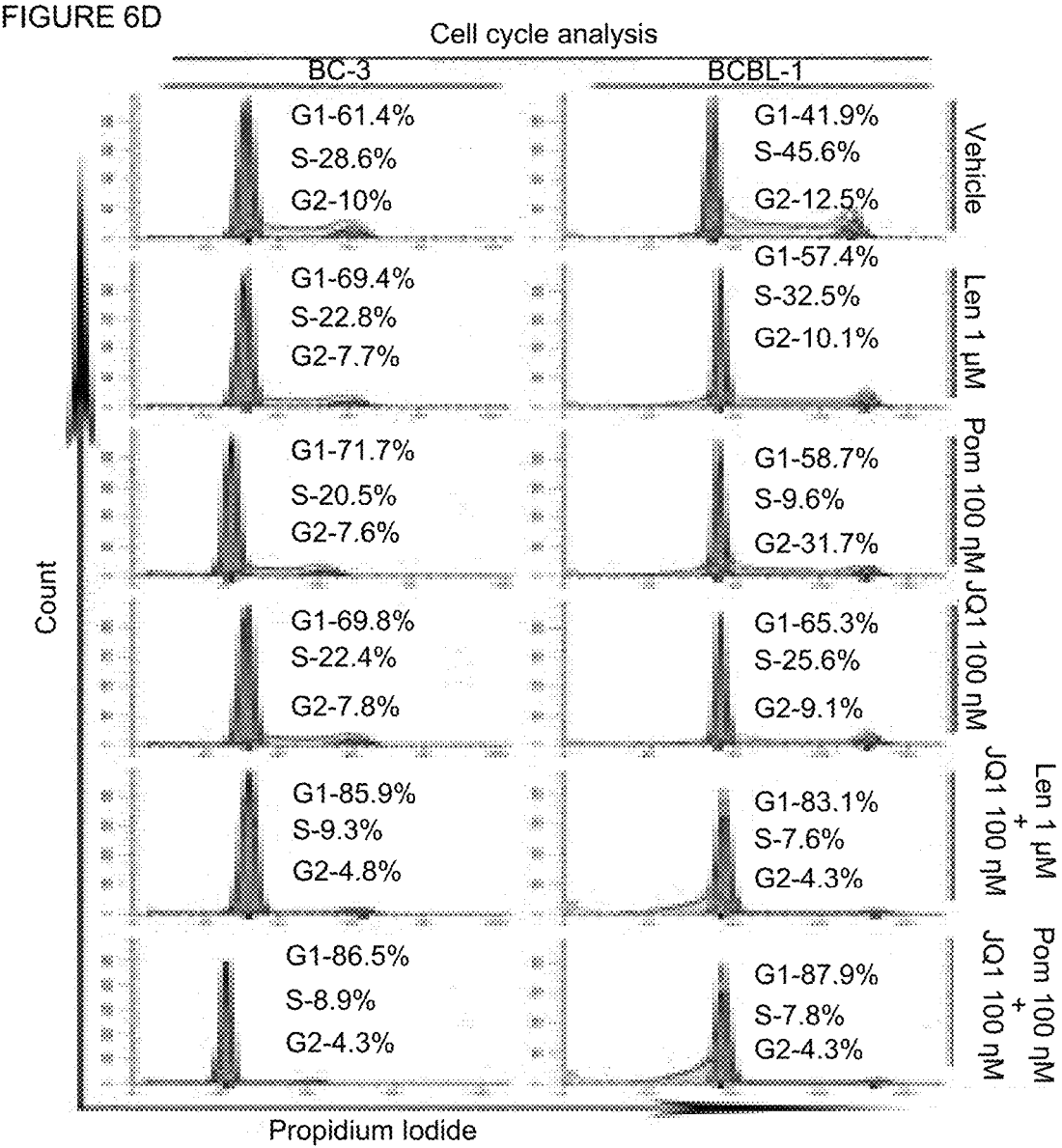
Figure 6E:
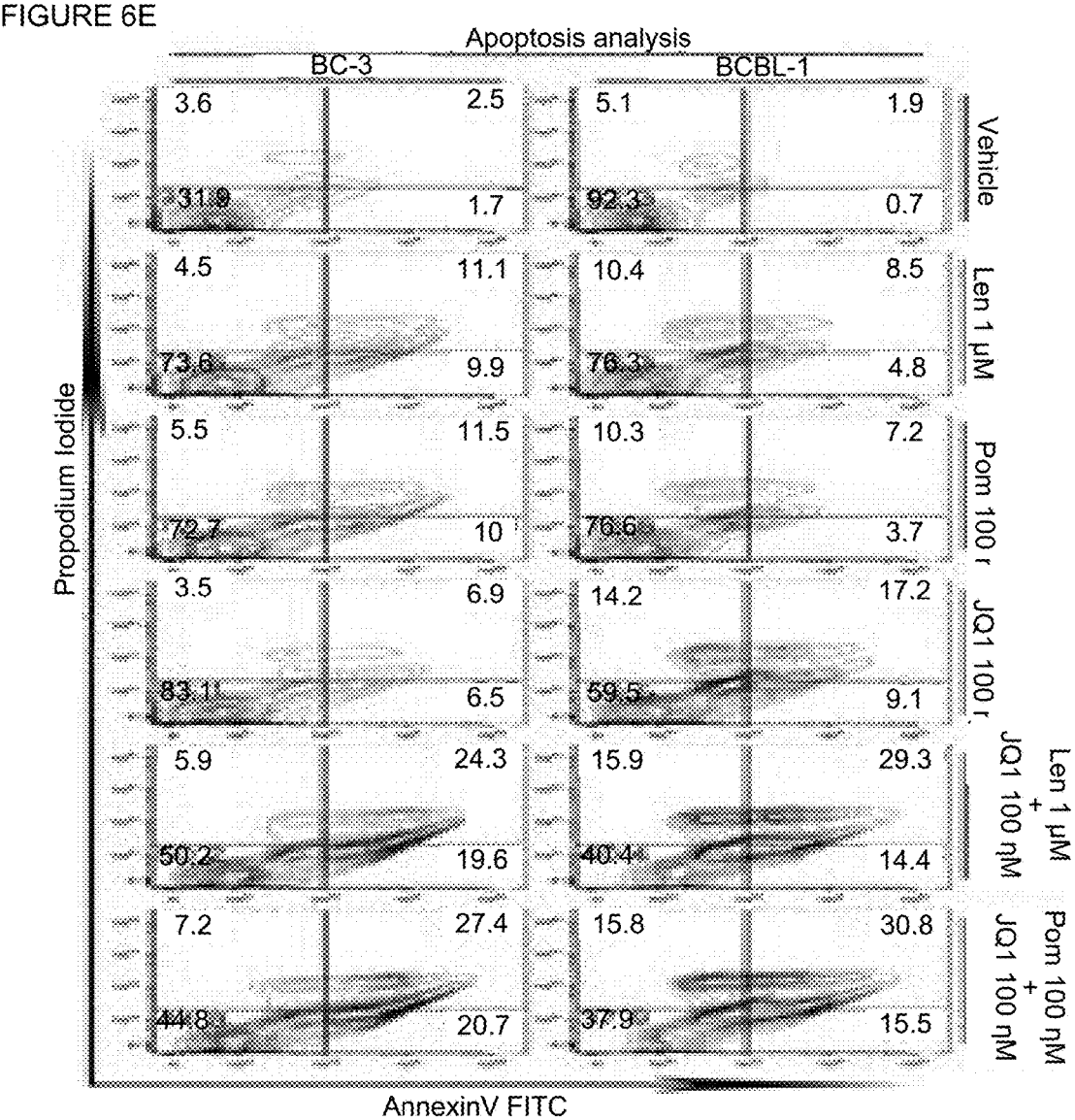

The above results suggest that IMiDs may show synergism with inhibition of MYC. MYC is an intracellular transcriptional factor which is considered undruggable. Recently, it has been shown that MYC transcription can be targeted using BRD4 inhibitors (Delmore et al., 2011; Mertz et al., 2011; Tolani et al., 2013). To test whether IMiDs show synergistic anti-proliferative activity with BRD4 inhibitors, we treated BC-3 and BCBL-1 cells with low doses of lenalidomide in combination with low doses of three structurally different BRD4 inhibitors JQ-1, IBET151 and PFI-1 followed by the calculation of combination index (CI) values using the calcusyn software, which is based on the method of Chou and Talalay (Chou and Talalay, 1983). Each BRD4 inhibitor was tested in combination with lenalidomide at 12 different combinations in BC-3 and BCBL-1 cells. Lenalidomide is highly synergistic with all three BRD4 inhibitors at all the combination doses tested in both BC-3 and BCBL-1 cells (FIG. 6A and FIG. 14A). Further, combined treatment of IMiDs with JQ-1 significantly decreased the expression of MYC and IRF4 than either alone in BC-3 and BCBL-1 cells (FIG. 6B). And it is pertinent to note that at the doses checked only the combined treatment resulted in the cleavage of PARP in BC-3 and BCBL-1 cells (FIG. 6B). Combination of lenalidomide with JQ-1 also resulted in a significant decrease in the mRNA levels of both MYC and IRF4 than either agent alone (FIG. 6C). Cell cycle analysis revealed that combined treatment of IMiDs with JQ-1 resulted in a significant increase in the number of cells arrested in G1 phase with a concurrent decrease in the number of cells in S phase (FIG. 6D) in both BC-3 and BCBL-1 cells than either agent alone and a significant apoptotic peak was visible only in the combination treatment in BCBL-1 cells (FIG. 6D). Further, combined treatment of IMiDs with JQ-1 also resulted in a significant increase in the number of cells undergoing apoptosis as observed by annexinV-FITC staining in BC-3 and BCBL-1 cells (FIG. 6E). The above data clearly shows that combined treatment of IMiDs with BRD4 inhibitors will produce a synergistic anti-proliferative effect in PEL.

Example XVI

Knocking Down BRD4 by shRNA Also Enhances the Sensitivity of IMiDs to PEL

Figures 7A, 7B, 7C:
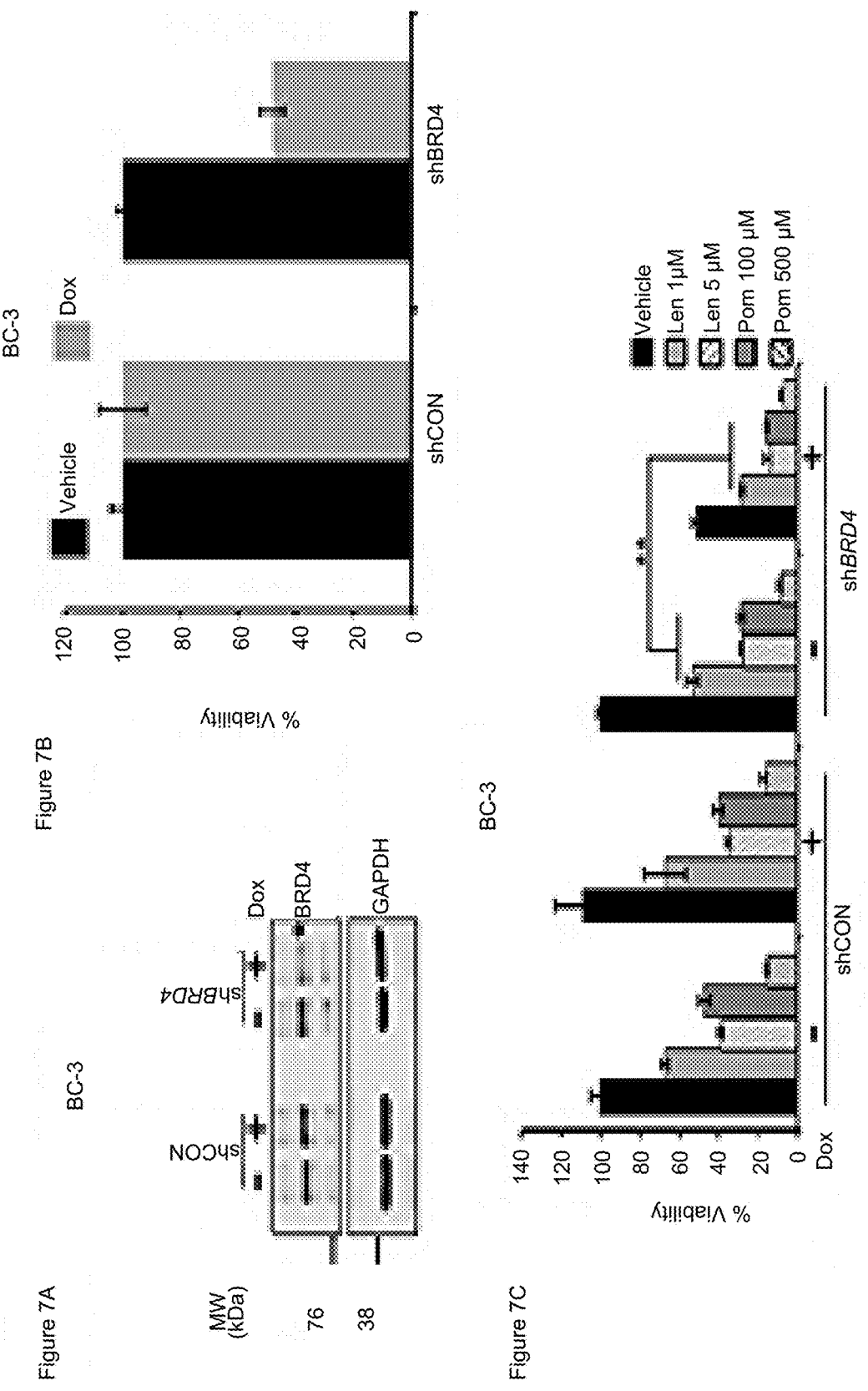
FIGS. 7A-7E. Knocking down BRD4 also enhances the anti-proliferative effect of IMiDs in PEL and combination treatment of lenalidomide and JQ-1 extends the survival of NOD.SCID mice bearing PEL.
Figure 7E:
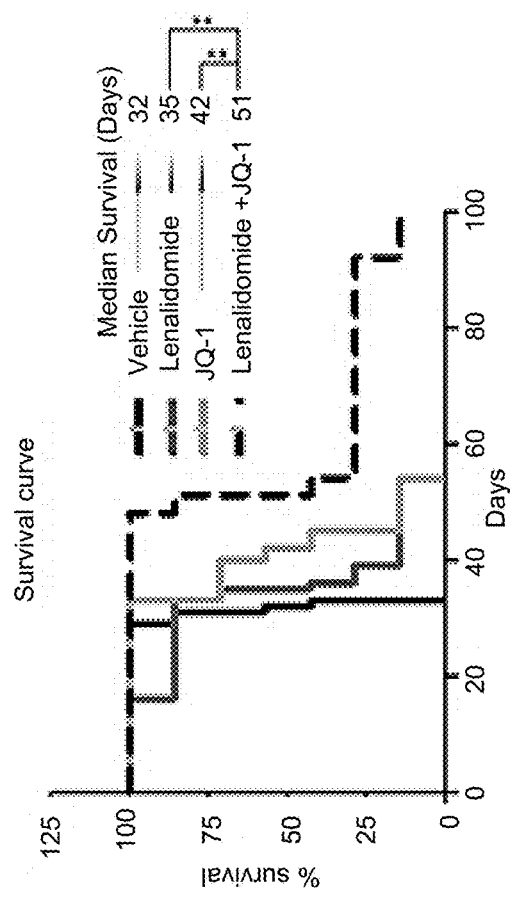
Figure 7D:
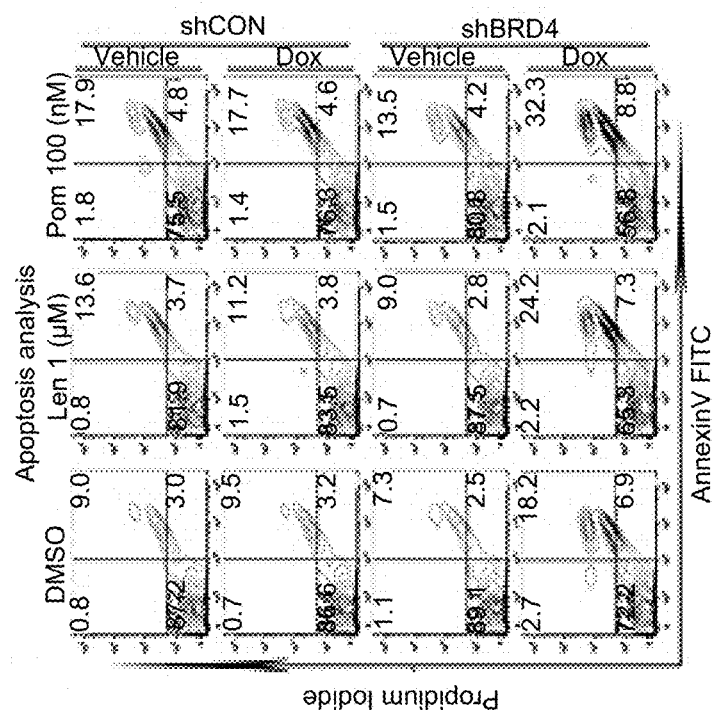
Figure 14:
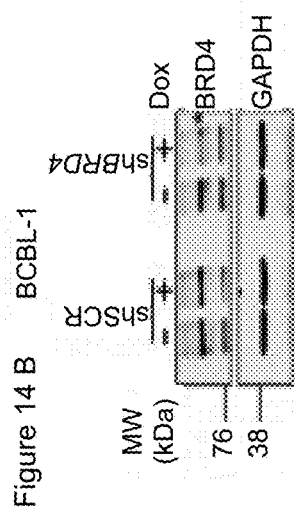
FIGS. 14A-14D.
Figure 14:
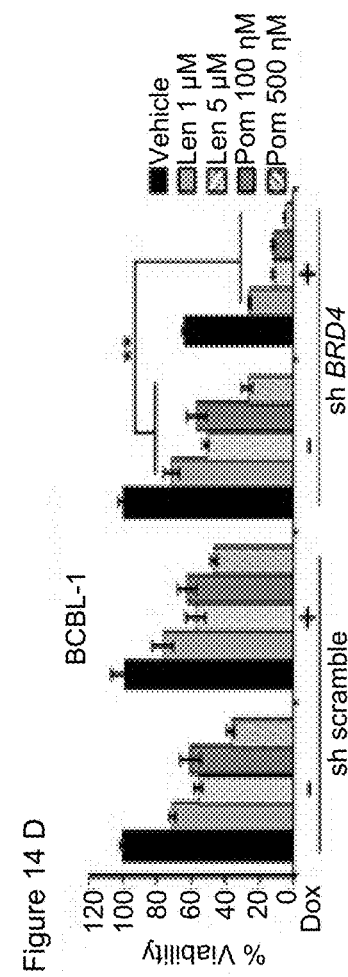
Figure 14:
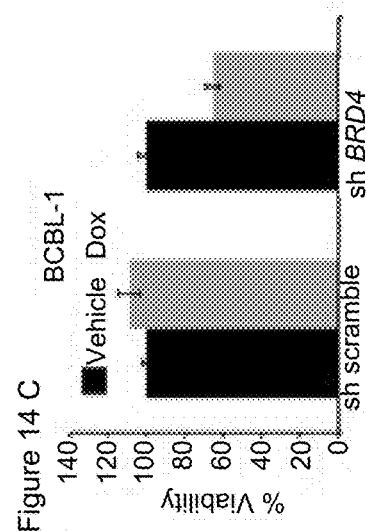
Figure 15:
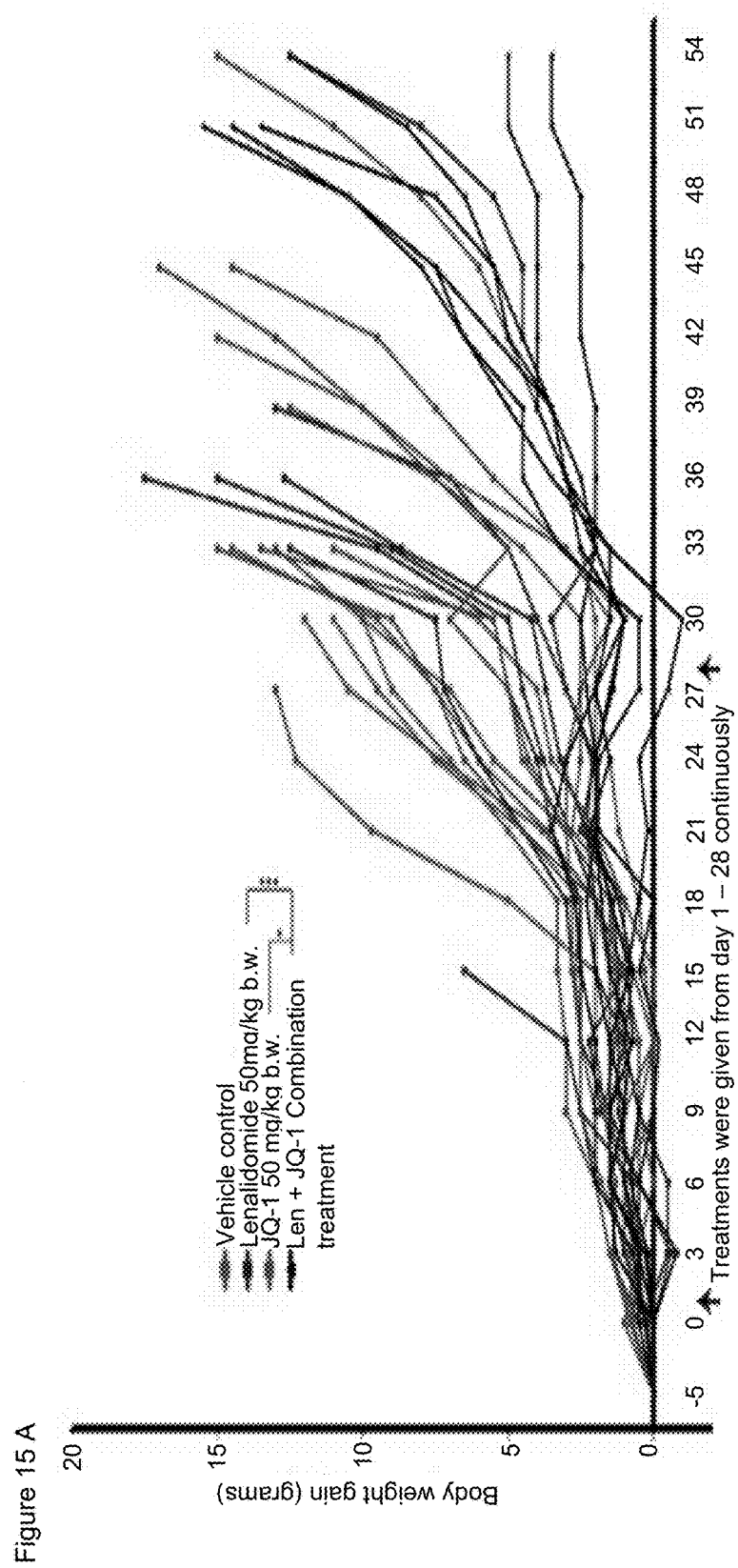
FIGS. 15A-15B.
Figure 15:
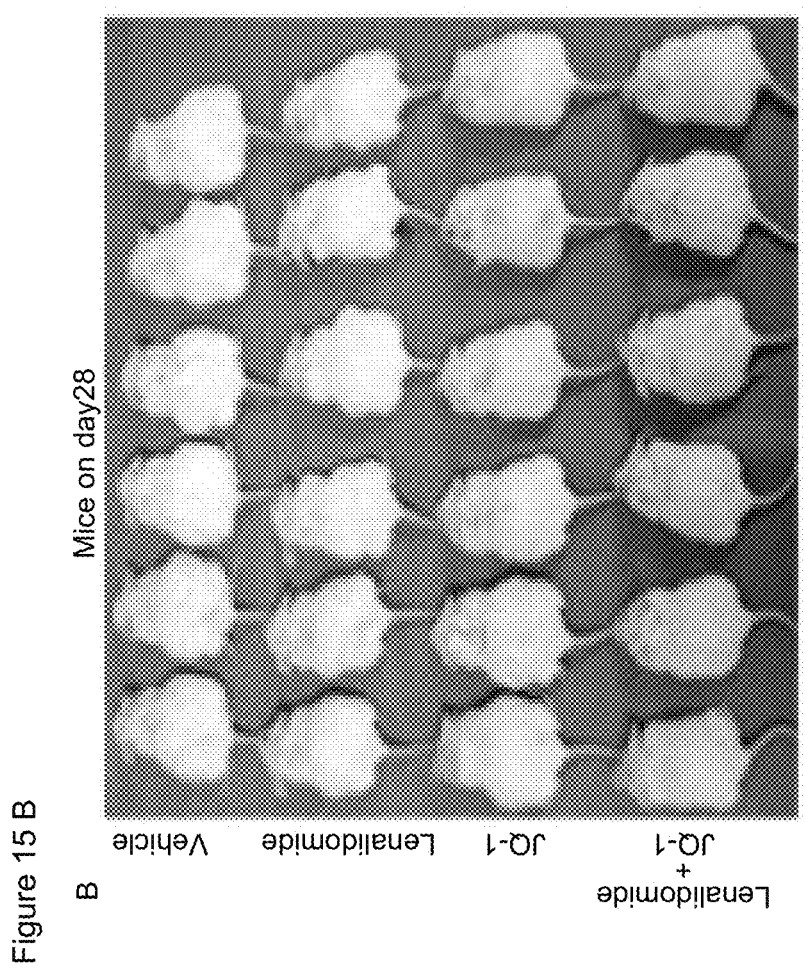

JQ-1, IBET151 and PFI-1 are BRD4 inhibitors (Dawson et al., 2011; Filippakopoulos et al., 2010; Picaud et al., 2013). Of these, JQ-1 is the first in class BRD4 inhibitor discovered in 2010 (Filippakopoulos et al., 2010) within 4 years of JQ-1 discovery vast number of small molecule BRD4 inhibitors were discovered (Garnier et al., 2014). Of these, 5 inhibitors are already being tested in phase I-II clinical trials for various diseases including leukemia, lymphoma, carcinoma, atherosclerosis and diabetes (Filippakopoulos and Knapp, 2014). To test whether the observed synergism between IMiDs and the BRD4 inhibitors is limited to the 3 BRD4 inhibitors used in this study or can be applicable to all the available BRD4 inhibitors we generated stable clones of BC-3 and BCBL-1 cells expressing tetracycline-inducible-H1-promoter (H1/TO)-driven shRNA targeting BRD4 (shBRD4). Treatment of BC-3 and BCBL-1 cells stably expressing shBRD4 with Dox resulted in a significant down regulation of BRD4 (FIG. 7A and FIG. 14B). In contrast, shRNA targeting scrambled sequence (shSCR) did not have any effect on the expression of BRD4 (FIG. 7A and FIG. 14B). Treatment of BC-3 and BCBL-1 cells stably expressing shBRD4 with Dox significantly decreased the proliferation of cells by an approximate 50% and 40%, respectively (FIG. 7B and FIG. 14C). In contrast, treatment of BC-3 and BCBL-1 cells stably expressing shSCR with Dox C for 4 days did not have any significant effect on proliferation (FIG. 7B and FIG. 14). This data confirms that BRD4 is a viable target for the treatment for PEL (Tolani et al., 2013). We next tested the effect of BRD4 knockdown on the anti-proliferative activity of IMiDs on BC-3 and BCBL-1 cells stably expressing shBRD4 by co-treating them with increasing doses of IMiDs and Dox. As shown in FIG. 7C and FIG. 14D, knocking down BRD4 significantly increased the anti-proliferative activity of IMiDs towards BC-3 and BCBL-1 cells. Further, apoptosis analysis by annexinV-FITC staining on BC-3 cells stably expressing shBRD4 with IMiDs in the presence/absence of Dox clearly shows the cells co-treated with IMiDs and Dox have a significant increase in the number of cells undergoing apoptosis (FIG. 7D). In contrast, no significant difference was observed in BC-3 cells stably expressing shSCR treated with IMiDs in the presence/absence of Dox in both cell proliferation and apoptosis analysis (FIGS. 7C, 7D and FIG. 14D). This data indicates that IMiDs may exert its synergistic anti-proliferative effect on PEL not only with the 3 BRD4 inhibitors used in this study and may also on BRD4 inhibitors as whole.

Example XVII

Combined Treatment of Lenalidomide and JQ-1 Increased Survival of Mice Bearing PEL than Either Agent Alone To check the in vivo efficacy of lenalidomide in combination with JQ-1, we utilized an orthotropic xenograft model in which BC-3 cells were injected into the intra-peritoneal cavity of NOD.SCID mice. Five days after the injection animals were randomly assigned to vehicle control, lenalidomide (50 mg/kg once daily for 28 days), JQ-1 (50 mg/kg once daily for 28 days), and the combination. Intra-peritoneal inoculation of BC-3 cells resulted in rapid tumor growth, massive ascites which resulted in body weight gain (FIG. 7E, FIGS. 14A and 14B). Animals treated with the combination of lenalidomide and JQ-1 showed significant decrease in body weight gain over time when compared with either agent alone (FIGS. 14A and 14B). In addition, the median survival of combination treatment is 51 days which is significantly ($p \leq 0.01$) increased when compared with lenalidomide (35 days) and JQ-1 (42 days) alone (FIG. 7E).

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references are each relied upon and incorporated herein in their entirety.

Antar, A., El Hajj, H., Jabbour, M., Khalifeh, I., El-Merhi, F., Mahfouz, R., and Bazarbachi, A. (2014). Primary effusion lymphoma in an elderly patient effectively treated by lenalidomide: case report and review of literature. Blood cancer journal 4, e190.

Bahram, F., von der Lehr, N., Cetinkaya, C., and Larsson, L. G. (2000). c-Myc hot spot mutations in lymphomas result in inefficient ubiquitination and decreased proteasome-mediated turnover. Blood 95, 2104-2110.

Boulanger, E., Gerard, L., Gabarre, J., Molina, J. M., Rapp, C., Abino, J. F., Cadranel, J., Chevret, S., and Oksenhendler, E. (2005). Prognostic factors and outcome of human herpesvirus 8-associated primary effusion lymphoma in patients with AIDS. J Clin Oncol 23, 4372-4380.

Broyl, A., Kuiper, R., van Duin, M., van der Holt, B., el Jarari, L., Bertsch, U., Zweegman, S., Buijs, A., Hose, D., Lokhorst, H. M., et al. (2013). High cereblon expression is associated with better survival in patients with newly diagnosed multiple myeloma treated with thalidomide maintenance. Blood 121, 624-627.

Carbone, A., Gloghini, A., Cozzi, M. R., Capello, D., Steffan, A., Monini, P., De Marco, L., and Gaidano, G. (2000). Expression of MUM1/IRF4 selectively clusters with primary effusion lymphoma among lymphomatous effusions: implications for disease histogenesis and pathogenesis. Br J Haematol 111, 247-257.

Cesarman, E., Chang, Y., Moore, P. S., Said, J. W., and Knowles, D. M. (1995). Kaposi's sarcoma-associated herpesvirus-like DNA sequences in AIDS-related body-cavity-based lymphomas. N Engl J Med 332, 1186-1191.

Chaudhary, P. M., Jasmin, A., Eby, M. T., and Hood, L. (1999). Modulation of the NF-kappa B pathway by virally encoded death effector domains-containing proteins. Oncogene 18, 5738-5746.

Chen, N., Lau, H., Kong, L., Kumar, G., Zeldis, J. B., Knight, R., and Laskin, O. L. (2007). Pharmacokinetics of lenalidomide in subjects with various degrees of renal impairment and in subjects on hemodialysis. J Clin Pharmacol 47, 1466-1475.

Chou, and Talalay, P. (1983). Analysis of combined drug effects: a new look at a very old problem. Trends in pharmacological sciences 4, 450-454.

D'Amato, R. J., Lentzsch, S., and Rogers, M. S. (2013). Pomalidomide is strongly antiangiogenic and teratogenic in relevant animal models. Proc Natl Acad Sci USA 110, E4818.

Dawson, M. A., Prinjha, R. K., Dittmann, A., Giotopoulos, G., Bantscheff, M., Chan, W. I., Robson, S. C., Chung, C. W., Hopf, C., Savitski, M. M., et al. (2011). Inhibition of BET recruitment to chromatin as an effective treatment for MLL-fusion leukaemia. Nature 478, 529-533.

Delmore, J. E., Issa, G. C., Lemieux, M. E., Rahl, P. B., Shi, J., Jacobs, H. M., Kastritis, E., Gilpatrick, T., Paranal, R. M., Qi, J., et al. (2011). BET bromodomain inhibition as a therapeutic strategy to target c-Myc. Cell 146, 904-917.

Dimopoulos, M. A., Terpos, E., and Niesvizky, R. (2013). How lenalidomide is changing the treatment of patients with multiple myeloma. Crit Rev Oncol Hematol 88 Suppl 1, S23-35.

Filippakopoulos, P., and Knapp, S. (2014). Targeting bromodomains: epigenetic readers of lysine acetylation. Nat Rev Drug Discov 13, 337-356.

Filippakopoulos, P., Qi, J., Picaud, S., Shen, Y., Smith, W. B., Fedorov, O., Morse, E. M., Keates, T., Hickman, T. T., Felletar, I., et al. (2010). Selective inhibition of BET bromodomains. Nature 468, 1067-1073.

Garnier, J. M., Sharp, P. P., and Burns, C. J. (2014). BET bromodomain inhibitors: a patent review. Expert opinion on therapeutic patents 24, 185-199.

Gopalakrishnan, R., Matta, H., and Chaudhary, P. M. (2013). A purine scaffold HSP90 inhibitor BIIBO21 has selective activity against KSHV-associated Primary Effusion Lymphoma and blocks vFLIP K13-induced NF-kappaB. Clin Cancer Res.

Gopalakrishnan, R., Matta, H., Tolani, B., Triche, T. Jr. and Chaudhary, P. M. Immunomodulatory drugs target IKZF1-IRF4-MYC axis in primary effusion lymphoma in a cereblon-dependent manner and display synergistic cytotoxicity with BRD4 inhibitors. Oncogene, Jun. 29, 2015 (online abstract, publication pending).

Guasparri, I., Keller, S. A., and Cesarman, E. (2004). KSHV vFLIP is essential for the survival of infected lymphoma cells. J Exp Med 199, 993-1003.

Ito, T., Ando, H., Suzuki, T., Ogura, T., Hotta, K., Imamura, Y., Yamaguchi, Y., and Handa, H. (2010). Identification of a primary target of thalidomide teratogenicity. Science 327, 1345-1350.

John, L. B., and Ward, A. C. (2011). The Ikaros gene family: transcriptional regulators of hematopoiesis and immunity. Mol Immunol 48, 1272-1278.

Keller, S. A., Schattner, E. J., and Cesarman, E. (2000). Inhibition of NF-kappaB induces apoptosis of KSHV-infected primary effusion lymphoma cells. Blood 96, 2537-2542.

Kobayashi, Y., Kamitsuji, Y., Kuroda, J., Tsunoda, S., Uoshima, N., Kimura, S., Wada, K., Matsumoto, Y., Nomura, K., Horiike, S., et al. (2007). Comparison of human herpes virus 8 related primary effusion lymphoma with human herpes virus 8 unrelated primary effusion lymphoma-like lymphoma on the basis of HIV: report of 2 cases and review of 212 cases in the literature. Acta Haematol 117, 132-144.

Kronke, J., Udeshi, N. D., Narla, A., Grauman, P., Hurst, S. N., McConkey, M., Svinkina, T., Heckl, D., Comer, E., Li, X., et al. (2014). Lenalidomide causes selective degradation of IKZF1 and IKZF3 in multiple myeloma cells. Science 343, 301-305.

Libermann, T. A., and Baltimore, D. (1990). Activation of interleukin-6 gene expression through the NF-kappa B transcription factor. Mol Cell Biol 10, 2327-2334.

Lopez-Girona, A., Heintel, D., Zhang, L. H., Mendy, D., Gaidarova, S., Brady, H., Bartlett, J. B., Schafer, P. H., Schreder, M., Bolomsky, A., et al. (2011). Lenalidomide downregulates the cell survival factor, interferon regulatory factor-4, providing a potential mechanistic link for predicting response. Br J Haematol 154, 325-336.

Lopez-Girona, A., Mendy, D., Ito, T., Miller, K., Gandhi, A. K., Kang, J., Karasawa, S., Carmel, G., Jackson, P., Abbasian, M., et al. (2012). Cereblon is a direct protein target for immunomodulatory and antiproliferative activities of lenalidomide and pomalidomide. Leukemia 26, 2326-2335.

Lu, G., Middleton, R. E., Sun, H., Naniong, M., Ott, C. J., Mitsiades, C. S., Wong, K. K., Bradner, J. E., and Kaelin, W. G., Jr. (2014). The myeloma drug lenalidomide promotes the cereblon-dependent destruction of Ikaros proteins. Science 343, 305-309.

Mertz, J. A., Conery, A. R., Bryant, B. M., Sandy, P., Balasubramanian, S., Mele, D. A., Bergeron, L., and Sims, R. J., 3rd (2011). Targeting MYC dependence in cancer by inhibiting BET bromodomains. Proc Natl Acad Sci USA 108, 16669-16674.

Patel, S., and Xiao, P. (2013). Primary effusion lymphoma. Arch Pathol Lab Med 137, 1152-1154.

Petroski, M. D., and Deshaies, R. J. (2005). Function and regulation of cullin-RING ubiquitin ligases. Nat Rev Mol Cell Biol 6, 9-20.

Picaud, S., Da Costa, D., Thanasopoulou, A., Filippakopoulos, P., Fish, P. V., Philpott, M., Fedorov, O., Brennan, P., Bunnage, M. E., Owen, D. R., et al. (2013). PFI-1, a highly selective protein interaction inhibitor, targeting BET Bromodomains. Cancer Res 73, 3336-3346.

Qin, Z., Dai, L., Trillo-Tinoco, J., Senkal, C., Wang, W., Reske, T., Bonstaff, K., Del Valle, L., Rodriguez, P., Flemington, E., et al. (2014). Targeting sphingosine kinase induces apoptosis and tumor regression for KSHV-associated primary effusion lymphoma. Mol Cancer Ther 13, 154-164.

Richardson, P. G., Mark, T. M., and Lacy, M. Q. (2013). Pomalidomide: new immunomodulatory agent with potent antiproliferative effects. Crit Rev Oncol Hematol 88 Suppl 1, S36-44.

Riva, G., Luppi, M., Barozzi, P., Forghieri, F., and Potenza, L. (2012). How I treat HHV8/KSHV-related diseases in posttransplant patients. Blood 120, 4150-4159.

Shaffer, A. L., Emre, N. C., Lamy, L., Ngo, V. N., Wright, G., Xiao, W., Powell, J., Dave, S., Yu, X., Zhao, H., et al. (2008). IRF4 addiction in multiple myeloma. Nature 454, 226-231.

Shaffer, A. L., Emre, N. C., Romesser, P. B., and Staudt, L. M. (2009). IRF4: Immunity. Malignancy! Therapy?Clin Cancer Res 15, 2954-2961.

Shin, K. J., Wall, E. A., Zavzavadjian, J. R., Santat, L. A., Liu, J., Hwang, J. I., Rebres, R., Roach, T., Seaman, W., Simon, M. I., et al. (2006). A single lentiviral vector platform for microRNA-based conditional RNA interference and coordinated transgene expression. Proc Natl Acad Sci USA 103, 13759-13764.

Smith, M. L., Baggerly, K. A., Bengtsson, H., Ritchie, M. E., and Hansen, K. D. (2013). illuminaio: An open source IDAT parsing tool for Illumina microarrays. F1000Research 2, 264.

Smyth, G. K. (2005). Limma: linear models for microarray data. (New York: Springer).

Soucy, T. A., Smith, P. G., Milhollen, M. A., Berger, A. J., Gavin, J. M., Adhikari, S., Brownell, J. E., Burke, K. E., Cardin, D. P., Critchley, S., et al. (2009). An inhibitor of NEDD8-activating enzyme as a new approach to treat cancer. Nature 458, 732-736.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.

Tolani, B., Gopalakrishnan, R., Punj, V., Matta, H., and Chaudhary, P. M. (2013). Targeting Myc in KSHV-associated primary effusion lymphoma with BET bromodomain inhibitors. Oncogene.

Yang, Y., Groshong, J. S., Matta, H., Gopalakrishnan, R., Yi, H., and Chaudhary, P. M. (2011). Constitutive NF-kappaB Activation Confers Interleukin 6 (IL6) Independence and Resistance to Dexamethasone and Janus Kinase Inhibitor INCB018424 in Murine Plasmacytoma Cells. J Biol Chem 286, 27988-27997.

Yang, Y., Shaffer, A. L., 3rd, Emre, N. C., Ceribelli, M., Zhang, M., Wright, G., Xiao, W., Powell, J., Platig, J., Kohlhammer, H., et al. (2012). Exploiting synthetic lethality for the therapy of ABC diffuse large B cell lymphoma. Cancer Cell 21, 723-737.

Zhao, J., Punj, V., Matta, H., Mazzacurati, L., Schamus, S., Yang, Y., Yang, T., Hong, Y., and Chaudhary, P. M. (2007). K13 Blocks KSHV Lytic Replication and Deregulates vIL6 and hIL6 Expression: a Model of Lytic Replication Induced Clonal Selection in Viral Oncogenesis. PLoS ONE 2, e1067.

Zhu, X., Santat, L. A., Chang, M. S., Liu, J., Zavzavadjian, J. R., Wall, E. A., Kivork, C., Simon, M. I., and Fraser, I. D. (2007). A versatile approach to multiple gene RNA interference using microRNA-based short hairpin RNAs. BMC Mol Biol 8, 98.

Zhu, Y. X., Braggio, E., Shi, C. X., Bruins, L. A., Schmidt, J. E., Van Wier, S., Chang, X. B., Bjorklund, C. C., Fonseca, R., Bergsagel, P. L., et al. (2011). Cereblon expression is required for the antimyeloma activity of lenalidomide and pomalidomide. Blood 118, 4771-4779.

Zhu, Y. X., Kortuem, K. M., and Stewart, A. K. (2013). Molecular mechanism of action of immune-modulatory drugs thalidomide, lenalidomide and pomalidomide in multiple myeloma. Leuk Lymphoma 54, 683-687.

What is claimed is:

1. A method of treating primary effusion lymphoma (PEL) comprising administering to a patient in need thereof an effective amount of an immunomodulatory compound selected from the group consisting of

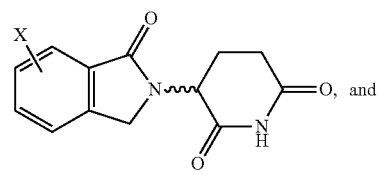

Formula IV

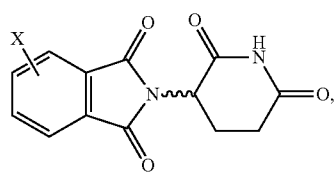

Formula V wherein X in Formula IV and Formula V may be independently selected from the group consisting of hydrogen, a halide, an aliphatic group and an amine group; and a BRD4 inhibitor selected from the group consisting of

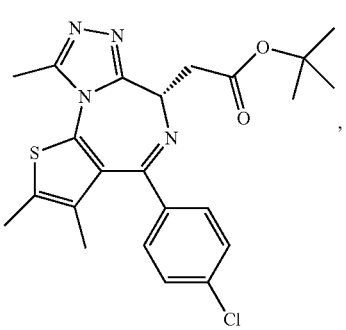

Formula VI (also known as compound JQ-1)

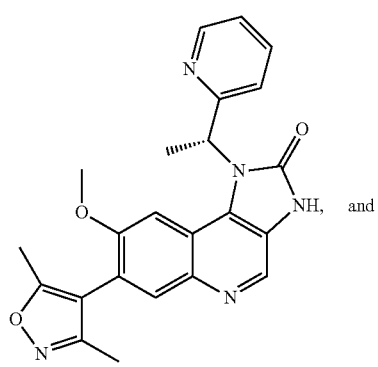

Formula VII (also known as compound IBET151)

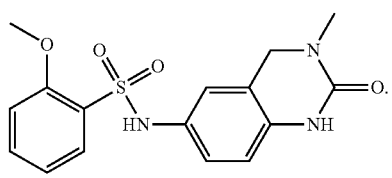

Formula VIII (also known as compound PFI-1)

2. The method of claim 1, wherein the immunomodulatory compound and the BRD4 inhibitor are administered orally or parenterally, by intravenous, intramuscular, topical or subcutaneous routes or intraperitoneally by infusion or injection.

3. The method of claim 1, wherein the immunomodulatory compound or pharmaceutically acceptable salt thereof is provided as a composition comprising the compound or pharmaceutically acceptable salt thereof and a pharmaceutically acceptable carrier suitable for oral, parenteral, or topical administration.

4. The method of claim 1, wherein the immunomodulatory compound and the BRD4 inhibitor or pharmaceutically acceptable salts thereof are provided as a composition comprising the compound and the BRD4 inhibitor or pharmaceutically acceptable salts thereof and a pharmaceutically acceptable carrier suitable for oral, parenteral, or topical administration.

5. The method of claim 1, wherein the immunomodulatory compound and the BRD4 inhibitor are administered intraperitoneally by infusion or injection.

\* \* \* \* \*

UNITED STATES PATENT AND TRADEMARK OFFICE
CERTIFICATE OF CORRECTION

PATENT NO. : 9,931,332 B2
APPLICATION NO. : 14/814149
DATED : April 3, 2018
INVENTOR(S) : Chaudhary et al.

Page 1 of 1

It is certified that error appears in the above-identified patent and that said Letters Patent is hereby corrected as shown below:

In the Specification

Please delete the paragraph beginning on Line 16 and ending on Line 19 of Column 1, and replace with the following paragraph:
--This invention was made with government support under DE019811, P30 CA014089, TR000130, and CA139119 awarded by the National Institutes of Health. The government has certain rights in the invention.--

Signed and Sealed this
First Day of April, 2025

Coke Morgan Stewart
*Acting Director of the United States Patent and Trademark Office*